US010898584B2

(12) United States Patent
Schlake et al.

(10) Patent No.: US 10,898,584 B2
(45) Date of Patent: Jan. 26, 2021

(54) MODIFIED RNA WITH DECREASED IMMUNOSTIMULATORY PROPERTIES

(71) Applicant: CureVac Ag, Tübingen (DE)

(72) Inventors: Thomas Schlake, Gundelfingen (DE); Andreas Thess, Kusterdingen (DE)

(73) Assignee: CureVac AG, Tübingen (DE)

( * ) Notice: Subject to any disclaimer, the term of this patent is extended or adjusted under 35 U.S.C. 154(b) by 127 days.

(21) Appl. No.: 15/142,082

(22) Filed: Apr. 29, 2016

(65) Prior Publication Data
US 2016/0235864 A1    Aug. 18, 2016

Related U.S. Application Data

(63) Continuation of application No. PCT/EP2014/002931, filed on Oct. 31, 2014.

(51) Int. Cl.
A61K 48/00 (2006.01)
A61K 31/7105 (2006.01)
A61K 38/38 (2006.01)
A61K 38/44 (2006.01)
C07K 14/76 (2006.01)
C12P 19/34 (2006.01)
G01N 33/74 (2006.01)

(52) U.S. Cl.
CPC ........ A61K 48/005 (2013.01); A61K 31/7105 (2013.01); A61K 38/38 (2013.01); A61K 38/44 (2013.01); C07K 14/76 (2013.01); C12P 19/34 (2013.01); G01N 33/74 (2013.01); C12Y 113/12007 (2013.01)

(58) Field of Classification Search
None
See application file for complete search history.

(56) References Cited

U.S. PATENT DOCUMENTS

| | | |
|---|---|---|
| 3,906,092 A | 9/1975 | Hilleman et al. |
| 4,373,071 A | 2/1983 | Ltakura |
| 4,401,796 A | 8/1983 | Ltakura |
| 4,415,732 A | 11/1983 | Caruthers et al. |
| 4,458,066 A | 7/1984 | Caruthers et al. |
| 4,500,707 A | 2/1985 | Caruthers et al. |
| 4,588,585 A | 5/1986 | Mark et al. |
| 4,668,777 A | 5/1987 | Caruthers et al. |
| 4,737,462 A | 4/1988 | Mark et al. |
| 4,816,567 A | 3/1989 | Cabilly et al. |
| 4,879,111 A | 11/1989 | Chong |
| 4,959,314 A | 9/1990 | Mark et al. |
| 4,973,679 A | 11/1990 | Caruthers et al. |
| 5,017,691 A | 5/1991 | Lee et al. |
| 5,047,524 A | 9/1991 | Andrus et al. |
| 5,116,943 A | 5/1992 | Koths et al. |
| 5,132,418 A | 7/1992 | Caruthers et al. |
| 5,153,319 A | 10/1992 | Caruthers et al. |
| 5,262,530 A | 11/1993 | Andrus et al. |
| 5,580,859 A | 12/1996 | Feigner et al. |
| 5,663,153 A | 9/1997 | Hutcherson et al. |
| 5,700,642 A | 12/1997 | Monforte et al. |
| 5,928,649 A | 7/1999 | Daley et al. |
| 5,965,720 A | 10/1999 | Gryaznov et al. |
| 5,965,726 A | 10/1999 | Pavlakis et al. |
| 6,214,804 B1 | 4/2001 | Feigner et al. |
| 6,239,116 B1 | 5/2001 | Krieg et al. |
| 6,265,387 B1 | 7/2001 | Wolff et al. |
| 6,322,967 B1 | 11/2001 | Parkin |
| 6,376,248 B1 | 4/2002 | Hawley-Nelson et al. |
| 6,406,705 B1 | 6/2002 | Davis et al. |
| 6,500,919 B1 | 12/2002 | Adema et al. |
| 6,514,948 B1 | 2/2003 | Raz et al. |
| 6,552,006 B2 | 4/2003 | Raz et al. |
| 6,589,940 B1 | 7/2003 | Raz et al. |
| 6,610,661 B1 | 8/2003 | Carson et al. |
| 6,664,066 B2 | 11/2003 | Parks |
| 6,924,365 B1 | 8/2005 | Miller et al. |
| 7,001,890 B1 | 2/2006 | Wagner et al. |
| 7,208,478 B2 | 4/2007 | Carson et al. |
| 7,268,120 B1 | 9/2007 | Horton et al. |
| 7,276,489 B2 | 10/2007 | Agrawal et al. |
| 7,316,925 B2 | 1/2008 | Draghia-Akli et al. |
| 2002/0123099 A1 | 9/2002 | Weiner et al. |
| 2002/0132788 A1 | 9/2002 | Lewis et al. |
| 2003/0008342 A1 | 1/2003 | Scholler et al. |
| 2003/0077604 A1 | 4/2003 | Sun et al. |
| 2003/0143204 A1 | 7/2003 | Lewis et al. |

(Continued)

FOREIGN PATENT DOCUMENTS

| | | |
|---|---|---|
| CA | 2854685 | 8/2002 |
| CA | 2473135 | 6/2003 |

(Continued)

OTHER PUBLICATIONS

Sharp et al., Nucleic Acids Research, 1987, vol. 15(3) pp. 1281-1295.*
Aissani el al., "CpG islands, genes and isochores in the genomes of vertebrates," Gene, 106:185-195, 1991.
Akashi, "Gene expression and molecular evolution," Curr. Opin. Genet. Dev., 11 (6):660-666, 2001.
Alberts et al., Molecular Biology of the Cell, 3$^{rd}$ Ed., Garland Publishing, Inc. New York, NY, pp. 368-369, 1994.
Altschul et al., "Gapped BLAST and PSI-BLAST: a new generation of protein database search programs," Nucleic Acids Res., 25(17):3389-3402, 1997.
Anichini et al., "Cytotoxic T cells directed to tumor antigen not expressed on normal melanocytes dominate HLA-A2 1-restricted immune repertoire to melanoma," J Immunol., 156(1):208-217, 1996.

(Continued)

Primary Examiner — Nancy J Leith
(74) Attorney, Agent, or Firm — Parker Highlander PLLC

(57) ABSTRACT

The present invention provides a method for providing modified mRNAs of reduced immunogenicity and/or immunostimulatory capacity for use in protein replacement therapy. The invention further provides modified mRNAs and pharmaceutical compositions comprising the modified mRNAs according to the invention for use in protein replacement therapy.

17 Claims, 11 Drawing Sheets
Specification includes a Sequence Listing.

(56) References Cited

U.S. PATENT DOCUMENTS

| | | |
|---|---|---|
| 2003/0143743 A1 | 7/2003 | Schuler et al. |
| 2003/0170273 A1 | 9/2003 | O'Hagan et al. |
| 2003/0225016 A1 | 12/2003 | Fearon et al. |
| 2004/0005667 A1 | 1/2004 | Ratti et al. |
| 2004/0106567 A1 | 6/2004 | Hagstrom et al. |
| 2005/0032730 A1 | 2/2005 | Von der Mulbe et al. |
| 2005/0037494 A1 | 2/2005 | Hecker et al. |
| 2005/0059624 A1 | 3/2005 | Hoerr et al. |
| 2005/0064596 A1 | 3/2005 | Riemen et al. |
| 2005/0112141 A1 | 5/2005 | Terman |
| 2005/0250723 A1 | 11/2005 | Hoerr et al. |
| 2006/0172966 A1 | 8/2006 | Lipford et al. |
| 2006/0188490 A1 | 8/2006 | Hoerr et al. |
| 2006/0241076 A1 | 10/2006 | Uhlmann et al. |
| 2008/0025944 A1 | 1/2008 | Hoerr et al. |
| 2008/0171711 A1 | 7/2008 | Hoerr et al. |
| 2008/0267873 A1 | 10/2008 | Hoerr et al. |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess et al. |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | Von Der Mulbe et al. |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |

FOREIGN PATENT DOCUMENTS

| | | | |
|---|---|---|---|
| CA | | 2376634 | 12/2005 |
| DE | | 10119005 | 4/2001 |
| EP | | 0175960 | 4/1986 |
| EP | | 0839912 | 5/1998 |
| EP | | 1083232 | 3/2001 |
| EP | | 1393745 | 3/2004 |
| JP | | 2000-509281 | 7/2000 |
| JP | | 7-503372 | 2/2007 |
| WO | WO 2016/091391 | | 6/1916 |
| WO | WO 2016/097065 | | 6/1916 |
| WO | WO 2016/107877 | | 7/1916 |
| WO | WO 1990/011092 | | 10/1990 |
| WO | WO 1993/014778 | | 8/1993 |
| WO | WO 1995/024485 | | 9/1995 |
| WO | WO 1995/026204 | | 10/1995 |
| WO | WO 1997/041210 | | 11/1997 |
| WO | WO 1997/048370 | | 12/1997 |
| WO | WO 1998/012207 | | 3/1998 |
| WO | WO 1998/034640 | | 8/1998 |
| WO | WO 1998/055495 | | 12/1998 |
| WO | WO 1999/014346 | | 3/1999 |
| WO | WO 1999/020774 | | 4/1999 |
| WO | WO 1999/052503 | | 10/1999 |
| WO | WO 2000/006723 | | 2/2000 |
| WO | WO 2000/029561 | | 5/2000 |
| WO | WO 2000/075304 | | 12/2000 |
| WO | WO 2001/004313 | | 1/2001 |
| WO | WO 2001/014416 | | 3/2001 |
| WO | WO 2001/021810 | | 3/2001 |
| WO | WO 2001/093902 | | 12/2001 |
| WO | WO 2002/008435 | | 1/2002 |
| WO | WO 2002/064799 | | 8/2002 |
| WO | WO 2002/098443 | | 12/2002 |
| WO | WO 2003/028656 | | 4/2003 |
| WO | WO 2003/051401 | | 6/2003 |
| WO | WO 2003/059381 | | 7/2003 |
| WO | WO 2003/066649 | | 8/2003 |
| WO | WO 2003/086280 | | 10/2003 |
| WO | WO 2004/058159 | | 7/2004 |
| WO | WO 2004/092329 | | 10/2004 |
| WO | WO 2006/008154 | | 1/2006 |
| WO | WO 2006/024518 | | 3/2006 |
| WO | WO 2006/049777 | | 5/2006 |
| WO | WO 2007/024708 | | 3/2007 |
| WO | WO 2009/127230 | | 10/2009 |
| WO | Wo-2009127230 A1 * | | 10/2009 ........... C12N 15/111 |
| WO | WO 2015/149944 | | 10/2015 |

OTHER PUBLICATIONS

Aota et al., "Diversity in G+C content at the third position of codons in vertebrate genes and its cause," *Nucleic Acids Research*, 14(16):6345-6356, 1986.

Apostolopoulos et al., "Cellular mucins: targets for immunotherapy," *Crit Rev Immunol.*, 14(3-4):293-309, 1994.

Ashley et al., "Bone marrow-generated dendritic cells pulsed with tumor extracts or tumor RNA induce antitumor immunity against central nervous system tumors," *J Exp Med.*, 186(7):1177-1182, 1997.

Aurup et al., "Translation of 2'-modified mRNA in vitro and in vivo," *Nucleic Acids Research*, 22(23):4963-4968, 1994.

Austyn, "New insights into the mobilization and phagocytic activity of dendritic cells," *J Exp Med.*, 183(4):1287-1292, 1996.

Bernardi, "Isochores and the evolutionary genomics of vertebrates," *Gene*, 241:3-17, 2000.

Bernardi, "The vertebrate genome: isochores and evolution," *Mol. Biol. Evol.* 10:186-204, 1993.

Berneman et al., "T-Cell Stimulatory Capacity of Different Types of In Vitro Cultured Monocyte-Derived Dendritic Cells Following Electroporation with RNA Encoding Defined Antigens," Laboratory of Experimental Hematology, University of Antwerp, 1(11), Abstract No. 5536, Nov. 16, 2002.

Bernhard et al., "Generation of immunostimulatory dendritic cells from human CD34+ hematopoietic progenitor cells of the bone marrow and peripheral blood," *Cancer Res.*, 55(5):1099-1104, 1995.

Bettinger et al., "Peptide-mediated RNA delivery: a novel approach for enhanced transfection of primary and post-mitotic cells," *Nucleic Acids Research*, 29(18):3882-3891, 2001.

Bevan, "Antigen presentation to cytotoxic T lymphocytes in vivo," *J Exp Med*, 182(3):639-641, 1995.

Bevilacqua et al., "Post-transcriptional regulation of gene expression by degradation of messenger RNAs," *Journal of Cellular Physiology*, 195(3):356-372, 2003.

Bieler und Wagner (in: Schleef), Plasmids for Therapy and Vaccination, Kapitel 9, Seiten 147-168, Wiley-VCH, Weinheim, 2001.

Binder et al., "Evidence that the pathway of transferrin receptor mRNA degradation involves an endonucleolytic cleavage within the 3' UTR and does not involve poly(A) tail shortening," *EMBO J.*, 13(8):1969-1980, 1994.

(56) References Cited

OTHER PUBLICATIONS

Bird, "CpG-rich islands and the function of DNA methylation," *Nature*, 321:209-213, 1986.
Boczkowski et al., "Dendritic cells pulsed with RNA are potent antigen-presenting cells in vitro and in vivo," *J. Exp. Med.*, 184:465-472, 1996.
Boczkowski el al., "Induction of tumor immunity and cytotoxic T lymphocyte responses using dendritic cells transfected with messenger RNA amplified from tumor cells," *Cancer Res.*, 60(4):1028-1034, 2000.
Boon et al., "Genes coding for tumor rejection antigens: perspectives for specific immunotherapy," *Important Adv Oncol*, 53-69, 1994.
Boyum, "Separation of white blood cells," *Nature*, 204:793-794, 1964.
Brandt et al., "Detection of the metastatic potential of blood-borne and immunomagnetically enriched epithelial cells by quantitative erbB-2 RT-PCR," *Clin. Exp. Metastasis*, 14:399-408, 1996.
Brossart et al., "Her-2/neu-derived peptides are tumor-associated antigens expressed by human renal cell and colon carcinoma lines and are recognized by in vitro induced specific cytotoxic T lymphocytes," *Cancer Res*, 58(4):732-736, 1998.
Brossart et al., "Identification of HLA-A2-restricted T-cell epitopes derived from the MUC1 tumor antigen for broadly applicable vaccine therapies," *Blood*, 93(12):4309-4317, 1999.
Brossart et al., "Induction of cytotoxic T-lymphocyte respones in vivo after vaccinations with peptide-pulsed dendritic cells," *Blood*, 96(9):3102-3108, 2000.
Brossart et al., "Virus-mediated delivery of antigenic epitopes into dendritic cells as a means to induce CTL," *J Immunol,*, 158(7):3270-3276, 1997.
Cannon et al., "RNA Based Vaccines," *DNA and Cell Biology*, 21(12): 953-961, 2002.
Caput et al., "Identification of a common nucleotide sequence in the 3'-untranslated region of mRNA molecules specifying inflammatory mediators," *Proc. Natl. Acad. Sci. USA*, 83:1670-1674, 1986.
Caron et al., "The human transcriptome map: clustering of highly expressed genes in chromosomal domains," *Science*, 291:1289, 2001.
Carralot et al., "Polarization of immunity induced by direct injection of naked sequence-stabilized mRNA vaccines," *Cell Mol Life Sci*, 61(18):2418-2424, 2004.
Carralot et al., "Production and characterization of amplified tumor-derived cRNA libraries to be used as vaccines against metastatic melanomas," *Genetic Vaccines and Therapy*, 3(6):1-10, 2005.
CD154, Wikipedia, the free encyclopedia, Jun. 25, 2010.
Celluzzi et al., "Peptide-pulsed dendritic cells induce antigen-specific CTL-mediated protective tumor immunity," *J Exp Med*, 183(1):283-287, 1996.
Chen et al., "Enhanced protection against a lethal influenza virus challenge by immunization with both hemagglutinin- and neuraminidase-expressing DNAs," *Vaccine*, 17(7-8):653-659, 1999.
Cheng et al., "Enhancement of Sindbis virus self-replicating RNA vaccine potency by linkage of *Mycobacterium tuberculosis* heat shock protein 70 gene to an antigen gene," *Journal of Immunology*, 166(10):6218-6226, 2001.
Cheng et al., "Enhancement of Sindbis virus self-replicating RNA vaccine potency by linkage of Herpes simplex virus type 1 VP22 protein to antigen," *J. Virol.*, 75(5):2368-2376, 2001.
Cho et al., "Enhanced cellular immunity to hepatits C virus non-structural proteins by codelivery of granulocyte macrophage-colony stimulating factor gene in intramuscular DNA immunization," *Vaccine*, 17(9-10):1136-1144, 1999.
Cohen et al., "Murine epidermal Langerhans cells and splenic dendritic cells present tumor-associated antigens to primed T cells," *Eur J Immunol.*, 24(2):315-319, 1994.
Colot and Rossignol, "Eukaryotic DNA methylation as an evolutionary device," *BioEssays*, 21:402-411, 1999.
Conry et al., "Characterization of a messenger RNA polynucleotide vaccine vector," *Cancer Research*, 55(7):1397-1400, 1995.
Coughlin et al., "Targeting adult and pediatric cancers via cell-based vaccines and the prospect of activated B lymphocytes as a novel modality," *Cancer Biology & Therapy*, 2(5):466-470, 2003.
Craig and Bickmore, "The distribution of CpG islands in mammalian chromosomes," *Nature Genetics*, 7:376-382, 1994.
Cramer et al., "Functional association between promoter structure and transcript alternative splicing," *PNAS*, 94:11456-11460, 1997.
Culver et al., Gene Therapy, A Handbook for Physicians, pp. 63-77, 1994.
Database Corenucleotide, NCBI Database accession No. AF033819, Aug. 2002.
Database Geneseq, Database accession No. AAV21762, Jul. 1998.
Deres et al., "In vivo priming of virus-specific cytotaxic T lymphocytes with synthetic lipopeptide vaccine," *Nature*, 342:561-564, 1989.
Deshayes et al., "Cell-penetrating peptides: tools for intracellular delivery of therapeutics," *Cell Mol Life Sci*, 62(16):1839-1849, 2005.
Diebold et al., "Innate antiviral responses by means of TLR7-mediated recognition of single-stranded RNA," *Science*, 303(5663):1529-1531, 2004.
Disbrow et al., "Codon optimization of thee HPV-16 E5 gene enhances protein expression," *Virology*, 311:105-114, 2003.
Donnelly et al., "Technical and regulatory hurdles for DNA vaccines," *Int J Parasitol*, 33(5-6):457-467, 2003.
Dunham, "The application of nucleic acid vaccines in veterinary medicine," *Res Vet Sci.*, 73(1):9-16, 2002.
Duret et al., "Expression pattern and, surprisingly, gene length shape codon usage in Caenorhabditis, *Drosophila*, and *Arabidopsis*," *Proc. Nat. Acad. Sci. USA*, 96:4482-4487, 1999.
Duret, "Evolution of synonymous codon usage in metazoans," *Current Opinion in Genetics & Development*, 12:640-648, 2002.
Edelstein et al., "Gene therapy clinical trials worldwide 1989-2004—an overview," *J Gene Med.*, 6(6):597-602, 2004.
Egeter et al., "Eradication of Disseminated Lymphomas with CpG-DNA Activated T Helper Type 1 Cells from Nontransgenic Mice," *Cancer Research*, 60(6):1515-1520, 2000.
Elbashir et al., "Duplexes of 21-nucleotide RNAs mediate RNA interference in cultured mammalian cells," *Nature*, 411(6836):494-498, 2001.
Fang et al., "Functional Measurement of Hepatitis C Vitus Core-Specific CD8+ T-Cell Responses in the Livers or Peripheral Blood of Patients by Using Autologous Peripheral Blood Mononuclear Cells as Targets or Stimulators," *Journal of Clinical Microbiology*, 39(11):3985-3901, 2001.
Fearnley et al., "Monitoring human blood dendritic cell numbers in normal individuals and in stem cell transplantation," *Blood*, 93(2):728-736, 1999.
Fisch et al., "Generation of antigen-presenting cells for soluble protein antigens ex vivo from peripheral blood CD34+ hematopoietic progenitor cells in cancer patients," *Eur J Immunol.*, 26(3):595-600, 1996.
Fisk et al., "Identification of an immunodominant peptide of HER-2/neu protooncogene recognized by ovarian tumor-specific cytotoxic T lymphocyte lines," *J Exp Med*, 181(6):2109-2117, 1995.
Ford et al., "The poly(A) tail inhibits the assembly of a 3'-to5' exonuclease in an in vitro RNA stability system," *Molecular and Cellular Biology*, 17(1):398-406, 1997.
Fynan et al., "DNA vaccines: protective immunization by parental, mucosal, and gene-gun inoculations," *Proc Natl Acad Sci USA*, 90(24):11478-11482, 1993.
Gao et al., "Nonviral gene delivery: what we know and what is next," *AAPS J*, 9(1):E92-E104, 2007.
Garbe et al., "[Epidemiology of malignant melanoma in West Germany in an international comparison]," Onkologie 12(6): 253-62, 1989. [Article in German].
Gardiner-Garden et al., "CpG islands in vertebrate genomes," *J. Mol. Biol.*, 196:261-282, 1987.
GenBank Accession No. AF125673, GI: 4927719, Jun. 2000.
GenBank Accession No. X65300, "Cloning vector pGEM-1," 1999.
GenBank Accession No. X65327, "Cloning vector pSP64," 1999.

(56) References Cited

OTHER PUBLICATIONS

Gilkeson et al., "Induction of cross-reactive anti-dsDNA antibodies in preautoimmune NZB/NZW mice by immunization with bacterial DNA," *J Clin Invest*, 95(3):1398-1402, 1995.
Grabbe et al., "Dendritic cells as initiators of tumor immune responses: a possible strategy for tumor immunotherapy," *Immunol Today*, 16(3):117-121, 1995.
Grabbe et al., "Tumor antigen presentation by epidermal antigen-presenting cells in the mouse: modulation by granulocyte-macrophage colony-stimulating factor, tumor necrosis factor-alpha, and ultraviolet radiation," *J Leukoc Biol*, 52(2):209-217, 1992.
Grabbe et al., "Tumor antigen presentation by murine epidermal cells," *J Immunol*, 146(10):3656-3661, 1991.
Graham et al., "Intramuscular immunization with MUC1 cDNA can protect C57 mice challenged with MUC1-expressing syngeneic mouse tumor cells," *International Journal of Cancer*, 65:664-667, 1996.
Gram et al., "Immunological analysis of a Lactococcus lactis-based DNA vaccine expressing HIV gp120," *Genetic Vaccine and Therapy*, 5(3):Jan. 11-Nov. 11, 2007.
Granstein et al., "Induction of anti-tumor immunity with epidermal cells pulsed with tumor-derived RNA or intradermal administration of RNA," *J Invest Dermatol.*, 114(4):632-636, 2000.
Gryanznov, "Oligonucleotide N3'->P5' phosphoramidates as potential therapeutic agents," *Biochim Biophys Acta.*, 1489(1):131-140, 1999.
Haas et al., "Codon usage limitation in the expression of HIV-1 envelope glycoprotein," *Current Biology*, 6(3):315-324, 1996.
Heidenreich et al., "Chemically modified RNA: approaches and applications," *FASEB Journal*, 7(1):90-96, 1993.
Heil et al., "Species-specific recognition of single-stranded RNA via toll-like receptor 7 and 8," *Science*, 303(5663):1526-1529, 2004.
Heiser et al., "Autologous dendritic cells transfected with prostate-specific antigen RNA stimulate CTL responses against metastatic prostate tumors," *Journal of Clinical Investigation*, 109(3):409-417, 2002.
Heiser et al., "Human dendritic cells transfected with renal tumor RNA stimulate polyclonal T-cell responses against antigens expressed by primary and metastatic tumors," *Cancer Research*, 61(8):3388-3393, 2001.
Heiser et al., "Human dendritic cells transfected with RNA encoding prostate-specific antigen stimulate prostate-specific CTL responses in vitro," *Journal of Immunology*, 164(10):5508-5514, 2000.
Heiser et.al., "Induction of polyclonal prostate cancer-specific CTL using dendritic dells transfected with amplified tumor RNA," *J. Immunol.*, 166(5):2953-2960, 2001.
Hemmi et al., "A toll-like receptor recoginzes bacterial DNA," *Nature*, 408:740-745, 2000.
Herweijer et al., "Gene therapy progress and prospects: Hydrodynamic gene delivery," *Gene Ther.*, 14(2):99-107, 2007.
Hilleren et al., "Mechanisms of mRNA surveillance in eukaryotes," *Annu Rev Genet.*, 3:229-260, 1999.
Hirasawa, "Natural autoantibody to MUC1 is a prognostic indicator for non-small cell lung cancer," *American Journal of Respiratory and Critical Care Medicine*, 161:589-594, 2000.
Hoath et al., "The Organization of Human Epidermis: Functional Epidermal Units and Phi Proportionality," *J. Invest. Dermatol.*, 121:1440-1446, 2003.
Hoerr et al., "In vivo application of RNA leads to induction of specific cytotoxic T lymphocytes and antibodies," *Eur. J. Immunol.*, 30(1):1-7, 2000.
Holcik et al., "Four highly stable eukaryotic mRNAs assemble 3' untranslated region RNA-protein complexes sharing cis and trans components," *Proc Natl Acad Sci USA*, 94(6):2410-2414, 1997.
Holmes and Morgan, "Cell positioning and sorting using dielectrophoresis," *European Cells and Materials*, 4(Suppl. 2):120-122, 2002.
Houghton et al., "Cancer antigens: immune recognition of self and altered self," *J Exp Med*, 180(1):1-4, 1994.

Hsu et al., "Vaccination of patients with B-cell lymphoma using autologous antigen-pulsed dendritic cells," *Nat Med*, 2(1):52-58, 1996.
Huddleston et al., "The sequence of the nucleoprotein gene of human influenza A virus, strain a/NT/60/68," *Nucleic Acids Research*, 10(3):1029-1038, 1982.
Inaba et al., "Dendritic cells pulsed with protein antigens in vitro can prime antigen-specific, MHC-restricted T cells in situ," *J Exp Med*, 172(2):631-640, 1990.
Inaba et al., "Direct activation of CD8+ cytotoxic T lymphocytes by dendritic cells," *J Exp Med*, 166(1):182-194, 1987.
Iwasaki et al., "Enhanced CTL responses mediated by plasmid DNA immunogens encoding costimulatory molecules and cytokines," *J Immunol.*, 158(10:4591-4601, 1997.
Janeway et al., Immunobiology, The Immune System in Health and Disease, 13:12-13:21, 1997.
Janssens et al., "Role of Toll-Like Receptors in Pathogen Recognition," *Clinical Microbiology Reviews*, 16(4):637-646, 2003.
Januszyk and Lima, "Structural components and architectures of RNA exosomes," in: Madame Curie Bioscience Database, Landes Bioscience, downloaded at http://www.ncbi.nlm.nih.gov/books/NBK45033/, 22 pages, 2000.
Kabanov et al., "A new class of antivirals: antisense oligonucleotides combined with a hydrophobic substituent effectively inhibit influenza virus reproduction and synthesis of virus-specific proteins in MDCK cells," *FEBS Lett*, 259(2): 327-330, 1990.
Kallen et al., "A development that may evolve into a revolution in medicine: mRNA as the basis for novel, nucleotide-based vaccines and drugs," *Therapeutic Advances in Vaccines*, 2(1):10-31, 2013.
Kallen et al., "A novel, disruptive vaccination technology: self-adjuvanted RNActive vaccines," *Human Vaccines & Immunotherapeutics*, 9(10):16-29, 2013.
Kalnins et al., "Sequence of the lacZ gene of *Escherichia coli*," *EMBO J.*, 2(4): 593-597, 1983.
Kanaya et al., "Codon usage and tRNA genes in eukaryotes: correlation of codon usage diversity with translation efficiency and with CG-dinucleotide usage as assessed by multivariate analysis," *J Mol Evol*, 53:290-298, 2001.
Kandimalla et al., "Divergent synthetic nucleotide motif recognition pattern: design and development of potent immunomodulatory oligodeoxyribonucleotide agents with distinct cytokine induction profiles," *Nucleic Acids Research*, 31(9):2393-2400, 2003.
Kandimallia et al., "Immunomodulatory oligonucteotides containing a cytosine-phosphate-2'-deoxy-7-deazaguanosine motif as potent toll-like receptor 9 agonists," *PNAS*, 102(19):6925-6930, 2005.
Kariko et al., "Naturally occurring nucleoside modifications suppress the immunostimulatory activity of RNA: implication for therapeutic RNA development," *Curr. Opin. Drug Discov. Devel.*, 10(5):523-532, 2007.
Kariko et al., "Suppression of RNA Recognition by Toll-like Receptors: The Impact of Nucleoside Modification and the Evolutionary Origin of RNA," *Immunity*, 23:165-175, 2005.
Karlin et al., "Applications and statistics for multiple high-scoring segments in molecular sequences," *Proc Natl Acad Sci USA*, 90(12):5873-5877, 1993.
Kim et al., "Codon optimization for high-level expression of human erythropoietin (EPO) in mammalian cells," *Gene*, 199:293-301, 1997.
Klinmann et al., "DNA vaccines safety and efficacy issues," *Springer Semin Immunopathol*, 19(2):245-256, 1997.
Kohler et al., "Continuous cultures of fused cells secreting antibody of predefined specificity," *Nature*, 256(5517):495-497, 1975.
Koide et al., "DNA Vaccines," *Jpn J. Pharmacol.*, 83(3):167-174, 2000.
Koido et al., "Induction of antitumor immunity by vaccination of dendritic cells transfected with MUC1 RNA," *J Immunol*, 165(10:5713-5719, 2000.
Komar et al., "Synonymous codon substitutions affect ribosome traffic and protein folding during in vitro translation," *FEBS Letters*, 462:387-391, 1999.
Kontermann, "Recombinant bispecific antibodies for cancer therapy," *Acta Pharmacol Sin*, 26(1):1-9, 2005.

(56) References Cited

OTHER PUBLICATIONS

Krieg et al., "In vitro RNA synthesis with SP6 RNA polymerase," *Methods Enzymol*, 155:397-415, 1987.
Kudla et al., "High Guanine and Cytosine Content Increases mRNA Levels in Mammalian Cells," *PLoS Biol*, 4(6):e180, 2006.
Kufe et al., Cancer Medicine, 6th edition, Table 12-1, 2003.
Kugler et al., "Regression of human metastatic renal cell carcinoma after vaccination with tumor cell-dendritic cell hybrids," *Nat Med*, 6(3):332-336, 2000.
Kundu and Rao, "CpG islands in chromatin organization and gene expression," *J. Biochem.*, 125:217-222, 1999.
Kusakabe et al., "The timing of GM-CSF expression plasmid administration influences the Th1/Th2 response induced by an HIV-1 specific DNA vaccine," *J Immunol*, 164(6):3102-3111, 2000.
Kwissa et al., "Cytokine-facilitated priming of CD8+ T cell responses by DNA vaccination," *J Mol Med*, 81(2):91-101, 2003.
Lai et al., "Patterning of the neural ectoderm of Xenopus laevis by the amino-terminal product of hedgehog autoproteolytic cleavage," *Development*, 121(8):2349-2360, 1995.
Larregina et al., "Changing Paradigms in Cutaneous Immunology: Adapting with Dendritic Cells," *The Journal of Investigative Dermatology*, 124(1):1-12, 2005.
Lathe, "Synthetic oligonucleotide probes deduced from amino acid sequence data. Theoretical and practical considerations," *Journal of Molecular Biology*, 183(1):1-12, 1985.
Lee et al., "Molecular basis for the immunostimulatory activity of guanine nucleoside analogs: Activation of Toll-like receptor 7," *PNAS*, 100(11):6646-6651, 2003.
Leitner et al., "DNA and RNA-based vaccines: principles, progress and prospects," *Vaccine*, 18(9-10):765-777, 2000.
Lenz et al., "Human and murine dermis contain dendritic cells. Isolation by means of a novel method and phenotypical and functional characterization," *Journal of Clinical Investigation*, 92:2587-2596, 1993.
Linehan et al., "Tumor-specific and HLA-A2-restricted cytolysis by tumor-associated lymphocytes in human metastatic breast cancer," *J Immunol*, 155(9):4486-4491, 1995.
Loging et al., "Identifying potential tumor markers and antigens by database mining and rapid expression screening," *Genome Res.*, 10:1393-1402, 2000.
Lopez-Ferrer et al., "Mucins as differentiation markers in bronchial epithelium," *American Journal of Respiratory Cell and Molecular Biology*, 24(1):22-29, 2001.
Luo et al., "Synthetic DNA delivery systems," *Nat Biotechnol.*, 18(1):33-37, 2000.
Martinon et al., "Induction of virus-specific cytotoxic T lymphocytes in vivo by liposome-entrapped mRNA," *Eur J Immunol.*, 23(7):1719-1722, 1993.
Mathers et al., "Professional antigen-presenting cells of the skin," *Immunol. Res.*, 36(1-3):127-136, 2006.
Matray et al., "Synthesis and properties of RNA analogs—oligoribonucleotide N3' → P5' phosphoramidates," *Nucleic Acids Research*, 27(20):3976-3985, 1999.
McCafferty et al., "Phage antibodies: filamentous phage displaying antibody variable domains," *Nature*, 348(6301):552-554, 1990.
McKenzie et al., "Nucleic acid vaccines: tasks and tactics," *Immunologic Research*, 24(3):225-244, 2001.
Meunier et al., "Heterogeneous populations of class II MHC+ cells in human dermal cell suspensions. Identification of a small subset responsible for potent dermal antigen-presenting cell activity with features analogous to Langerhans cells," *The Journal of Immunology*, 151(8):4067-4080, 1993.
Minks et al., "Structural Requirements of Double-stranded RNA for the Activation of 2',5'-oligo(A) Polymerase and Protein Kinase of Interferon-treated HeLa Cells," *The Journal of Biological Chemistry*, 254(20):10180-10183, 1979.
Mishra et al., "Improved leishmanicidal effect of phosphorotioate antisense oligonucleolides by LDL-mediated delivery," *Biochim Biophys Acta*, 1264(2):229-237, 1995.
Mitchell et al., "mRNA turnover," *Curr Opin Cell Biol.*, 13(3):320-325, 2001.
Mitchell et al., "RNA transfected dendritic cells as cancer vaccines," *Curr. Opin. Mol. Ther.*, 2(2):176-181, 2000.
Mitchell et al., "RNA-transfected dendritic cells in cancer immunotherapy," *J Clin Invest*, 106(9):1065-1069, 2000.
Morinaga et al., "Primary structures of human a-fetoprotein and its mRNA," *Proc. Natl. Acad. Sci. USA*, 80:4604-4608, 1983.
Morse et al., "Generation of dendritic cells in vitro from peripheral blood mononuclear cells with granulocyte-macrophage-colony-stimulating factor, interleukin-4, and tumor necrosis factor-alpha for use in cancer immunotherapy," *Annals of Surgery*, 226:6-16, 1997.
Müller et al., "Transfection of dendritic cells with RNA induces CD4- and CD8-mediated T cell immunity against breast carcinomas and reveals the immunodominance of presented T cell epitopes," *J Immunol*, 170(12):5892-5896, 2003.
Nagata et al., "Codon optimization effect of translational efficiency of DNA vaccine in mammalian cells: analysis of plasmid DNA encoding a CTL epitope derived from microorganisms," *Biochemical and Biophysical Research Communications*, 261:445-451, 1999.
Nair et al., "Antigen-presenting cells pulsed with unfractionated tumor-derived peptides are potent tumor vaccines," *Eur J Immunol*, 27(3):589-597, 1997.
Nair et al., "Induction of cytotoxic T cell responses and tumor immunity against unrelated tumors using telomerase reverse transcriptase RNA transfected dendritic cells," *Nat Med*, 6(9):1011-1017, 2000.
Nair et al., "Induction of primary carcinoembryonic antigen (CEA)-specific cytotoxic T lymphocytes in vitro using human dendritic cells transfected with RNA," *Nat Biotechnol*, 16(4):364-369, 1998.
Nair et al., "Soluble proteins delivered to dendritic cells via pH-sensitive liposomes induce primary cytotoxic T lymphocyte responses in vitro," *J Exp Med*, 175(2):609-612, 1992.
Nestle et al., "Vaccination of melanoma patients with peptide-or tumor lysate-pulsed dendritic cells," *Nat Med*, 4(3):328-332, 1998.
Nicholson et al., "Accurate in vitro cleavage by RNase III of phosphorothioate-substituted RNA processing signals in bacteriophage T7 early mRNA," *Nucleic Acids Research*, 16(4):1577-1591, 1988.
O'Doherty et al., "Human blood contains two subsets of dendritic cells, one immunologically mature and the other inmature," *Immunology*, 82:487-493, 1994.
Oberhauser et al., "Effective incorporation of 2'-O-methyl-oligoribonucleotides into liposomes and enhanced cell association through modification with thiocholesterol," *Nucleic Acids Res*, 20(3):533-538, 1992.
Paglia et al., "Murine dendritic cells loaded in vitro with soluble protein prime cytotoxic T lymphocytes against tumor antigen in vivo," *J Exp Med*, 183(1):317-322, 1996.
Palu et al., "In pursuit of new developments for gene therapy of human diseases," *J. Biotechnol.*, 68(1):1-13, 1999.
Palucka et al., "Taming cancer by inducing immunity via dendritic cells," *Immunological Reviews*, 220:129-150, 2007.
PCT International Search Report and Written Opinion issued in International Application No. PCT/EP2014/002931, dated Mar. 23, 2015.
Peoples et al., "Breast and ovarian cancer-specific cytotoxic T lymphocytes recognize the same HER2/neu-derived peptide," *Proc Natl Acad Sci USA*, 92(2):432-436, 1995.
Pesole et al., "UTRdb and UTRsite: specialized databases of sequences and functional elements of 5' and 3' untranslated regions of eukaryotic mRNAs," *Nucleic Acids Res.*, 30(1):335-340, 2002.
Ponsaerts et al., "Cancer immunotherapy using RNA-loaded dendritic cells," *Clinical and Experimental Immunology*, 134:378-384, 2003.
Porgador et al., "Bone marrow-generated dendritic cells pulsed with a class I-restricted peptide are potent inducers of cytotoxic T lymphocytes," *J Exp Med*, 182(1):255-260, 1995.
Porgador et al., "Induction of antitumor immunity using bone marrow-generated dendritic cells," *J Immunol.*, 156(8):2918-2926, 1996.
Rajagopalan et al., "Turnover and Translation of in Vitro Synthesized Messenger RNAs in Transfected, Normal Cells," *The Journal of Biological Chemistry*, 271(33):19871-19876, 1996.

(56) References Cited

OTHER PUBLICATIONS

Ramazeilles et al., "Antisense phosphorothioate oligonucleotides: selective killing of the intracellular parasite Leishmania amazonensis," *Proc. Natl. Acad. Sci. USA*, 91:7859-7863, 1994.
Rammensee et al., "Peptides naturally presented by MHC class I molecules," *Annu Rev Immunol*, 11:213-244, 1993.
Renkvist et al., "A listing of human tumor antigens recognized by T cells," *Cancer Immunol Immunother.*, 50:3-13, 2001.
Reyes-Sandoval et al., "DNA vaccines," *Current Molecular Medicine*, 1:217-243, 2001.
Robbins et al., "Human tumor antigens recognized by T cells," *Curr Opin Immunol*, 8(5):628-636, 1996.
Robinson et al., "Expression of Human nPTB is Limited by Extreme Suboptimal Codon Content," *PLoS One*, 3(3):e1801, 2008.
Robinson et al., "Protection against a lethal influenza virus challenge by immunization with a haemagglutinin-expressing plasmid DNA," *Vaccine*, 11(9):957-960, 1993.
Rock, "A new foreign policy: MHC class I molecules monitor the outside world," *Immunol Today*, 17(3):131-137, 1996.
Roitt et al., *Immunology*, 4$^{th}$ Edition. Barcelona: Times Mirror International Publishers Limited, p. 1.7, 1996.
Romani et al., "Generation of mature dendritic cells from human blood. An improved method with special regard to clinical applicability," *Journal of Immunological Methods*, 196:137-151, 1996.
Romani et al., "Presentation of exogenous protein antigens by dendritic cells to T cell clones. Intact protein is presented best by immature, epidermal Langerhans cells," *J Exp Med*, 169(3):1169-1178, 1989.
Rosenberg et al., "Cancer immunotherapy: moving beyond current vaccines," *Nat. Med*, 10(9):909-915, 2004.
Ross et al., "Control of messenger RNA stability in higher eukaryotes," *Trends Genet.*, 12(5):171-175, 1996.
Saenz-Badillos et al., "RNA as a tumor vaccine: a review of the literature," *Exp. Dermatol.*, 10(3):143-154, 2001.
Saison-Behmoaras et al., "Short modified antisense oligonucleotides directed against Ha-ras point mutation induce selective cleavage of the mRNA and inhibit T24 cells proliferation," *Embo J*, 10(5):1111-1118, 1991.
Sakatsume et al., "Inhibitory effect of oligoribonucleotide phosphorodithioates against the 3'-exonuclease activity," *Nucleic Acids Symposium Series*, 27:195-196, 1992.
Sallusto et al., "Dendritic cells use micropinocytosis and the mannose receptor to concentrate macromolecules in the major histocompatibility complex class II compartment: downregulation by cytokines and bacterial products," *J Exp Med*, 182(2):389-400, 1995.
Sallusto et al., "Efficient presentation of soluble antigen by cultured human dendritic cells is maintained by granulocyte/macrophage colony-stimulating factor plus interleukin 4 and downregulated by tumor necrosis factor alpha," *Journal of Experimental Medicine*, 179(4):1109-1118, 1994.
Sattthaporn et al., "Dendritic cells (II): Role and therapeutic implications in cancer," *J.R. Coll. Surg. Edinb.*, 46(3):159-167, 2001.
Scheel et al., "Immunostimulating capacities of stabilized RNA molecules," *Eur J Immunol*, 34(2):537-547, 2004.
Schirmacher et al., "Intra-pinna anti-tumor vaccination with self-replicating infectious RNA or with DNA encoding a model tumor antigen and a cytokine," *Gene Therapy*, 7(13):1137-1147, 2000.
Schlake et al., "Developing mRNA-vaccine technologies," *RNA Biology*, 9(11):1319-1330, 2012.
Schmitt et al., "In vitro induction of a bladder cancer-specific T-cell response by mRNA-transfected dendritic cells," *J Cancer Res Clin Oncol*, 127(3):203-206, 2001.
Schuler et al., "Murine epidermal Langerhans cells mature into potent immunostimulatory dendritic cells in vitro," *J Exp Med*, 161(3):526-546, 1985.
Schuler-Thurner et al., "Mage-3 and influenza-matric peptide-specific cytotoxic T cells are inducible in terminal stage HLA-A2 1+ melanoma patients by mature monocyte-derived dendritic cells," *J Immunol.*, 165(6):3492-3496, 2000.

Sharp et al., "DNA sequence evolution: the sounds of silence," *Phil. Trans. R. Soc. Lond. B*, 349:241-247, 1995.
Shea et al., "Synthesis, hybridization properties and antiviral activity of lipid-oligodeoxynucleotide conjugates," *Nucleic Acids Res*, 18(13):3777-3783, 1990.
Siena et al., "Expansion of Immunostimulatory Dendritic Cells from Peripheral Blood of Patients with Cancer," *The Oncologist*, 2:65-69, 1997.
Sousa, "Use of T7 RNA Polymerase and Its Mutants for Incorporation of Nucleoside Analogs into RNA," *Methods in Enzymology*, 317:65-74, 2000.
Steinman et al., "Dendritic cells: antigen presentation, accessory function and clinical relevance," *Adv Exp Med Biol*, 329:1-9, 1993.
Steinman, "The dendritic cell system and its role in immunogenicity," *Annu Rev Immunol.*, 9:271-296, 1991.
Sterner and Berger, "Acetylation of histones and transcription-related factors," *Microbiology and Molecular Biology Reviews*, 64(2):435-459, 2000.
Stinchcomb et al., "Isolation and characterisation of a yeast chromosomal replicator," *Nature*, 282(5734): 39-43, 1979.
Strong et al., "Incorporation of β-globin untranslated regions into Sindbis virus vector for augmentation of heterologous mRNA expression," *Gene Therapy*, 624-627, 1997.
Su et al., "Enhanced induction of telomerase-specific CD4(+) T cells using dendritic cells transfected with RNA encoding a chimeric gene product," *Cancer Research*, 62:5041-5048, 2002.
Su et al., "Immunological and Clinical Responses in Metastatic Renal Cancer Patients Vaccinated with Tumor RNA-transfected Dendritic Cells," *Cancer Research*, 63:2127-2133, 2003.
Suda et al., "Hydrodynamic gene delivery: its principles and applications," *Mol. Ther.*, 15(12):2063-2069, 2007.
Sullenger et al., "Emerging clinical applications of RNA," *Nature*, 418(6894):252-258, 2002.
Svinarchuk et al., "Inhibition of HIV proliferation in MT-4 cells by antisense oligonucleotide conjugated to lipophilic groups," *Biochimie*, 75(1-2):49-54, 1993.
Tang et al., "Genetic immunization is a simple method for eliciting an immune response," *Nature*, 356(6365):152-154, 1992.
Tazi and Bird, "Alternative chromatin structure at CpG islands," *Cell*, 60:909-920, 1990.
Teufel et al., "Human peripheral blood mononuclear cells transfected with messenger RNA stimulate antigen-specific cytotoxic T-lymphocytes in vitro," *Cell. Mol. Life Sci.*, 62:1755-1762, 2005.
Thurner et al., "Vaccination with mage-3A1 peptide-pulsed mature, monocyte-derived dendritic cells expands specific cytotoxic T cells and induces regression of some metastases in advanced stage IV melanoma," *J Exp Med*, 190(11):1669-1678, 1999.
Tourriere et al., "mRNA degradation machines in eukaryotic cells," *Biochimie*, 84(8):821-837, 2002.
Trinchieri et al., "Cooperation of Toll-like receptor signals in innate immune defence," *Nature Reviews Immunology*, 7:179-190, 2007.
Trojan et al., "Immune reactivity against a novel HLA-A3-restricted influenza virus peptide identified by predicative algorithms and interferon-gamma quantitative PCR," *Journal of Immunotherapy*, 26(1):41-46, 2003.
Tüting et al., "Gene-based strategies for the immunotherapy of cancer," *J Mol Med*, 75:478-491, 1997.
Ueda et al., "Phosphorothioate-containing RNAs show mRNA activity in the prokaryotic translation systems in vitro," *Nucleic Acids Res.*, 19(3):547-552, 1991.
Ulmer et al., "Heterologous protection against influenza by injection of DNA encoding a viral protein," *Science*, 259(5102):1745-1749, 1993.
Ulmer, "An update on the state of the art of DNA vaccines," *Curr Opin Drug Discov Devel*, 4(2):192-197, 2001.
Vassilev et al., "Microparticle-mediated RNA immunization against bovine viral diarrhea virus," *Vaccine*, 19(15-1 6):2012-2019, 2001.
Verma et al., "Gene therapy—promises, problems and prospects," *Nature*, 389(6648):239-242, 1997.
Verma et al., "Gene therapy: twenty-first century medicine," *Annu. Rev. Biochem.*, 74:711-738, 2005.

(56) References Cited

OTHER PUBLICATIONS

Villaret et al., "Identification of genes overexpressed in head and neck squamous cell carcinoma using a combination of complementary DNA subtraction and microarray analysis," *The Laryngoscope*, 110: 374-381, 2000.
Wang et al., "Gene inoculation generates immune responses against human immunodeficiency virus type 1," *Proc Natl Acad Sci USA*, 90(9):4156-4160, 1993.
Warren et al., "Uses of granulocyte-macrophage colony-stimulating factor in vaccine development," *Curr Opin Hematol*, 7(3):168-173, 2000.
Watanabe et al., "Induction of wild-type p53 activity in human cancer cells by ribozymes that repair mutant p53 transcripts," *PNAS*, 97(15):8490-8494, 2000.
Weber et al., "Granulocyte-macrophage-colony-stimulating factor added to a multipeptide vaccine for resected Stage II melanoma," *Cancer*, 97(1):186-200, 2003.
Weide et al., "Results of the First Phase I/II Clinical Vaccination Trial with Direct Injection of mRNA," *J. Immunother.*, 31(2):180-188, 2008.
Weissman et al., "HIV gag mRNA transfection of dendritic cells (DC) delivers encoded antigen to MHC class I and II molecules, causes DC maturation, and induces a potent human in vitro primary immune response," *J. Immunol.*, 165(8):4710-4717, 2000.
Weissmann et al., "Dendritic cells express and use multiple HIV coreceptors," *Adv Exp Med Biol*, 417:401-406, 1997.
Wikipedia Diagram, "A peripheral blood mononuclear cell," 2011.
Wilusz et al., "Bringing the role of mRNA decay in the control of gene expression into focus," *Trends Genet.*, 20(10):491-497, 2004.
Wolff et al., "Direct gene transfer into mouse muscle in vivo," *Science*, 247(4949 Pt. 1):1465-1468, 1990.
Woodberry et al., "Immunogenicity of a human immunodeficiency virus (HIV) polytope vaccine containing multiple HLA A2 HIV CD8(+) cytotoxic T-cells epitopes," *Journal of Virology*, 73(7):5320-5325, 1999.
Wu et al., "Fusion protein vectors to increase protein production and evaluate the immunogenicity of genetic vaccines," *Mol. Ther.*, 2(3):288-297, 2000.
Xu et al., "Identification of differentially expressed genes in human prostate cancer using subtraction and microarray," *Cancer Research*, 60:1677-1682, 2000.
Ying et al., "Cancer therapy using a self-replicating RNA vaccine," *Nat Med*, 5(7):823-827, 1999.
You et al., "A retrogen strategy for presentation of an intracellular tumor antigen as an exogenous antigen by dendritic cells induces potent antitumor T helper and CTL responses," *Cancer Research*, 61:197-205, 2001.
Zhang et al., "Advances in dendritic cell-based vaccine of cancer," *Cancer Biotherapy & Radiopharmaceuticals*, 17:601-619, 2002.
Zhou et al., "Papillomavirus capsid protein expression level depends on the match between codon usage and tRNA availability," *Journal of Virology*, 73(6):4972-4982, 1999.
Zhou et al., "RNA melanoma vaccine: induction of antitumor immunity by human glycoprotein 100 mRNA immunization," *Human Gene Therapy*, 10:2719-2724, 1999.
Zitvogel et al., "Therapy of murine tumors with tumor peptide-pulsed dendritic cells: dependence on T cells, B7 costimulation, and T helper cell 1-associated cytokins," *J Exp Med*, 183(1):87-97, 1996.
Zrihan-Licht et al., "Characterization and molecular cloning of a novel MUC1 protein devoid of tandem repeats, expressed in human breast cancer tissue," *European Journal of Biochemistry*, 224:787-795, 1994.
Galiger et al., "Assessment of Efficacy of Antifungals against Aspergillus fumigatus: Value of Real-time Bioluminescence Imaging", *Antimicrob. Agents Chemother.*, 57(7):3046-3059, 2013.
Wei et al., "The Stringency of Start Codon Selection in the Filamentous Fungus *Neurospora crassa*", *J. Biol. Chem.*, 288(13):9549-9562, 2013..
Annex to Ngumbela et al., "Quantitative Effect of Suboptimal Codon Usage on Translational Efficiency of mRNA Encoding HIV-1 gag in Intact T Cells", *PLoS One*, 3(6):1-5, 2008.
Ngumbela et al., "Quantitative Effect of Suboptimal Codon Usage on Translational Efficiency of mRNA Encoding HIV-1 gag in Intact T Cells", *PLoS One*, 3(6):1-5, 2008.
Third Party Observation regarding EP Patent Application No. 14809289.3-1118, submitted Jan. 2, 2020.

\* cited by examiner

R873

GGGAGAUGUACAAAGCUUACCAUGGAAGACGCCAAAAACAUAAAGAAAGGCCCGGCGCCA
UUCUAUCCGCUGGAAGAUGGAACCGCUGGAGAGCAACUGCAUAAGGCUAUGAAGAGAUAC
GCCCUGGUUCCUGGAACAAUUGCUUUUACAGAUGCACAUAUCGAGGUGGACAUCACUUAC
GCUGAGUACUUCGAAAUGUCCGUUCGGUUGGCAGAAGCUAUGAAACGAUAUGGGCUGAAU
ACAAAUCACAGAAUCGUCGUAUGCAGUGAAAACUCUCUUCAAUUCUUUAUGCCGGUGUUG
GGCGCGUUAUUUAUCGGAGUUGCAGUUGCGCCCGCGAACGACAUUUAUAAUGAACGUGAA
UUGCUCAACAGUAUGGGCAUUUCGCAGCCUACCGUGGUGUUCGUUUCCAAAAAGGGGUUG
CAAAAAUUUUGAACGUGCAAAAAAGCUCCCAAUCAUCCAAAAAUUAUUAUCAUGGAU
UCUAAAACGGAUUACCAGGGAUUUCAGUCGAUGUACACGUUCGUCACAUCUCAUCUACCU
CCCGGUUUUAAUGAAUACGAUUUUGUGCCAGAGUCCUUCGAUAGGGACAAGACAAUUGCA
CUGAUCAUGAACUCCUCUGGAUCUACUGGUCUGCCUAAAGGUGUCGCUCUGCCUCAUAGA
ACUGCCUGCGUGAGAUUCUCGCAUGCCAGAGAUCCUAUUUUUGGCAAUCAAAUCAUUCCG
GAUACUGCGAUUUUAAGUGUUGUUCCAUUCCAUCACGGUUUUGGAAUGUUUACUACACUC
GGAUAUUUGAUAUGUGGAUUUCGAGUCGUCUUAAUGUAUAGAUUUGAAGAAGAGCUGUUU
CUGAGGAGCCUUCAGGAUUACAAGAUUCAAAGUGCGCUGCUGGUGCCAACCCUAUUCUCC
UUCUUCGCCAAAAGCACUCUGAUUGACAAAUACGAUUUAUCUAAUUUACACGAAAUUGCU
UCUGGUGGCGCUCCCCUCUCUAAGGAAGUCGGGGAAGCGGUUGCCAAGAGGUUCCAUCUG
CCAGGUAUCAGGCAAGGAUAUGGGCUCACUGAGACUACAUCAGCUAUUCUGAUUACACCC
GAGGGGGAUGAUAAACCGGGCGCGGUCGGUAAAGUUGUUCCAUUUUUUGAAGCGAAGGUU
GUGGAUCUGGAUACCGGGAAAACGCUGGGCGUUAAUCAAAGAGGCGAACUGUGUGUGAGA
GGUCCUAUGAUUAUGUCCGGUUAUGUAAACAAUCCGGAAGCGACCAACGCCUUGAUUGAC
AAGGAUGGAUGGCUACAUUCUGGAGACAUAGCUUACUGGGACGAAGACGAACACUUCUUC
AUCGUUGACCGCCUGAAGUCUCUGAUUAAGUACAAAGGCUAUCAGGUGGCUCCCGCUGAA
UUGGAAUCCAUCUUGCUCCAACACCCCAACAUCUUCGACGCAGGUGUCGCAGGUCUUCCC
GACGAUGACGCCGGUGAACUUCCGCCGCCGUUGUUGUUUGGAGCACGGAAAGACGAUG
ACGGAAAAAGAGAUCGUGGAUUACGUCGCCAGUCAAGUAACAACCGCGAAAAGUUGCGC
GGAGGAGUUGUGUUUGUGGACGAAGUACCGAAAGGUCUUACCGGAAAACUCGACGCAAGA
AAAAUCAGAGAGAUCCUCAUAAAGGCCAAGAAGGGCGGAAAGAUCGCCGUGUAACCUCUA
GUAGAUCUAAAAAAAAAAAAAAAAAAAAAAAAAAAAAAAAAAAAAAAAAAAAAAAAAAAA
AAAAAAAAAAAAAAAAA

GGGAGAUGUACAAAGCUUACCAUGGAGGACGCCAAGAACAUCAAGAAGGGCCCCGCCCCG
UUCUACCCCCUGGAGGACGGGACCGCGGGCGAGCAGCUCCACAAGGCCAUGAAGCGGUAC
GCCCUGGUGCCCGGGACCAUCGCCUUCACGGACGCCCACAUCGAGGUCGACAUCACCUAC
GCGGAGUACUUCGAGAUGAGCGUGCGCCUGGCCGAGGCCAUGAAGCGGUACGGCCUCAAC
ACCAACCACCGCAUCGUGGUCUGCUCCGAGAACAGCCUGCAGUUCUUCAUGCCCGUGCUG
GGGGCCCUCUUCAUCGGCGUGGCGGUCGCCCCGGCCAACGACAUCUACAACGAGCGGGAG
CUGCUGAACUCCAUGGGCAUCAGCCAGCCCACCGUGGUGUUCGUCUCCAAGAAGGGGCUC
CAGAAGAUCCUGAACGUGCAGAAGAAGCUGCCGAUCAUCCAGAAGAUCAUCAUCAUGGAC
AGCAAGACGGACUACCAGGGCUUCCAGUCCAUGUAUACCUUCGUGACCAGCCACCUCCCC
CCGGGGUUCAACGAGUACGACUUCGUCCCCGAGUCCUUCGACCGCGACAAGACCAUCGCC
CUGAUCAUGAACAGCUCCGGCAGCACGGGGCUGCCCAAGGGCGUGGCCCUCCCCCACCGG
ACCGCGUGCGUGCGCUUCUCCCACGCCCGGGACCCGAUCUUCGGCAACCAGAUCAUCCCC
GACACCGCCAUCCUGAGCGUCGUGCCCUUCCACCACGGGUUCGGCAUGUUCACCACGCUG
GGGUACCUCAUCUGCGGCUUCCGCGUGGUCCUGAUGUACCGGUUCGAGGAGGAGCUGUUC
CUCCGCUCCCUGCAGGACUACAAGAUCCAGAGCGCCCUGCUCGUGCCCACCCUGUUCUCC
UUCUUCGCCAAGAGCACCCUGAUCGACAAGUACGACCUCUCCAACCUGCACGAGAUCGCG
AGCGGCGGGGCCCCGCUGAGCAAGGAGGUGGGCGAGGCCGUCGCCAAGCGGUUCCACCUC
CCCGGGAUCCGCCAGGGCUACGGGCUGACCGAGACGACCUCCGCCAUCCUGAUCACCCCC
GAGGGCGACGACAAGCCCGGCGCGGUGGGAAGGUGGUCCCGUUCUUCGAGGCCAAGGUG
GUCGACCUCGACACCGGCAAGACGCUGGGGGUGAACCAGCGGGGCGAGCUGUGCGUGCGC
GGGCCCAUGAUCAUGAGCGGCUACGUCAACAACCCCGAGGCCACCAACGCCCUCAUCGAC
AAGGACGGCUGGCUGCACUCCGGGGACAUCGCCUACUGGGACGAGGACGAGCACUUCUUC
AUCGUGGACCGGCUGAAGAGCCUCAUCAAGUACAAGGGCUACCAGGUGGCGCCCGCCGAG
CUGGAGUCCAUCCUGCUCCAGCACCCGAACAUCUUCGACGCCGGGUCGCCGGCCUGCCC
GACGACGACGCGGGGGAGCUGCCCGCCGCCGUGGUGGUCCUCGAGCACGGCAAGACCAUG
ACCGAGAAGGAGAUCGUGGACUACGUGGCCAGCCAGGUCACGACCGCCAAGAAGCUGCGC
GGCGGGGUGGUGUUCGUCGACGAGGUGCCCAAGGGCCUGACCGGGAAGCUGGACGCGCGG
AAGAUCCGCGAGAUCCUCAUCAAGGCCAAGAAGGGCGGCAAGAUCGCCGUCUGAGGACUA
GUAGAUCUAAAAAAAAAAAAAAAAAAAAAAAAAAAAAAAAAAAAAAAAAAAAAAAAAAAA
AAAAAAAAAAAAAAAAAA

GGGAGAUGUACAAAGCUUACCAUGGAGGACGCCAAGAACAUCAAGAAGGGCCCCGCCCCC
UUCUACCCCCUCGAGGACGGCACCGCCGGCGAGCAGCUCCACAAGGCCAUGAAGCGCUAC
GCCCUCGUCCCGGCACCAUCGCCUUCACCGACGCCCACAUCGAGGUCGACAUCACCUAC
GCCGAGUACUUCGAGAUGUCCGUCCGCCUCGCCGAGGCCAUGAAGCGCUACGGCCUCAAC
ACCAACCACCGCAUCGUCGUCUGCUCCGAGAACUCCCUCCAGUUCUUCAUGCCCGUCCUC
GGCGCCCUCUUCAUCGGCGUCGCCGUCGCCCCGCCAACGACAUCUACAACGAGCGCGAG
CUCCUCAACUCCAUGGGCAUCUCCCAGCCCACCGUCGUCUUCGUCUCCAAGAAGGGCCUC
CAGAAGAUCCUCAACGUCCAGAAGAAGCUCCCCAUCAUCCAGAAGAUCAUCAUCAUGGAC
UCCAAGACCGACUACCAGGGCUUCCAGUCCAUGUAUACCUUCGUCACCUCCCACCUCCCC
CCCGGCUUCAACGAGUACGACUUCGUCCCCGAGUCCUUCGACCGCGACAAGACCAUCGCC
CUCAUCAUGAACUCCUCCGGCUCCACCGGCCUCCCCAAGGGCGUCGCCCUCCCCCACCGC
ACCGCCUGCGUCCGCUUCUCCCACGCCCGCGACCCCAUCUUCGGCAACCAGAUCAUCCCC
GACACCGCCAUCCUCUCCGUCGUCCCCUUCCACCACGGCUUCGGCAUGUUCACCACCCUC
GGCUACCUCAUCUGCGGCUUCCGCGUCGUCCUCAUGUACCGCUUCGAGGAGGAGCUCUUC
CUCCGCUCCCUCCAGGACUACAAGAUCCAGUCCGCCCUCCUCGUCCCCACCCUCUUCUCC
UUCUUCGCCAAGUCCACCCUCAUCGACAAGUACGACCUCUCCAACCUCCACGAGAUCGCC
UCCGGCGGCGCCCCCCUCUCCAAGGAGGUCGGCGAGGCCGUCGCCAAGCGCUUCCACCUC
CCCGGCAUCCGCCAGGGCUACGGCCUCACCGAGACCACCUCCGCCAUCCUCAUCACCCCC
GAGGGCGACGACAAGCCCGGCGCCGUCGGCAAGGUCGUCCCCUUCUUCGAGGCCAAGGUC
GUCGACCUCGACACCGGCAAGACCCUCGGCGUCAACCAGCGCGGCGAGCUCUGCGUCCGC
GGCCCCAUGAUCAUGUCCGGCUACGUCAACAACCCCGAGGCCACCAACGCCCUCAUCGAC
AAGGACGGCUGGCUCCACUCCGGCGACAUCGCCUACUGGGACGAGGACGAGCACUUCUUC
AUCGUCGACCGCCUCAAGUCCCUCAUCAAGUACAAGGGCUACCAGGUCGCCCCCGCCGAG
CUCGAGUCCAUCCUCCUCCAGCACCCCAACAUCUUCGACGCCGGCGUCGCCGGCCUCCCC
GACGACGACGCCGGCGAGCUCCCCGCCGCCGUCGUCGUCCUCGAGCACGGCAAGACCAUG
ACCGAGAAGGAGAUCGUCGACUACGUCGCCUCCCAGGUCACCACCGCCAAGAAGCUCCGC
GGCGGCGUCGUCUUCGUCGACGAGGUCCCCAAGGGCCUCACCGGCAAGCUCGACGCCCGC
AAGAUCCGCGAGAUCCUCAUCAAGGCCAAGAAGGGCGGCAAGAUCGCCGUCUGAGGACUA
GUAGAUCUAAAAAAAAAAAAAAAAAAAAAAAAAAAAAAAAAAAAAAAAAAAAAAAAAAAA
AAAAAAAAAAAAAAAAAA

GGGAGAAAGCUUACCAUGGAGGACGCCAAGAACAUCAAGAAGGGCCCCGCCCCCUUCUAC
CCCCUGGAGGACGGGACCGCCGGCGAGCAGCUCCACAAGGCCAUGAAGCGGUACGCCCUG
GUGCCCGGGACCAUCGCCUUCACCGACGCCCACAUCGAGGUCGACAUCACCUACGCCGAG
UACUUCGAGAUGAGCGUGCGCCUGGCCGAGGCCAUGAAGCGGUACGGCCUCAACACCAAC
CACCGCAUCGUGGUCUGCUCCGAGAACAGCCUGCAGUUCUUCAUGCCCGUGCUGGGGCC
CUCUUCAUCGGCGUGGCCGUCGCCCCGCCAACGACAUCUACAACGAGCGGGAGCUGCUG
AACUCCAUGGGCAUCAGCCAGCCCACCGUGGUGUUCGUCUCCAAGAAGGGGCUCCAGAAG
AUCCUGAACGUGCAGAAGAAGCUGCCCAUCAUCCAGAAGAUCAUCAUGGACAGCAAG
ACCGACUACCAGGGCUUCCAGUCCAUGUAUACCUUCGUGACCAGCCACCUCCCUCCCGGG
UUCAACGAGUACGACUUCGUCCCCGAGUCCUUCGACCGCGACAAGACCAUCGCCCUGAUC
AUGAACAGCUCCGGCAGCACCGGGCUGCCCAAGGGCGUGGCCCUCCCCCACCGGACCGCC
UGCGUGCGCUUCUCCCACGCCCGGGACCCCAUCUUCGGCAACCAGAUCAUCCCCGACACC
GCCAUCCUGAGCGUCGUGCCCUUCCACCACGGGUUCGGCAUGUUCACCACCCUGGGGUAC
CUCAUCUGCGGCUUCCGCGUGGUCCUGAUGUACCGGUUCGAGGAGGAGCUGUUCCUCCGC
UCCCUGCAGGACUACAAGAUCCAGAGCGCCCUGCUCGUGCCCACCCUGUUCUCCUUCUUC
GCCAAGAGCACCCUGAUCGACAAGUACGACCUCUCCAACCUGCACGAGAUCGCCAGCGGC
GGGGCCCCUCUGAGCAAGGAGGUGGGCGAGGCCGUCGCCAAGCGGUUCCACCUCCCCGGG
AUCCGCCAGGGCUACGGGCUGACCGAGACCACCUCCGCCAUCCUGAUCACCCCCGAGGGC
GACGACAAGCCCGGCGCCGUGGGGAAGGUGGUCCCCUUCUUCGAGGCCAAGGUGGUCGAC
CUCGACACCGGCAAGACCCUGGGGGUGAACCAGCGGGGCGAGCUGUGCGUGCGCGGGCCC
AUGAUCAUGAGCGGCUACGUCAACAACCCCGAGGCCACCAACGCCCUCAUCGACAAGGAC
GGCUGGCUGCACUCCGGGGACAUCGCCUACUGGGACGAGGACGAGCACUUCUUCAUCGUG
GACCGGCUGAAGAGCCUCAUCAAGUACAAGGGCUACCAGGUGGCCCCCGCCGAGCUGGAG
UCCAUCCUGCUCCAGCACCCCAACAUCUUCGACGCCGGGGUCGCCGGCCUGCCCGACGAC
GACGCCGGGGAGCUGCCCGCCGCCGUGGUGGUCCUCGAGCACGGCAAGACCAUGACCGAG
AAGGAGAUCGUGGACUACGUGGCCAGCCAGGUCACCACCGCCAAGAAGCUGCGCGGCGGG
GUGGUGUUCGUCGACGAGGUGCCCAAGGGCCUGACCGGGAAGCUGGACGCCCGGAAGAUC
CGCGAGAUCCUCAUCAAGGCCAAGAAGGGCGGCAAGAUCGCCGUCUGAGGACUAGUAGAU
CUAAAAAAAAAAAAAAAAAAAAAAAAAAAAAAAAAAAAAAAAAAAAAAAAAAAAAAAAAA
AAAAAA

GGGAGAAAGCUUACCAUGGAGGACGCCAAGAACAUCAAGAAGGGCCCCGCCCCCUUCUAC
CCCCUCGAGGACGGCACCGCCGGCGAGCAGCUCCACAAGGCCAUGAAGCGCUACGCCCUC
GUCCCCGGCACCAUCGCCUUCACCGACGCCCACAUCGAGGUCGACAUCACCUACGCCGAG
UACUUCGAGAUGUCCGUCCGCCUCGCCGAGGCCAUGAAGCGCUACGGCCUCAACACCAAC
CACCGCAUCGUCGUCUGCUCCGAGAACUCCUCCAGUUCUUCAUGCCCGUCCUCGGCGCC
CUCUUCAUCGGCGUCGCCGUCGCCCCGCCAACGACAUCUACAACGAGCGCGAGCUCCUC
AACUCCAUGGGCAUCUCCCAGCCCACCGUCGUCUUCGUCUCCAAGAAGGGCCUCCAGAAG
AUCCUCAACGUCCAGAAGAAGCUCCCCAUCAUCCAGAAGAUCAUCAUCAUGGACUCCAAG
ACCGACUACCAGGGCUUCCAGUCCAUGUAUACCUUCGUCACCUCCCACCUCCCCCCGGC
UUCAACGAGUACGACUUCGUCCCCGAGUCCUUCGACCGCGACAAGACCAUCGCCCUCAUC
AUGAACUCCUCCGGCUCCACCGGCCUCCCCAAGGGCGUCGCCCUCCCCCACCGCACCGCC
UGCGUCCGCUUCUCCCACGCCCGCGACCCCAUCUUCGGCAACCAGAUCAUCCCCGACACC
GCCAUCCUCUCCGUCGUCCCCUUCCACCACGGCUUCGGCAUGUUCACCACCCUCGGCUAC
CUCAUCUGCGGCUUCCGCGUCGUCCUCAUGUACCGCUUCGAGGAGGAGCUCUUCCUCCGC
UCCCUCCAGGACUACAAGAUCCAGUCCGCCCUCCUCGUCCCCACCCUCUUCUCCUUCUUC
GCCAAGUCCACCCUCAUCGACAAGUACGACCUCUCCAACCUCCACGAGAUCGCCUCCGGC
GGCGCCCCCCUCUCCAAGGAGGUCGGCGAGGCCGUCGCCAAGCGCUUCCACCUCCCCGGC
AUCCGCCAGGGCUACGGCCUCACCGAGACCACCUCCGCCAUCCUCAUCACCCCCGAGGGC
GACGACAAGCCCGGCGCCGUCGGCAAGGUCGUCCCCUUCUUCGAGGCCAAGGUCGUCGAC
CUCGACACCGGCAAGACCCUCGGCGUCAACCAGCGCGGCGAGCUCUGCGUCCGCGGCCCC
AUGAUCAUGUCCGGCUACGUCAACAACCCCGAGGCCACCAACGCCCUCAUCGACAAGGAC
GGCUGGCUCCACUCCGGCGACAUCGCCUACUGGGACGAGGACGAGCACUUCUUCAUCGUC
GACCGCCUCAAGUCCCUCAUCAAGUACAAGGGCUACCAGGUCGCCCCCGCCGAGCUCGAG
UCCAUCCUCCUCCAGCACCCCAACAUCUUCGACGCCGGCGUCGCCGGCCUCCCCGACGAC
GACGCCGGCGAGCUCCCCGCCGCCGUCGUCGUCCUCGAGCACGGCAAGACCAUGACCGAG
AAGGAGAUCGUCGACUACGUCGCCUCCCAGGUCACCACCGCCAAGAAGCUCCGCGGCGGC
GUCGUCUUCGUCGACGAGGUCCCCAAGGGCCUCACCGGCAAGCUCGACGCCCGCAAGAUC
CGCGAGAUCCUCAUCAAGGCCAAGAAGGGCGGCAAGAUCGCCGUCUGAGGACUAGUAGAU
CUAAAAAAAAAAAAAAAAAAAAAAAAAAAAAAAAAAAAAAAAAAAAAAAAAAAAAAAAAA
AAAAAA

GGGGCGCUGCCUACGGAGGUGGCAGCCAUCUCCUUCUCGGCAUCAAGCUUACCAUGGAGG
ACGCCAAGAACAUCAAGAAGGGCCCCGCCCCGUUCUACCCCUGGAGGACGGGACCGCGG
GCGAGCAGCUCCACAAGGCCAUGAAGCGGUACGCCCUGGUGCCCGGGACCAUCGCCUUCA
CGGACGCCCACAUCGAGGUCGACAUCACCUACGCGGAGUACUUCGAGAUGAGCGUGCGCC
UGGCCGAGGCCAUGAAGCGGUACGGCCUCAACACCAACCACCGCAUCGUGGUCUGCUCCG
AGAACAGCCUGCAGUUCUUCAUGCCCGUGCUGGGGCCCUCUUCAUCGGCGUGGCGGUCG
CCCCGGCCAACGACAUCUACAACGAGCGGGAGCUGCUGAACUCCAUGGGCAUCAGCCAGC
CCACCGUGGUGUUCGUCUCCAAGAAGGGGCUCCAGAAGAUCCUGAACGUGCAGAAGAAGC
UGCCGAUCAUCCAGAAGAUCAUCAUCAUGGACAGCAAGACGGACUACCAGGGCUUCCAGU
CCAUGUAUACCUUCGUGACCAGCCACCUCCCCCGGGGUUCAACGAGUACGACUUCGUCC
CCGAGUCCUUCGACCGCGACAAGACCAUCGCCCUGAUCAUGAACAGCUCCGGCAGCACGG
GGCUGCCCAAGGGCGUGGCCCUCCCCCACCGGACCGCGUGCGUGCGCUUCUCCCACGCCC
GGGACCCGAUCUUCGGCAACCAGAUCAUCCCCGACACCGCCAUCCUGAGCGUCGUGCCCU
UCCACCACGGGUUCGGCAUGUUCACCACGCUGGGGUACCUCAUCUGCGGCUUCCGCGUGG
UCCUGAUGUACCGGUUCGAGGAGGAGCUGUUCCUCCGCUCCCUGCAGGACUACAAGAUCC
AGAGCGCCCUGCUCGUGCCCACCCUGUUCUCCUUCUUCGCCAAGAGCACCCUGAUCGACA
AGUACGACCUCUCCAACCUGCACGAGAUCGCGAGCGGCGGGGCCCCGCUGAGCAAGGAGG
UGGGCGAGGCCGUCGCCAAGCGGUUCCACCUCCCCGGGAUCCGCCAGGGCUACGGGCUGA
CCGAGACGACCUCCGCCAUCCUGAUCACCCCCGAGGGCGACGACAAGCCCGGCGCGGUGG
GGAAGGUGGUCCCGUUCUUCGAGGCCAAGGUGGUCGACCUCGACACCGGCAAGACGCUGG
GGGUGAACCAGCGGGGCGAGCUGUGCGUGCGCGGGCCCAUGAUCAUGAGCGGCUACGUCA
ACAACCCCGAGGCCACCAACGCCCUCAUCGACAAGGACGGCUGGCUGCACUCCGGGGACA
UCGCCUACUGGGACGAGGACGAGCACUUCUUCAUCGUGGACCGGCUGAAGAGCCUCAUCA
AGUACAAGGGCUACCAGGUGGCGCCCGCCGAGCUGGAGUCCAUCCUGCUCCAGCACCCGA
ACAUCUUCGACGCCGGGGUCGCCGGCCUGCCCGACGACGACGCGGGGGAGCUGCCCGCCG
CCGUGGUGGUCCUCGAGCACGGCAAGACCAUGACCGAGAAGGAGAUCGUGGACUACGUGG
CCAGCCAGGUCACGACCGCCAAGAAGCUGCGCGGCGGGGUGGUGUUCGUCGACGAGGUGC
CAAGGGCCUGACCGGGAAGCUGGACGCGCGGAAGAUCCGCGAGAUCCUCAUCAAGGCCA
AGAAGGGCGGCAAGAUCGCCGUCUGAGGACUAGUGCAUCACAUUUAAAAGCAUCUCAGCC
UACCAUGAGAAUAAGAGAAAGAAAAUGAAGAUCAAUAGCUUAUUCAUCUCUUUUUCUUUU
UCGUUGGUGUAAAGCCAACACCCUGUCUAAAAAACAUAAAUUUCUUUAAUCAUUUUGCCU
CUUUUCUCUGUGCUUCAAUUAAUAAAAAAUGGAAAGAACCUAGAUCUAAAAAAAAAAAA
AAAAAAAAAAAAAAAAAAAAAAAAAAAAAAAAAAAAAAAAAAAAAAAAAAAUGCAUCCCC
CCCCCCCCCCCCCCCCCCCCCCCCAAAGGCUCUUUUCAGAGCCACCAGAAUU

GGGGCGCUGCCUACGGAGGUGGCAGCCAUCUCCUUCUCGGCAUCAAGCUUACCAUGGAGG
ACGCCAAGAACAUCAAGAAGGGCCCCGCCCCCUUCUACCCCCUCGAGGACGGCACCGCCG
GCGAGCAGCUCCACAAGGCCAUGAAGCGCUACGCCCUCGUCCCCGGCACCAUCGCCUUCA
CCGACGCCCACAUCGAGGUCGACAUCACCUACGCCGAGUACUUCGAGAUGUCCGUCCGCC
UCGCCGAGGCCAUGAAGCGCUACGGCCUCAACACCAACCACCGCAUCGUCGUCUGCUCCG
AGAACUCCCUCCAGUUCUUCAUGCCCGUCCUCGGCGCCCUCUUCAUCGGCGUCGCCGUCG
CCCCCGCCAACGACAUCUACAACGAGCGCGAGCUCCUCAACUCCAUGGGCAUCUCCCAGC
CCACCGUCGUCUUCGUCUCCAAGAAGGGCCUCCAGAAGAUCCUCAACGUCCAGAAGAAGC
UCCCCAUCAUCCAGAAGAUCAUCAUCAUGGACUCCAAGACCGACUACCAGGGCUUCCAGU
CCAUGUAUACCUUCGUCACCUCCCACCUCCCCCCGGCUUCAACGAGUACGACUUCGUCC
CCGAGUCCUUCGACCGCGACAAGACCAUCGCCCUCAUCAUGAACUCCUCCGGCUCCACCG
GCCUCCCCAAGGGCGUCGCCCUCCCCCACCGCACCGCCUGCGUCCGCUUCUCCCACGCCC
GCGACCCCAUCUUCGGCAACCAGAUCAUCCCCGACACCGCCAUCCUCUCCGUCGUCCCCU
UCCACCACGGCUUCGGCAUGUUCACCACCCUCGGCUACCUCAUCUGCGGCUUCCGCGUCG
UCCUCAUGUACCGCUUCGAGGAGGAGCUCUUCCUCCGCUCCCUCCAGGACUACAAGAUCC
AGUCCGCCCUCCUCGUCCCCACCCUCUUCUCCUUCUUCGCCAAGUCCACCCUCAUCGACA
AGUACGACCUCUCCAACCUCCACGAGAUCGCCUCCGGCGGCGCCCCCCUCUCCAAGGAGG
UCGGCGAGGCCGUCGCCAAGCGCUUCCACCUCCCCGGCAUCCGCCAGGGCUACGGCCUCA
CCGAGACCACCUCCGCCAUCCUCAUCACCCCCGAGGGCGACGACAAGCCCGGCGCCGUCG
GCAAGGUCGUCCCCUUCUUCGAGGCCAAGGUCGUCGACCUCGACACCGGCAAGACCCUCG
GCGUCAACCAGCGCGGCGAGCUCUGCGUCCGCGGCCCCAUGAUCAUGUCCGGCUACGUCA
ACAACCCCGAGGCCACCAACGCCCUCAUCGACAAGGACGGCUGGCUCCACUCCGGCGACA
UCGCCUACUGGGACGAGGACGAGCACUUCUUCAUCGUCGACCGCCUCAAGUCCCUCAUCA
AGUACAAGGGCUACCAGGUCGCCCCCGCCGAGCUCGAGUCCAUCCUCCUCCAGCACCCCA
ACAUCUUCGACGCCGGCGUCGCCGGCCUCCCCGACGACGACGCCGGCGAGCUCCCCGCCG
CCGUCGUCGUCCUCGAGCACGGCAAGACCAUGACCGAGAAGGAGAUCGUCGACUACGUCG
CCUCCCAGGUCACCACCGCCAAGAAGCUCCGCGGCGGCGUCGUCUUCGUCGACGAGGUCC
CCAAGGGCCUCACCGGCAAGCUCGACGCCCGCAAGAUCCGCGAGAUCCUCAUCAAGGCCA
AGAAGGGCGGCAAGAUCGCCGUCUGAGGACUAGUGCAUCACAUUUAAAAGCAUCUCAGCC
UACCAUGAGAAUAAGAGAAAGAAAAUGAAGAUCAAUAGCUUAUUCAUCUCUUUUUCUUUU
UCGUUGGUGUAAAGCCAACACCCUGUCUAAAAAACAUAAAUUUCUUUAAUCAUUUUGCCU
CUUUUCUCUGUGCUUCAAUUAAUAAAAAUGGAAAGAACCUAGAUCUAAAAAAAAAAAAA
AAAAAAAAAAAAAAAAAAAAAAAAAAAAAAAAAAAAAAAAAAAAUGCAUCCCC
CCCCCCCCCCCCCCCCCCCCCCCCCAAAGGCUCUUUUCAGAGCCACCAGAAUU

Fig. 7

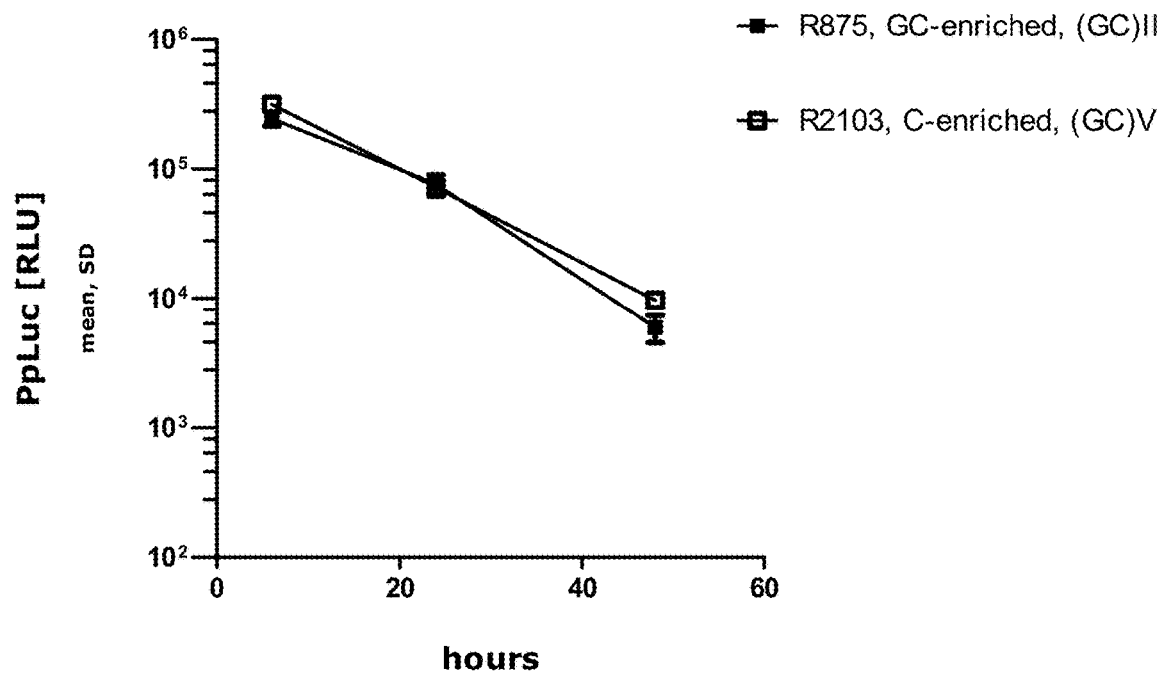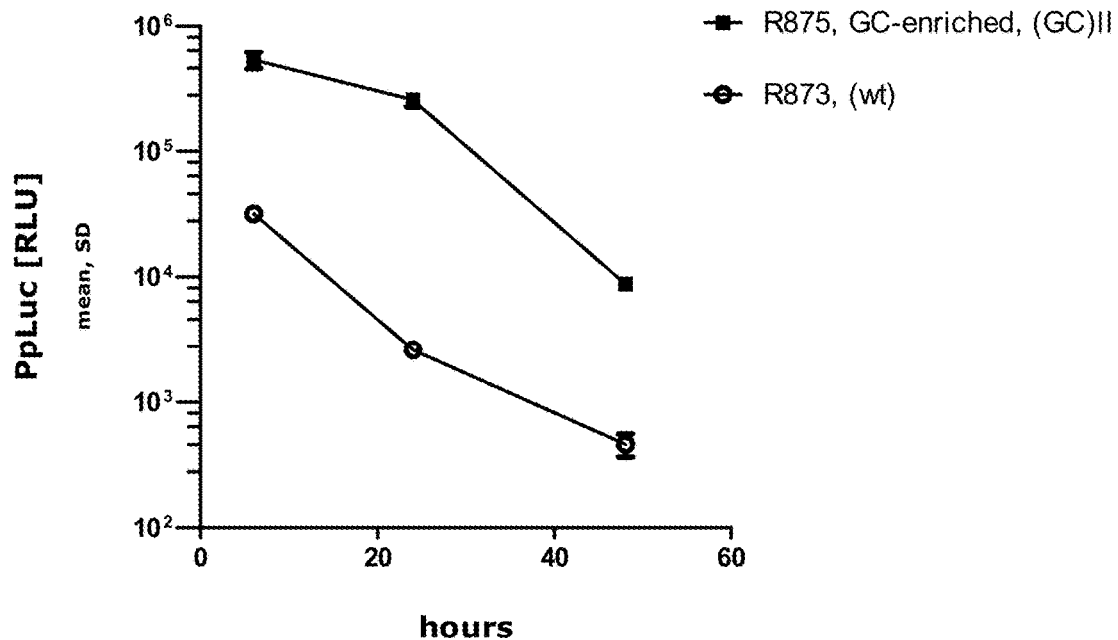
Figs. 9A-B

MODIFIED RNA WITH DECREASED IMMUNOSTIMULATORY PROPERTIES

This application is a continuation of International Application No. PCT/EP2014/002931, filed Oct. 31, 2014, which claims priority to International Application No. PCT/EP2013/003293, filed Nov. 1, 2013. The entire contents of each of the above referenced disclosures are specifically incorporated herein by reference.

FIELD OF THE INVENTION

The present invention relates to a method for providing an mRNA with decreased immunostimulatory properties, which encodes at least one biologically active polypeptide or protein and its use in protein replacement therapy.

BACKGROUND OF THE INVENTION

Therapeutic RNA molecules represent an emerging class of drugs. RNA-based therapeutics include messenger RNA (mRNA) molecules encoding antigens for use as vaccines. mRNA vaccines combine desirable immunological properties with the flexibility of genetic vaccines. One of several advantages of using mRNA for vaccination is that the same molecule not only provides an antigen source for the induction of an adaptive immune response, but can simultaneously bind to pattern recognition receptors such as Toll like receptors (TLRs) and thereby stimulate innate immunity. It has previously been reported that a two-component mRNA-based vaccine with dual activity induces balanced TLR-7 dependent adaptive immune responses and provides anti-tumor activity (Fotin-Mleczek et al., 2011. J. Immunother. 34(1):1-15). In addition, mRNA is considered to be a safer vector than DNA-based vectors because RNA cannot integrate into genomic DNA possibly leading to insertional mutagenesis.

mRNA molecules may also be used as therapeutics for replacement therapies, such as e.g. protein replacement therapies for substituting missing or mutated proteins such as growth factors or enzymes, in patients. However, successful development of safe and efficacious mRNA-based replacement therapies are based on different requirements compared to vaccines. When applying mRNA for protein replacement therapies, the mRNA should confer maximal expression of the protein of interest in terms of expression level and duration and minimal stimulation of the immune system to avoid general immune responses by the patient to be treated and specific immune responses against the administered mRNA molecule.

Whereas the inherent immunostimulatory property of mRNA is considered as a desirable feature for vaccines, this effect may cause undesired complications in replacement therapies. This is especially the case for the treatment of chronic diseases in which the mRNA therapeutic needs to be administered repeatedly over an extended period of time to patients. Although it has been demonstrated in animal studies that mRNA-encoded growth factor erythropoietin (EPO) can be successfully expressed in vivo resulting in biologically relevant increases of reticulocytes (Schlake et al., 2012. RNA Biol. 9(11):1319-30; Kariko et al., 2012. Mol. Ther. 20(5):948-53; Kormann et al., 2011. Nat. Biotechnol. 29(4154-7), it has been recognized that the immunostimulating properties of the mRNA may potentially give rise to issues during therapy. Accordingly, such properties should be decreased.

Mammalian cells harbor a diverse set of nucleic acid-sensing pattern recognition factors (PRRs) receptors that recognize RNA by various recognition patterns (Review: Desmet et al., 2012. Nat. Rev. Immunol. 12(7):479-91). Toll-like receptors (TLRs) are the best studied group of pattern recognition factors (PRRs). Out of the 10 human TLRs four TLRs (TLR3, TLR7, TLR8 and TLR9) are nucleic acid sensors that recognize diverse pathogen-derived nucleic acids. Whereas TLR3, TLR7 and TLR8 recognize RNA, TLR9 binds to CpG motifs in DNA. TLR3, TLR7, TLR8 and TLR9 are intracellular TLRs and recognize nucleic acids that are taken up by the cell via endocytosis and transferred to endosomes. With the exception of TLR3, all nucleic acid-sensing TLRs use the adaptor protein MYD88 for downstream signaling to activate the transcription factors AP1 and NF-□B leading to the expression of pro-inflammatory cytokines. These cytokines mediate the recruitment and activation of immune cells. TLR3 signaling depends on the TIR-domain-containing adaptor protein inducing IFN□ (TRIF) leading to the expression of pro-inflammatory cytokines as well as type I interferons (IFNs), which play a role in antiviral responses. For example, following TLR7 and TLR9 activation, plasmacytoid dendritic cells (pDCs) can produce large amounts of type I interferons (Desmet et al., 2012. Nat. Rev. Immunol. 12(7): 479-91).

RIG-I-like receptors (RLRs) are members of the DExD/H-box helicase superfamily that act as cytosolic RNA sensors. Members of this family are retinoic acid-inducible gene I (RIG-I), melanoma differentiation-associated protein 5 (MDA5) and laboratory of genetics and physiology 2 (LGP2). RLRs are expressed broadly by immune and non-immune cells. The typical natural ligand of RIG-I is a short RNA with blunt-ended base-pairing and an uncapped 5' triphosphate end, but RIG-I has also been shown to bind to various double-stranded RNA (dsRNA) and single-stranded RNA (ssRNA) ligands. MDA5 generally binds to long dsRNA molecules but is also involved in the discrimination of self and non-self RNAs based on the ribose 2'-O-methylation status of the cap structure (Züst et al., 2011. Nat. Immunol. 12(2):137-43, PMID 21217758). In addition, RIG-I and MDA5 can be activated by self RNAs that are cleaved by RNAse L. RNase L is a ribonuclease that is induced in response to type I interferons and degrades all the RNA within the cell. RLR signaling depends on the adaptor IFNB-promotor stimulator 1 (IPS1) leading to the activation of transcription factors IRF1, IRF3, IRF7 and NF-κB and subsequently to the expression of type I IFNs and pro-inflammatory cytokines (Broz et al., 2013. Nat. Rev. Immunol. 13(8):551-65).

2'-5' oligoadenylate synthetases (OASs) and the protein kinase regulated by RNA (PKR) are both interferon-induced, dsRNA-dependent enzymes located in the cytosol that play important roles in mediating the antiviral effects of the interferons. PKR is a protein serine/threonine kinase that acquires enzymatic activity following autophosphorylation, a process mediated by dsRNA. Activation of PKR allows the kinase to phosphorylate its natural substrate, the alpha subunit of eukaryotic protein synthesis initiation factor-2 (EIF2-alpha), leading to the inhibition of protein synthesis. The 2'-5' oligoadenylate synthetases are also activated by dsRNA and subsequently polymerize ATP into 2'-5'-linked oligoadenylates (2'-5' (A)) of various lengths, which function as specific activators of a latent endoribonuclease, RNase L. Once activated by 2'-5' (A), RNase L degrades viral and cellular RNAs resulting in the inhibition of protein synthesis. Both enzymes, PKR and 2'-5' oligoadenylate synthetase, are activated by ssRNA and dsRNA that possess extensive secondary structure (Sharp et al., 1999. Virology 257(2):303-13).

Accordingly, RNA molecules may exert an unspecific immune response in patients, which should be avoided or at least reduced. Several approaches were described for decreasing the immunostimulatory properties of mRNA including the incorporation of naturally occurring modified nucleosides into in vitro transcribed mRNA. The purification of such mRNAs is expected to remove contaminants or double-stranded RNA. Alternatively, the synthesis and use of novel non-naturally occurring modified nucleosides with decreased immunostimulatory potential was envisaged as well.

Kariko et al. demonstrated that different mRNAs stimulated the secretion of cytokines, such as TNF☐, by human dendritic cells (DCs) to various extents, an effect that was attributed to the engagement of TLR3, 7 and 8 (Kariko et al., 2005. Immunity 23(4165-75). Whereas synthetic dsRNA, in vitro transcribed RNA as well as bacterial and mitochondrial RNA induced strong cytokine secretion, cytoplasmic RNA from mammalian cells stimulated DCs to a much lower extent. In addition, it was shown that RNA signals through human TLR3, TLR7, and TLR8. Incorporation of modified nucleosides such as 5-methylcytidine (m5C), N6-methyladenosine (m6A), 5-methyluridine (m5U), 2-thiouridine (s2U), or pseudouridine (ψ), however, ablated this activity. Dendritic cells (DCs) treated with modified RNA expressed significantly less cytokines and activation markers than those treated with unmodified RNA. The authors concluded that nucleoside modifications suppress the potential of RNA to activate DCs. Therefore, it was suggested that mRNAs containing naturally occurring modified nucleosides may be used in clinical applications due to their reduced immunostimulating properties (Kariko et al., 2007. Curr. Opin. Drug Discov Devel. 10(5):523-32; WO2007024708A1).

Further work demonstrated that in vitro generated mRNA containing uridine activated RNA-dependent protein kinase (PKR), which then phosphorylated translation initiation factor 2-alpha (eIF-2☐), and inhibited translation. In contrast, in vitro transcribed mRNAs containing pseudouridine as a modified nucleoside activated PKR to a lesser degree, while translation of pseudouridine-containing mRNAs was not repressed (Anderson et al., 2010. Nucleic Acids Res. 38(17):5884-92).

In addition, the Kariko group showed that in vitro transcribed, unmodified RNA activates 2'-5' oligoadenylate synthetase (OAS), induced RNase L-mediated ribosomal RNA (rRNA) cleavage and was rapidly cleaved by RNase L. In contrast, RNA containing modified nucleosides activated OAS less efficiently and induced limited rRNA cleavage, thus showing the role of nucleoside modifications in suppressing immune recognition of RNA (Anderson et al., 2011. Nucleic Acids Res. 39(21):9329-38).

Purification of in vitro transcribed mRNA by high performance liquid chromatography (HPLC) has been shown to reduce immune activation by transfected mRNA. It was reported that contaminants, including dsRNA, in nucleoside-modified in vitro transcribed RNA were responsible for innate immune activation and that their removal by high performance liquid chromatography (HPLC) resulted in mRNA that did not induce the production of IFNs and inflammatory cytokines. It was translated at 10- to 1000-fold greater levels in primary cells. Although unmodified mRNAs were translated significantly better following purification, they still induced significant levels of cytokine secretion (Kariko et al., 2011. Nucleic Acids Res. 39(21): e142).

Treatment of mice with pseudouridine modified mRNA coding for erythropoietin (EPO) gave rise to higher protein expression and stronger biological effects compared to unmodified mRNA. Moreover, the modified RNA did not induce detectable levels of interferon ☐ and anti-EPO antibodies in plasma. In addition, it was shown that intraperitoneal injection of EPO mRNA into macaques increased serum EPO levels (Kariko et al., Mol. Ther. 20(5):948-53).

By another study, using a combination of different nucleotide modifications, enhanced expression and reduced immunostimulation of an EPO-encoding mRNA was demonstrated in mice. Furthermore, in a mouse model of a lethal congenital lung disease caused by the lack of surfactant protein B (SP-B), the application of an aerosol of modified SP-B mRNA to the lung showed a therapeutic effect (Kormann et al., 2011. Nat. Biotechnol. 29(2):154-7; WO2011012316).

The induction of induced pluripotent stem cells (iPSCs) was reported by transfection of human cells with synthetic modified mRNA. Improved expression and reduced immunostimulation, indicated by lower expression of interferon-regulated genes, were observed with base-modified mRNAs containing 5-methylcytidine and pseudouridine (Warren et al., 2010. Cell Stem Cell. 7(5):618-30; WO2011130624; WO2011071931).

WO2013/052523 reports novel modified nucleosides, nucleotides and nucleic acids which can exhibit a reduced innate immune response when introduced into cells. However, any approach to reduce innate immune stimulation based on an mRNA containing non-natural modified nucleosides is less desired. Any such modification, which does not usually occur in patients, bears the risk of undesired side effects.

In view of the above, there is a continued need for novel methods to reduce the immunostimulatory properties of mRNA while maintaining efficient protein expression and a good safety profile avoiding any risk of undesired side effects.

SUMMARY OF THE INVENTION

The present inventors have identified an appropriate method to modulate, preferably decrease, the immunogenicity and/or immunostimulatory capacity of a target mRNA (immune response against an mRNA), which encodes at least one biologically active polypeptide or protein, by preferably increasing the cytosine-content (C-content) of the coding region encoding the at least one biologically active polypeptide or protein and optionally exchanging additionally relatively rare codons in the target wild type sequence by relatively frequent codons that code for the same amino acid.

According to a first embodiment, the method for targeted modulation, preferably reduction of the immune response against an mRNA coding for at least one biologically active polypeptide or protein of the present invention comprises the steps of identifying a target mRNA wild type sequence coding for the biologically active polypeptide or protein and modifying said mRNA by replacing at least 70% of the codons of the wild type sequence, which are "cytosine content optimizable", by codons with a higher cytosine content, thereby increasing the cytosine-content of the mRNA such that the cytosine-content of the coding region of the modified mRNA (coding for the polypeptide or protein)

is larger than the cytosine-content of the coding region of the wild type mRNA (coding for the at least one polypeptide or protein), whereby the encoded amino acid sequence remains unchanged compared to the wild type (amino acid) sequence.

In a preferred embodiment of the present invention, the modified target mRNA is modified such that at least 10%, 20%, 30%, 40%, 50%, 60%, 70% or 80%, or at least 90% of the theoretically maximal cytosine-content or even a maximal cytosine-content is achieved.

In further preferred embodiments, at least 10%, 20%, 30%, 40%, 50%, 60%, 70%, 80%, 90% or even 100% of the codons of the target mRNA wild type sequence, which are "cytosine content optimizable" are replaced by codons with a higher cytosine-content as present in the wild type sequence.

In a further preferred embodiment, some of the codons of the wild type coding sequence may additionally be modified such that a codon for a relatively rare tRNA in the cell is exchanged by a codon for a relatively frequent tRNA in the cell, provided that the substituted codon for a relatively frequent tRNA carries the same amino acid as the relatively rare tRNA of the original wild type codon. Preferably, all of the codons for a relatively rare tRNA are replaced by a codon for a relatively frequent tRNA in the cell, except codons encoding amino acids, which are exclusively encoded by codons not containing any cytosine, or except for glutamine (Gln), which is encoded by two codons each containing the same number of cytosines.

In a further preferred embodiment of the present invention, the modified target mRNA is modified such that at least 80%, or at least 90% of the theoretically maximal cytosine-content or even a maximal cytosine-content is achieved by means of codons, which code for relatively frequent tRNAs in the cell, wherein the amino acid sequence remains unchanged.

Accordingly, the above objects of the present invention are solved by a method, which provides for a modified target mRNA encoding at least one biologically active polypeptide or protein with decreased immunogenicity and/or immunostimulatory capacity compared to the wild type sequence, wherein the C-content of the coding region of the modified target mRNA is typically increased by at least 10%, preferably by at least 12.5%, more preferably by at least 15% based on the cytosine-content of the polypeptide or protein coding region of the wild type mRNA.

In a specific embodiment, the present invention provides for a method, in which, additionally to the increase in cytosine-content, some codons, preferably all codons of the wild type sequence, which are not cytosine-content optimizable or which do not code for glutamine, and which reflect a relatively rare codon in the cell, are replaced by codons, which code for a relatively frequent tRNA in the cell, which carries the same amino acid as the relatively rare tRNA.

Preferably, the codon adaptation index (CAI) of the region of the immunologically modulated mRNA coding for the polypeptide or protein according to the invention is increased by at least 0.05, preferably by at least 0.1, preferably by at least 0.125, most preferable by at least 0.15 as compared to the CAI of the wild type coding region of the mRNA encoding for the polypeptide or protein. Accordingly, the modified mRNA displays preferably an increased level of expression compared to the wild type mRNA.

The method according to the present invention may further comprise the step of assaying the immunogenicity and/or immunostimulatory capacity of the modified target mRNA coding for the at least one polypeptide or protein.

Preferably, the immunogenicity and/or immunostimulatory capacity of the modified target mRNA encoding at least one biologically active polypeptide or protein is assayed by transfecting peripheral blood monocytes (PBMCs) in vitro with the inventive modified target mRNA, culturing the cells for at least 8 hours, preferably for at least 12 hours, more preferably for at least 20 hours and determining the amount of pro-inflammatory cytokines in the cell supernatant. The result of such an assay may be compared—in a further optional step—with the result of parallel experiments carried out for the underlying wild type (wt) sequence.

According to the invention, the target mRNA coding for the at least one biologically active polypeptide or protein of lower immunogenicity and/or immunostimulatory capacity compared to the wild type sequence is selected from all of the modified target mRNAs obtainable by a method of the invention. Optionally, the inventive method according to the above embodiments may be reiterated to further decrease the immunogenicity and/or immunostimulatory capacity of the target mRNA, which encodes at least one biologically active polypeptide or protein. Accordingly, alternative modified target mRNAs exhibiting the structural properties of the invention may be produced and tested.

According to one embodiment of the present invention, the targeted modulation of the immune response against an mRNA encoding at least one biologically active polypeptide or protein is carried out by way of executing at least one algorithm of the cytosine-optimization on a computer with the aid of suitable software.

The present invention also provides for a modified mRNA of reduced immunogenicity and/or immunostimulatory capacity encoding at least one biologically active polypeptide or protein according to one or more embodiments of the present invention, wherein the modified mRNA is obtained by means of chemical or biological synthesis. Preferably, the modified mRNA is obtained by in vitro transcription, preferably by bacteriophage polymerase-mediated in vitro transcription, e.g. by Sp6 polymerase in vitro transcription and/or T3 polymerase-mediated in vitro transcription, preferably by T7 polymerase-mediated in vitro transcription.

The present invention also provides a modified mRNA of reduced immunogenicity and/or immunostimulatory capacity encoding at least one biologically active polypeptide or protein obtainable by methods according to the invention.

In this context, it is particularly preferred that the modified mRNA of reduced immunogenicity and/or immunostimulatory capacity encoding at least one biologically active polypeptide or protein according to the invention has at least 10%, 20% or at least 30% lower immunogenicity and/or immunostimulatory capacity as compared to the respective wild type mRNA.

The modified mRNA of reduced immunogenicity and/or immunostimulatory capacity according to the present invention is typically characterized by a lower affinity, e.g. at least decreased by 20% to one or more, to TLR3, TLR7, TLR8, PKR, MDA5, RIG-I, LGP2 or 2'-5'-oligoadenylate synthetase, as compared to the wild type mRNA encoding the at least one polypeptide or protein.

Furthermore, the inventive modified mRNA according to one or more of the above embodiments comprises a 5' CAP structure, and/or at least one 3'- and/or 5'-UTR (untranslated region) and/or a polyA-tail of at least 60 nucleotides, more preferably of at least 70 nucleotides and/or a 3' stabilizing sequence.

Accordingly, the present invention also provides a pharmaceutical composition, which comprises a modified mRNA according to one or more of the above embodiments, which optionally comprises one or more pharmaceutically acceptable excipients, carriers, diluents and/or vehicles.

More specifically, the present invention provides a pharmaceutical composition according to the above embodiment or the modified mRNA according to one or more of the above embodiments for use in the treatment of protein replacement therapy, preferably for use in the treatment of e.g. hereditary or endocrinological diseases.

Furthermore, the present invention provides a method of treating a subject in need of protein replacement therapy, the method comprising administering to a subject in need thereof a pharmaceutically effective amount of the pharmaceutical composition according to one or more of the above embodiments or an effective amount of the modified mRNA according to one or more of the above embodiments.

More specifically, the present invention provides a method according to the above embodiment, wherein the disease to be treated by protein replacement therapy is selected from the group consisting of hereditary or endocrinological disorders, such as e.g. amino acid metabolism disorders, carbohydrate metabolism disorders, cholesterol biosynthesis disorders, fatty acid oxidation defects and fat metabolism disorders, lactic acidosis, glycogen storage diseases, mitochondrial disorders, organic acid disorders, urea cycle disorders, lysosomal storage disease disorders.

More preferably, the present invention provides a method for expressing a biologically active polypeptide or protein in a tissue in vivo, the method comprising contacting the patient with a pharmaceutical composition according to one or more of the above embodiments of the invention, or contacting the patient with the inventive modified mRNA according to any one of the above embodiments of the invention, wherein administering the pharmaceutical composition or the modified mRNA results in a reduced innate immune response by the patient relative to a patient, preferably the same patient, contacted with the wild type mRNA molecule encoding the same polypeptide or protein. Optionally, the level of mRNA expression in vivo is increased by the modified target mRNA of the invention as compared to the wild type mRNA.

According to a further embodiment, the present invention provides for a modified mRNA that codes for at least one biologically active polypeptide or protein, wherein the cytosine-content of the coding region of the modified mRNA is larger than the cytosine-content of the coding region of the wild type mRNA coding for the polypeptide or protein, whereby the encoded amino acid sequence is unchanged compared to the wild type sequence. In this context, it is preferred that, if no cytosine is present in any of the at least one codon coding for the amino acid, at least one codon of the wild type sequence that codes for a relatively rare tRNA in the cell is exchanged for a codon that codes for a relatively frequent tRNA in the cell that carries the same amino acid as the relatively rare tRNA.

BRIEF DESCRIPTION OF THE DRAWINGS

The present invention is described by the figures and examples below, which are used only for illustration purposes and are not meant to limit the scope of the invention. Owing to the description and examples, further embodiments are likewise included in the invention that are accessible to the skilled person.

FIG. 1: Wildtype mRNA sequence R873 coding for *Photinus pyralis* luciferase (PpLuc), which corresponds to SEQ ID NO:1. The mRNA was in vitro transcribed from a vector containing a T7 promoter followed by a sequence coding for *Photinus pyralis* luciferase (PpLuc(wt), and a poly(A) sequence of 70 adenosine nucleotides (A70). This sequence was subsequently used as a target sequence for modulating the immunogenicity and/or immunostimulatory capacity according to the inventive method.

FIG. 2: G/C-enriched mRNA sequence R875 which is obtained by G/C enrichment only coding for *Photinus pyralis* luciferase (PpLuc), which corresponds to SEQ ID NO:2. R875 was obtained by G/C enrichment of the sequence R873.

FIG. 3: C-enriched mRNA sequence R2103 obtained by G/C enrichment and subsequent C-enrichment coding for *Photinus pyralis* luciferase (PpLuc), which corresponds to SEQ ID NO: 3. R2103 was obtained by C-enrichment of the sequence R873.

FIG. 4: G/C-enriched mRNA sequence R2349 coding for *Photinus pyralis* luciferase (PpLuc), corresponding to SEQ ID NO:4. The mRNA was in vitro transcribed from a vector containing a T7 promoter followed by a G/C-enriched sequence coding for *Photinus pyralis* luciferase (PpLuc(GC) III) and a sequence of 64 adenosine nucleotides (A64) poly(A) sequence.

FIG. 5: C-enriched mRNA sequence of R2350 coding for *Photinus pyralis* luciferase (PpLuc), which corresponds to SEQ ID NO:5. The template for in vitro transcription was obtained by modifying the vector comprising the G/C-enriched sequence by replacing the GC-optimized coding sequence of PpLuc(GC)III (FIG. 4) by a C-enriched sequence. mRNA obtained from this vector by in vitro transcription is designated "PpLuc(GC)III-A64" (R2350).

FIG. 6: G/C-enriched mRNA sequence R2791 coding for *Photinus pyralis* luciferase (PpLuc), corresponding to SEQ ID NO:6. The vector used for in vitro transcription comprised a 5'-TOP-UTR derived from the ribosomal protein 32L, followed by a stabilizing sequence derived from the albumin-3'-UTR, a stretch of 64 adenosine nucleotides (poly (A)-sequence), a stretch of 30 cytosines (poly(C)-sequence), and a histone stem loop.

FIG. 7: C-enriched mRNA sequence of R2793 coding for *Photinus pyralis* luciferase (PpLuc), corresponding to SEQ ID NO:7. The vector used for in vitro transcription comprises a 5'-TOP-UTR derived from the ribosomal protein 32L, followed by a stabilizing sequence derived from the albumin-3'-UTR, a stretch of 64 adenosines (poly(A)-sequence), a stretch of 30 cytosines (poly(C)-sequence), and a histone stem loop.

Human PBMCs were treated with 10 μg/ml of GC- or C-enriched mRNA for 20 hours and the TNFα concentration was determined in the supernatant by ELISA as described in Example 2.

As can be seen, the treatment with C-enriched mRNA (R2793) results in significantly less TNFα secretion than treatment with GC-enriched mRNA (R2791). The statistical significance was assessed by the Mann Whitney test (p=0.03).

FIGS. 9A-B: Luciferase activity expressed by wild type or modified mRNAs.

Both RNAs were separately transfected into HeLa cells and luciferase activity (relative light units, RLU) was measured 6 h, 24 h and 48 h after transfection as described in Example 2.

(A) The luciferase activity of GC-enriched mRNA (R875) and C-optimized mRNA (R2103) was comparable both in terms of peak level and kinetics indicating a comparable expression level of the transfected mRNAs as a function of time.

(B) The luciferase activity of GC-enriched mRNA (R875) was much higher than that of the wild type construct (R873) indicating a significantly increased expression level of the modified G/C enriched mRNA.

Figure 10:
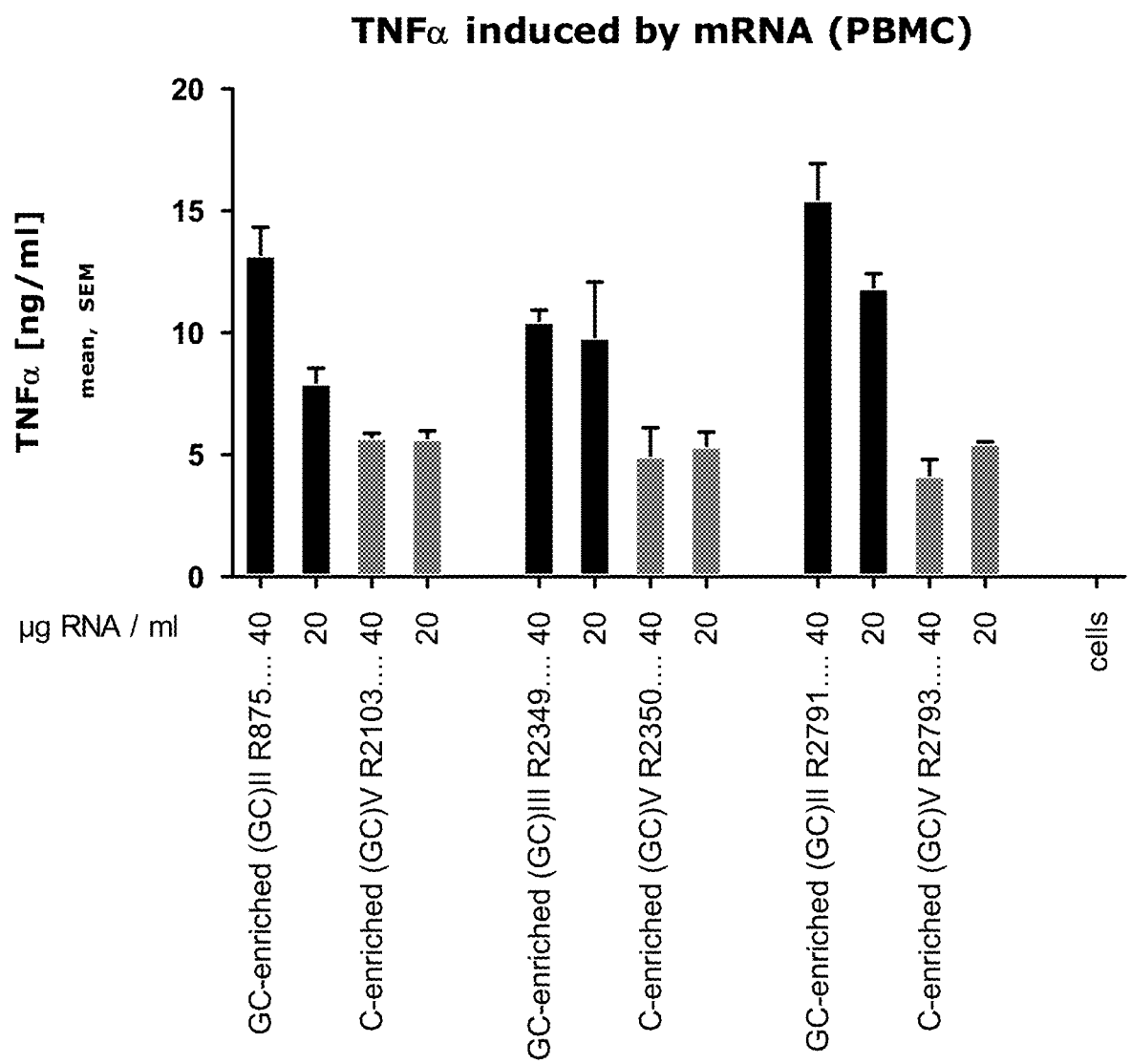

FIG. 10: Dose-response relationship for TNFα secretion of human PBMCs treated with different modified mRNAs.

Human PBMCs were treated with different concentrations of mRNAs (40 and 20 μg/ml) for 20 hours. The TNFα concentration as a parameter indicating the immune response evoked by the transfected mRNA in the immunologically competent PBMCs was determined by ELISA in the supernatants as described in Example 3. Treatment with C-optimized mRNA results in less TNFα secretion than treatment with GC-optimized mRNA. The mean and standard error of mean of triplicates are shown.

Figure 11:
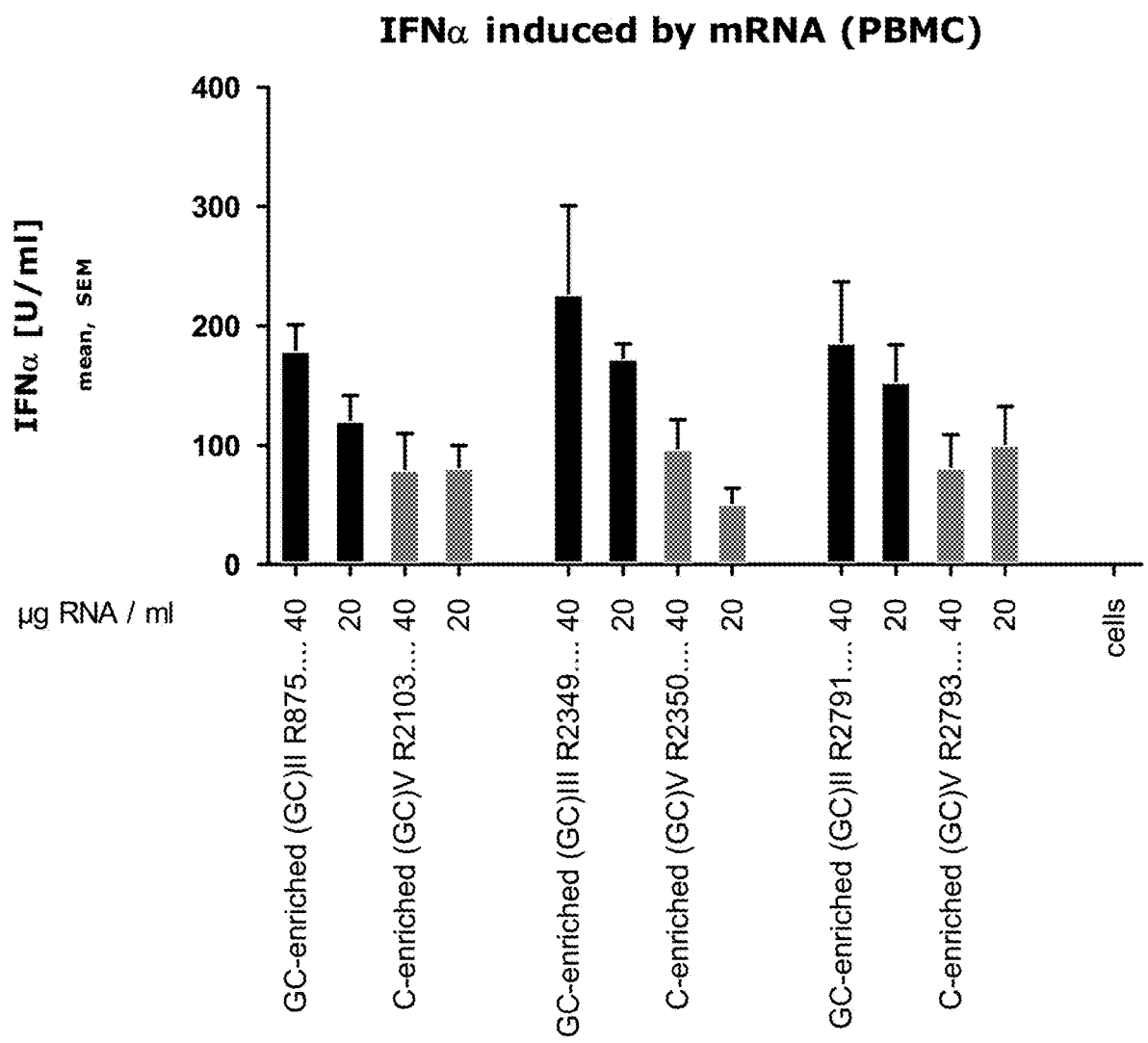

FIG. 11: Dose-response relationship for IFNα secretion of human PBMCs treated with various modified mRNAs.

Human PBMCs were treated with different concentrations of mRNAs (40 and 20 μg/ml) as indicated for 20 hours. The IFNα concentration was determined by ELISA in the supernatants as described in Example 3. Transfection of the PBMCs with C-optimized mRNA results in less IFNα secretion than transfection with GC-optimized mRNA. The mean and standard error of mean of triplicates are shown.

Table 1: List of luciferase constructs used for the production of the wild type (R873) and G/C- or C-enriched modified mRNA constructs used.

Table 2: Summary of the nucleotide composition and codon usage of the constructs used in the present Examples.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered as disclosed by the description of the present application, unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of".

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention is based on the surprising finding that the immune response against a target mRNA, which encodes at least one biologically active polypeptide or protein, can be modulated, i.e. reduced, by the inventive method of increasing the cytosine-content of the coding region of the mRNA. The inventive method hereby comprises the step of identifying a target wild type sequence, which encodes for at least one biologically active peptide, polypeptide or protein. As a second step, the target wild type sequence is modified, whereby at least 70% of the codons, or at least 80% of the codons, or more preferably at least 90%, or most preferably 100% of the wild type codons of the coding region, which are cytosine content-optimizable are modified such that the overall cytosine-content of the region of the modified mRNA coding for the peptide, polypeptide or protein is increased over the cytosine-content of the coding region of the wild type mRNA coding for the at least one peptide, polypeptide or protein. By that modification, the amino acid sequence encoded by the modified mRNA is unchanged compared to the wild type sequence.

Due to the naturally occuring degeneracy of the genetic code, more than one codon may encode a particular amino acid. Accordingly, 18 out of 20 naturally occuring amino acids are encoded by more than 1 codon (with Tryp and Met being an exception), e.g. by 2 codons (e.g. Cys, Asp, Glu), by three codons (e.g. Ile), by 4 codons (e.g. Al, Gly, Pro) or by 6 codons (e.g. Leu, Arg, Ser). However, not all codons encoding the same amino acid are utilized equally frequent under in vivo conditions. Depending on each single organism, a typical codon usage profile is established.

The term "cytosine content-optimizable codon" as used within the context of the present invention refers to codons, which exhibit a lower amount of cytosines than other codons coding for the same amino acid. Accordingly, any wild type codon, which may be replaced by another codon coding for the same amino acid and exhibiting a higher number of cytosines within that codon, is considered to be cytosine-optimizable (C-optimizable). Any such substitution of a C-optimizable wild type codon by the specific C-optimized codon within a wild type coding region increases its overall C-content and reflects a C-enriched modified mRNA sequence. A C-maximized mRNA sequence contains C-optimized codons for all potentially C-optimizable codons. Accordingly, 100% or all of the theoretically replaceable C-optimizable codons are under such conditions actually replaced by C-optimized codons over the entire length of the coding region.

Within the context of the present invention the preferred cell is a mammalian cell, more preferably a human cell. The codon usage frequency for the individual codons is provided in Table 2 of the appended examples. The term "coding region" as used in the present invention, i.e. the region in which the cytosine-content is increased by the use of cytosine-content optimized codons, corresponds to that portion of an RNA, such as, e.g. an mRNA, that codes for a peptide, polypeptide or protein. The coding region in mRNA may be bounded by the five prime untranslated region (5' UTR) and the three prime untranslated region (3' UTR).

Within the present invention, cytosine-content optimizable codons are codons, which contain a lower number of cytosines than other codons coding for the same amino acid.

Any of the codons GCG, GCA, GCU codes for the amino acid Ala, which may be exchanged by the codon GCC encoding the same amino acid, and/or
the codon UGU that codes for Cys may be exchanged by the codon UGC encoding the same amino acid, and/or
the codon GAU which codes for Asp may be exchanged by the codon GAC encoding the same amino acid, and/or
the codon that UUU that codes for Phe may be exchanged for the codon UUC encoding the same amino acid, and/or
any of the codons GGG, GGA, GGU that code Gly may be exchanged by the codon GGC encoding the same amino acid, and/or
the codon CAU that codes for His may be exchanged by the codon CAC encoding the same amino acid, and/or
any of the codons AUA, AUU that code for Ile may be exchanged by the codon AUC, and/or
any of the codons UUG, UUA, CUG, CUA, CUU coding for Leu may be exchanged by the codon CUC encoding the same amino acid, and/or
the codon AAU that codes for Asn may be exchanged by the codon AAC encoding the same amino acid, and/or
any of the codons CCG, CCA, CCU coding for Pro may be exchanged by the codon CCC encoding the same amino acid, and/or
any of the codons AGG, AGA, CGG, CGA, CGU coding for Arg may be exchanged by the codon CGC encoding the same amino acid, and/or
any of the codons AGU, AGC, UCG, UCA, UCU coding for Ser may be exchanged by the codon UCC encoding the same amino acid, and/or
any of the codons ACG, ACA, ACU coding for Thr may be exchanged by the codon ACC encoding the same amino acid, and/or
any of the codons GUG, GUA, GUU coding for Val may be exchanged by the codon GUC encoding the same amino acid, and/or
the codon UAU coding for Tyr may be exchanged by the codon UAC encoding the same amino acid.

In any of the above instances, the number of cytosines is increased by 1 per exchanged codon. Exchange of all non C-optimized codons (corresponding to C-optimizable codons) of the coding region results in a C-maximized coding sequence. According to the invention at least 70% of the non C-optimized codons are replaced by C-optimized codons of the wild type sequence are replaced by C-optimized codons, preferably at least 80%, more preferably at least 90% within the coding region.

It may be preferred that for some amino acids the percentage of C-optimizable codons replaced by C-optimized codons is less than 70%, while for other amino acids the percentage of replaced codons is higher than 70% to meet the overall percentage of C-optimization of at least 70% of all C-optimizable wild type codons of the coding region.

Preferably, in the C-optimized mRNAs of the invention, at least 50% of the C-optimizable wild type codons for any given amino acid are replaced by C-optimized codons, e.g. any modified C-enriched mRNA preferably contains at least 50% C-optimized codons at C-optimizable wild type codon positions coding for any single of the above mentioned amino acids Ala, Cys, Asp, Phe, Gly, His, Ile, Leu, Asn, Pro, Arg, Ser, Thr, Val and Tyr, preferably at least 60%.

According to the inventive method, codons coding for amino acids, which are not cytosine content-optimizable and which are, however, encoded by at least two codons, may be used without any further selection process. However, in a preferred embodiment of the invention the codon of the wild type sequence that codes for a relatively rare tRNA in the cell, e.g. a human cell, is exchanged for a codon that codes for a relatively frequent tRNA in the cell, whereby both code for the same amino acid. Accordingly, the relatively rare codon GAA coding for Glu may be exchanged by the relative frequent codon GAG coding for the same amino acid, and/or
the relatively rare codon AAA coding for Lys may be exchanged by the relative frequent codon AAG coding for the same amino acid, and/or
the relatively rare codon CAA coding for Gln is exchanged for the relative frequent codon CAG encoding the same amino acid.

In accordance with the present invention, the amino acids Met (AUG) and Trp (UGG), which are encoded by only one codon each, remain unchanged. Stop codons are not cytosine-content optimized, however, the relatively rare stop codons amber, ochre (UAA, UAG) may be exchanged by the relatively frequent stop codon opal (UGA).

The substitutions listed above may obviously be used individually but also in all possible combinations in order to optimize the cytosine-content of the modified mRNA compared to the wild type mRNA sequence.

Accordingly, the region of the modified mRNA coding for the polypeptide or protein is changed compared to the coding region of the polypeptide or protein of the wild type mRNA in such a way that an amino acid encoded by at least two or more codons, of which one comprises one additional cytosine, such a codon may be exchanged by the C-optimized codon comprising one additional cytosine, whereby the amino acid is unaltered compared to the wild type sequence.

In a preferred embodiment, the modified mRNA has—in addition to an increased C-content as defined above—an increased guanosine-content (G-content). In analogy to the modifications described above, which result in an increased C-content, corresponding modifications may additionally be introduced, which result in a higher G-content of the modified mRNA. Therein, a codon in the mRNA, which is guanosine-content optimizable, is replaced by a codon with a higher guanosine-content. Generally, the definitions and explanations provided above with respect to cytosine-optimizable codons and increased C-content apply to guanosine-optimizable codons and G-content in analogous manner. In the context of the present invention, guanosine-optimizable codons are codons, which contain a lower number of guanosines than other codons that are encoding the same amino acid.

In a further preferred embodiment, the modified mRNA is modified such that at least 10%, 20%, 30%, 40%, 50%, 60%, 70%, 80% or 90%, preferably at least 70% of the codons, which are not eligible for C-optimization, but which are guanosine-content optimizable, are replaced by a codon with a higher guanosine content, thus increasing the G-content of the modified mRNA.

Alternatively, the modified mRNA may be obtained by the following approach:

As a first step, its G/C content may be increased, e.g. by substituting wild type codons exhibiting a lower content of G and C nucleotides. At least 70%, more preferably at least 80%, more preferred at least 90%, or most preferred 100% of all wild type codons, which are G/C optimizable, may be replaced by that approach. G/C optimization is carried out as disclosed in WO2002098443 A2. As a second step, the G/C-enrichment or maximization is followed by a step of further C-optimization. Accordingly, the G/C optimized codons and/or the unaltered codons within the coding region are C-optimized by selecting codons, which exhibit a higher number of cytsines as compared to the codons occurring in the G/C-enriched mRNA. At least 70%, more preferably at least 80%, more preferably at least 90%, most preferred 100% of those GC-optimized and unaltered codons, which are C-optimizable, are replaced by that second step. The second step coincides with the first step (as described above for the embodiment starting with C-enrichment), but starts from a codon pattern, which is different from the wild type codon pattern. As a result, G/C maximization and subsequent C-maximization over the entire length of the coding region usually results in the same coding sequence as the alternative embodiment starting with C-maximization and subsequent G-maximization as described above.

According to a further embodiment of the present invention, the cytosine content of the coding region of the target mRNA coding for the polypeptide or protein is modified such that a maximal cytosine-content is achieved by introduction of codons, which code for tRNAs, which are relatively frequent within that particular cell, e.g. such as a mammalian cell, more specifically a human cell.

According to the inventive method for targeted modulation, preferably reduction, of the immune response against an mRNA, the cytosine content of the modified mRNA, which encodes at least one biologically active polypeptide or protein, is increased by at least 1-15%, preferably 5-10%, preferably by at least 10-15%, preferably by at least 10%, more preferably by at least 12.5%, more specifically by at least 15% compared to the cytosine content of the wild type sequence.

According to the present invention, it is thus particularly preferred to increase the cytosine content of the modified mRNA by the maximum amount possible, in particular in the coding region for the at least one peptide or polypeptide, compared to the wild type sequence.

Preferably, the nucleosides, which are introduced into the modified mRNA in order to increase the G and/or C content, are selected from the group consisting of adenosine, cytosine, guanosine and uridine. Preferably, the modified RNA is modified only with respect to its G and/or C content as described herein, wherein (non-modified) cytosine or guanosine replaces other nucleosides in order to increase the G and/or C content as described herein. Thus, no analogs of the nucleosides adenosine, cytosine, guanosine and uridine, preferably no nucleoside or ribonucleoside analogs as defined herein, are preferably used.

Preferably, the modified mRNA is not modified with a chemical modification at the 4-, 5- or 6-position of the pyrimidine base of the nucleosides of cytidine and/or uridine; a chemical modification at the 2-, 6-, 7- or 8-position of the purine base of the nucleosides of adenosine, inosine and/or guanosine; and/or a chemical modification at the 2'-position of the sugar of the nucleosides of adenosine, inosine, guanosine, cytidine and/or uridine.

More preferably, the modified mRNA is not modified with a chemical modification at the 2-, 6-, 7- or 8-position of the purine base of the nucleosides of adenosine, inosine and/or guanosine; and a chemical modification at the 2'-position of the sugar of the nucleosides of adenosine, inosine, guanosine, cytidine and/or uridine.

Even more preferably, the modified mRNA is not modified with a chemical modification at the 4-, 5- or 6-position of the pyrimidine base of the nucleosides of cytidine and/or uridine; and a chemical modification at the 2'-position of the sugar of the nucleosides of adenosine, inosine, guanosine, cytidine and/or uridine.

Preferably, the modified mRNA is not modified with a chemical modification at the 5- or 6-position of the pyrimidine base of the nucleosides cytidine and/or uridine, wherein the chemical modification is preferably selected from the group consisting of 4-thio, 5-iodo-/(5-I—), 5-bromo-/(5-Br—), 5-aminoallyl-, 5-fluoro-/(5-F—), 5-hydroxy-, 5-hydro-/(5-H—), 5-nitro-, 5-propynyl-/(5-(C☐C—CH3)-), 5-methyl-, 5-methyl-2-thio-, 5-formyl-, 5-hydroxymethyl-, 5-methoxy-, 5-oxyacetic acid methyl ester-, 5-oxyacetic acid-, 5-carboxyhydroxymethyl-, 5-(carboxyhydroxymethyl)pyrimidine methyl ester-, 5-methoxycarbonylmethyl-, 5-methoxycarbonylmethyl-2-thio, 5-aminomethyl-, 5-aminomethyl-2-thio-, 5-aminomethyl-2-seleno-, 5-methylaminomethyl-, 5-carbamoylmethyl-, 5-carboxymethylaminomethyl-, 5-carboxymethylaminomethyl-2-thio-, 5-carboxymethyl-, 5-methyldihydro-, 5-taurinomethyl-, 5-taurinomethyl-2-thiouridine, 5-isopentenylaminomethyl-, 5-isopentenylaminomethyl-2-thio-, 5-aminopropyl-/(5-(C3H6N-H3)-), 5-methoxy-ethoxy-methyl-/(5-(CH2-O—C2H4-O—CH3)-) and 6-aza-.

Further, the modified mRNA is not modified with a chemical modification at the 2-, 6-, 7- or 8-position of the purine base of the nucleosides adenosine, inosine and/or guanosine, wherein the chemical modification is preferably selected from the group consisting of 2-Amino-, 7-Deaza-, 8-Aza- and 8-Azido-.

In addition or alternatively, the modified mRNA is not modified with a chemical modification at the 2'-position of the sugar of the nucleosides adenosine, inosine, guanosine, cytidine and/or uridine, when incorporated in the RNA sequence, wherein such chemical modifications at the 2'-position of the sugar of the nucleosides adenosine, inosine, guanosine, cytidine and/or uridine may be selected from the group consisting of 2'-deoxy-, 2'-amino-2'-deoxy-/2'-amino-, 2'-fluoro-2'-deoxy-/2'-fluoro- and 2'-O-methyl-2'-deoxy-/2'-O-methyl-.

Preferably, the modified mRNA is not modified with a chemical modification at the 4-, 5- or 6-position of the base pyrimidine of the nucleosides cytidine and/or uridine and at the 2'-position of the ribose sugar as defined above, wherein the chemical modification is preferably selected from the group consisting of 4-thio-2'-deoxy-, 4-thio-2'-amino-, 4-thio-2'-fluoro-, 4-thio-2'-O-methyl-, 5-iodo-2'-deoxy-, 5-iodo-2'-amino-, 5-iodo-2'-fluoro-, 5-iodo-2'-O-methyl-, 5-bromo-2'-deoxy-, 5-bromo-2'-amino-, 5-bromo-2'-fluoro-, 5-bromo-2'-O-methyl-, 5-aminoallyl-2'-deoxy-, 5-aminoallyl-2'-amino-, 5-aminoallyl-2'-fluoro-, 5-aminoallyl-2'-O-methyl-, 5-fluoro-2'-deoxy-, 5-fluoro-2'-amino-, 5-fluoro-2'-fluoro-, 5-fluoro-2'-O-methyl-, 5-hydroxy-2'-deoxy-, 5-hydroxy-2'-amino-, 5-hydroxy-2'-fluoro-, 5-hydroxy-2'-O-methyl-, 5-hydro-2'-deoxy-, 5-hydro-2'-amino-, 5-hydro-2'-fluoro-, 5-hydro-2'-O-methyl-, 5-nitro-2'-deoxy-, 5-nitro-2'-amino-, 5-nitro-2'-fluoro-, 5-nitro-2'-O-methyl-, 5-propynyl-2'-deoxy-, 5-propynyl-2'-amino-, 5-propynyl-2'-fluoro-, 5-propynyl-2'-O-methyl-, 5-methyl-2'-deoxy-, 5-methyl-2'-amino-, 5-methyl-2'-fluoro-, 5-methyl-2'-O-methyl (5,2'-O-dimethyl)-, 5-methyl-2-thio-2'-deoxy-, 5-methyl-2-thio-2'-amino-, 5-methyl-2-thio-2'-fluoro-, 5-methyl-2-thio-2'-O-methyl-, 5-formyl-2'-deoxy-, 5-formyl-2'-amino-, 5-formyl-2'-fluoro-, 5-formyl-2'-O-methyl-, 5-hydroxymethyl-2'-deoxy-, 5-hydroxymethyl-2'-amino-, 5-hydroxymethyl-2'-fluoro-, 5-hydroxymethyl-2'-O-methyl-, 5-methoxy-2'-deoxy-, 5-methoxy-2'-amino-, 5-methoxy-2'-fluoro-, 5-methoxy-2'-O-methyl-, 5-oxyacetic acid methyl ester-2'-deoxy-, 5-oxyacetic acid methyl ester-2'-amino-, 5-oxyacetic acid methyl ester-2'-fluoro-, 5-oxyacetic acid methyl ester-2'-O-methyl-, 5-oxyacetic acid-2'-deoxy-, 5-oxyacetic acid-2'-amino-, 5-oxyacetic acid-2'-fluoro-, 5-oxyacetic acid-2'-O-methyl-, 5-carboxyhydroxymethyl-2'-deoxy-, 5-carboxyhydroxymethyl-2'-amino-, 5-carboxyhydroxymethyl-2'-fluoro-, 5-carboxyhydroxymethyl-2'-O-methyl-, 5-(carboxyhydroxymethyl)pyrimidine methyl ester-2'-deoxy-, 5-(carboxyhydroxymethyl)pyrimidine methyl ester-2'-amino-, 5-(carboxyhydroxymethyl)pyrimidine methyl ester-2'-fluoro-, 5-(carboxyhydroxymethyl)pyrimidine methyl ester-2'-O-methyl-, 5-methoxycarbonylmethyl-2'-deoxy-, 5-methoxycarbonylmethyl-2'-amino-, 5-methoxycarbonylmethyl-2'-fluoro-, 5-methoxycarbonylmethyl-2'-O-methyl-, 5-methoxycarbonylmethyl-2-thio 2'-deoxy-, 5-methoxycarbonylmethyl-2-thio 2'-amino-, 5-methoxycarbonylmethyl-2-thio 2'-fluoro-, 5-methoxycarbonylmethyl-2-thio 2'-O-methyl-, 5-aminomethyl-2'-deoxy-, 5-aminomethyl-2'-amino-, 5-aminomethyl-2'-fluoro-, 5-aminomethyl-2'-O-methyl-, 5-aminomethyl-2-thio-2'-deoxy-, 5-aminomethyl-2-thio-2'-amino-, 5-aminomethyl-2-thio-2'-fluoro-, 5-aminomethyl-2-thio-2'-O-methyl-, 5-aminomethyl-2-seleno-2'-deoxy-, 5-aminomethyl-2-seleno-2'-amino-, 5-aminomethyl-2-seleno-2'-fluoro-, 5-aminomethyl-2-seleno-2'-O-methyl-, 5-methylaminomethyl-2'-deoxy-, 5-methylaminomethyl-2'-amino-, 5-methylaminomethyl-2'-fluoro-, 5-methylaminomethyl-2'-O-methyl-, 5-carbamoylmethyl-2'-deoxy-, 5-carbamoylmethyl-2'-amino-, 5-carbamoylmethyl-2'-fluoro-, 5-carbamoylmethyl-2'-O-methyl-, 5-carboxymethylaminomethyl-2'-deoxy-, 5-carboxymethylaminomethyl-2'-amino-, 5-carboxymethylaminomethyl-2'-fluoro-, 5-carboxymethylaminomethyl-2'-O-methyl-, 5-carboxymethylaminomethyl-2-thio-2'-deoxy-, 5-carboxymethylaminomethyl-2-thio-2'-amino-, 5-carboxymethylaminomethyl-2-thio-2'-fluoro-, 5-carboxymethylaminomethyl-2-thio-2'-O-methyl-, 5-carboxymethyl-2'-deoxy-, 5-carboxymethyl-2'-amino-, 5-carboxymethyl-2'-fluoro-, 5-carboxymethyl-2'-O-methyl-, 5-methyldihydro-2'-deoxy-, 5-methyldihydro-2'-amino-, 5-methyldihydro-2'-fluoro-, 5-methyldihydro-2'-O-methyl-, 5-taurinomethyl-2'-deoxy-, 5-taurinomethyl-2'-amino-, 5-taurinomethyl-2'-fluoro-, 5-taurinomethyl-2'-O-methyl-, 5-taurinomethyl-2-thiouridine-2'-deoxy-, 5-taurinomethyl-2-thiouridine-2'-amino-, 5-taurinomethyl-2-thiouridine-2'-fluoro-, 5-taurinomethyl-2-thiouridine-2'-O-methyl-, 5-isopentenylaminomethyl-2'-deoxy-, 5-isopentenylaminomethyl-2'-amino-, 5-isopentenylaminomethyl-2'-fluoro-, 5-isopentenylaminomethyl-2'-O-methyl-, 5-isopentenylaminomethyl-2-thio-2'-deoxy-, 5-isopentenylaminomethyl-2-thio-2'-amino-, 5-isopentenylaminomethyl-2-thio-2'-fluoro-, 5-isopentenylaminomethyl-2-thio-2'-O-methyl-, 5-aminopropyl-2'-deoxy-, 5-aminopropyl-2'-amino-, 5-aminopropyl-2'-fluoro-, 5-aminopropyl-2'-O-methyl-, 5-methoxy-ethoxy-methyl-2'-deoxy-, 5-methoxy-ethoxy-methyl-2'-amino-, 5-methoxy-ethoxy-methyl-2'-fluoro-, 5-methoxy-ethoxy-methyl-2'-O-methyl-, 6-aza-2'-deoxy-, 6-aza-2'-amino-, 6-aza-2'-fluoro- and 6-aza-2'-O-methyl-.

More preferably, the modified mRNA is not modified with a chemical modification at the 2-, 6-, T- or 8-position of the purine base of the nucleosides adenosine, inosine and/or guanosine and at the 2'-position of the ribose sugar as defined above, wherein the chemical modification is selected from the group consisting of 2-Amino-2'-deoxy-, 2-Amino-2'-amino-, 2-Amino-2'-fluoro-, 2-Amino-2'-O-methyl-, 7-Deaza-2'-deoxy-, 7-Deaza-2'-amino-, 7-Deaza-2'-fluoro-, 7-Deaza-2'-O-methyl-, 8-Aza-2'-deoxy-, 8-Aza-2'-amino-, 8-Aza-2'-fluoro-, 8-Aza-2'-O-methyl-, 8-Azido-2'-deoxy-, 8-Azido-2'-amino-, 8-Azido-2'-fluoro- and 8-Azido-2'-O-methyl-.

According to the invention, the term polypeptide or protein refers to a peptide having at least 20, and preferably more than 50 amino acids. It may refer to a monomeric or multimeric protein. A peptide is understood to contain typically less than 20 amino acids.

According to the first embodiment of the present invention, the term "biologically active peptide, polypeptide or protein" refers to a polypeptide or protein that has the capability of performing one or more biological functions or a set of activities normally attributed to the polypeptide in a biological context. The biological activity may e.g. be a receptor binding activity, e.g. as a ligand, a catalytic activity, a transporter activity or an activity induced in cell structure proteins or modifications of cellular proteins, such as e.g. phosphorylation. The biological activity of the peptide, polypeptide or protein encoded by the wild type or by the modified mRNA according to the invention can be determined by any method available in the art. For example, the biological activity of members of the interferon family of proteins can be determined by any of a number of methods including their interaction with interferon-specific antibodies, their ability to increase resistance to viral infection, or their ability to modulate the transcription of interferon-regulated gene targets.

In a preferred embodiment, the biologically active peptide, polypeptide or protein does not comprise the gene product of a reporter gene or a marker gene. In the context of the present invention, the mRNA does preferably not encode, for instance, luciferase; green fluorescent protein (GFP) and its variants (such as eGFP, RFP or BFP); α-globin; hypoxanthine-guanine phosphoribosyltransferase (HGPRT); β-galactosidase; galactokinase; alkaline phosphatase; secreted embryonic alkaline phosphatase (SEAP)) or a resistance gene (such as a resistance gene against neomycin, puromycin, hygromycin and zeocin). In a preferred embodiment, the mRNA does not encode luciferase. In another embodiment, the mRNA does not encode GFP or a variant thereof.

In a further preferred embodiment, the biologically active peptide, polypeptide or protein does not comprise a protein (or a fragment of a protein) derived from a virus, preferably from a virus belonging to the family of Orthomyxoviridae. Preferably, the mRNA does not encode a protein that is derived from an influenza virus, more preferably an influenza A virus. Preferably, the mRNA does not encode an influenza A protein selected from the group consisting of hemagglutinin (HA), neuraminidase (NA), nucleoprotein (NP), matrix protein M1, matrix protein M2, NS1, NS2 (NEP: nuclear export protein), PA, PB1 (polymerase basic 1), PB1-F2 and PB2. In another preferred embodiment, the mRNA does not encode ovalbumin (OVA) or a fragment thereof. Preferably, the mRNA does not encode an influenza A protein or ovalbumin.

By the method according to the invention, an optimum balance of increased mRNA stability on the one hand and reduced immunostimulatory properties on the other hand is achieved. Increased C-content of the modified mRNA reduces the mRNA's immunogenicity and/or immunostimulatory capacity, while the increased C and G content contribute to increased mRNA stability. Increased mRNA stability means, e.g. increased in vivo functional stability resulting in an increased level of expressed protein over time. Accordingly, the in vivo AUC (area under the curve) of detectable protein upon mRNA administration is significantly increased for the inventive modified mRNA as compared to its wild type equivalent. Simultaneously, a reduced immune response in the patient is evoked (as determinable, for instance, by reduced amounts of cytokines secreted upon mRNA administration). The level of cytokine expression (secretion), e.g. TNF-α and IFN-α (e.g. by PBMCs) is reduced by at least 20%, preferably by at least 40%, as compared to the immune response triggered by the wild type equivalent. Such a reduction is measurable under in vivo and in vitro conditions.

According to the method of the present invention, the codon adaptation index of the modified target mRNA encoding at least one biologically active polypeptide or protein is increased by at least 0.05-0.5, or by at least 0.1-0.4, or by at least 0.2-0.3, or by at least 0.075-0.2, or by at least 0.1-0.2, or by at least 0.05, or by at least 0.1, or by at least 0.2, preferably by at least 0.125, more preferably by at least 0.15 compared to the CAI of the wild type mRNA.

The Codon Adaptation Index (CAI) is the most widespread technique for analyzing codon usage bias. The CAI provides an indication of gene expression level under the assumption that there is translational selection to optimize gene sequences according to their expression levels.

The codon adaptation index as used in the present invention can be calculated according to the method as published by Sharp and Li (Nucleic Acids Res. 1987 Feb. 11; 15(3): 1281-95). Software-implemented solutions for the calculation of the CAI are also known in prior art, such as e.g. "The CAI Analyser Package" (Ramazotti et al, In Silico Biol. 2007; 7(4-5):507-26) and are thus readily available to the skilled person. CAI is simply defined as the geometric mean of the weight associated to each codon over the length of the gene sequence (measured in codons). For each amino acid, the weight of each of its codons, in CAI, is computed as the ratio between the observed frequency of the codon and the frequency of the synonymous codon for that amino acid. The CAI uses a reference set of highly expressed genes from a species to determine relative merit of each codon to calculate a score for a gene from the frequency of use of all codons in said gene. This index is useful for predicting the level of expression of a gene and indicate likely success of heterologous gene expression in a given cell system.

Within the scope of the present invention, the term codon adaptation index (CAI) as used herein relates to the codon usage frequency of the genes encoding the at least one polypeptide or protein. Codon adaptation is the adaptation of the codons of an open reading frame to the synonymous codons preferred in human/mammalian genes whilst avoiding the introduction of unwanted secondary sequence functions that impede expression of the resulting open reading frames.

Within the context of the present invention, a CAI score of 1 means that the optimal codon is used for each amino acid in each codon position. Thus, according to the methods of the present invention, the coding region of the mRNA has a CAI which is greater than the CAI of the corresponding wild coding type sequence and the CAI of the modified mRNA is sufficiently close to 1, at least 0.6, more preferably at least 0.7, more preferably at least 0.8 and more preferably at least 0.9, such that the desired level of expression of the at least one biologically active polypeptide or protein is achieved. Accordingly the CAI of the modified mRNA is at least greater by 0.05-0.5, or at least greater by 0.1-0.4, or at least greater by 0.2-0.3, or at least greater by 0.075-0.2, or at least greater by 0.1-0.2, or at least greater by 0.05, or at least greater by 0.1, or at least greater by 0.2, preferably at least greater by 0.125, more preferably at least greater by 0.15, than the CAI of the wild type mRNA region coding for the at least one biologically active polypeptide or protein.

According to a preferred embodiment, the present invention provides a modified mRNA encoding at least one biologically active polypeptide or protein, which is obtainable or obtained by at least one or more embodiments of the inventive method of the present invention and wherein the modified mRNA is characterized by a reduced immunogenicity and/or immunostimulatory capacity compared to the wild type mRNA and may also be characterized by enhanced stability, in particular enhanced functional stability, as compared to the wild type equivalent.

In a more preferred embodiment of the present invention, the obtainable mRNA may further be subject to a step of determining the immunogenicity and/or immunostimulatory capacity of the inventive modified mRNA. Such a step comprises the e.g. in vitro sub-steps of transfecting competent cells, e.g. PBMCs, with the modified mRNA according to one or more embodiments of the inventive method, cultivating the cells, e.g. for 8 h-24 h, preferably for 12 h-48 h, preferably for 18 h-24 h, preferably for 24-48 h, preferably for at least 12 hours, preferably for at least 18 h, more preferably for at least 20 h and determining the amount of pro-inflammatory cytokines in the cell supernatant. The amount of pro-inflammatory cytokines present in the supernatant of the cells transfected with the modified mRNA according to the invention is compared to the amount of pro-inflammatory cytokines present in the supernatant of cells transfected with the wild type mRNA equivalent.

Appropriate techniques for determining the immunogenicity and/or immunostimulatory capacity of a nucleic acid, such as that of e.g. the inventive modified mRNA, are known in the art and are readily available to the skilled person (Robbins et al., 2009. Oligonucleotides 19(2):89-102). The nature and the extent of the cytokine response to RNA depends on several factors including timing, cell type, delivery vehicle and route of administration. The absence of immunostimulation at a single time point for a single cytokine does not necessarily demonstrate the absence of immunostimulation in general, such that assessment of several cytokine responses at multiple time points may be required. Antibodies and ELISA kits for the determination of interferons (e.g. IFNα and IFNβ) and a variety of pro-inflammatory cytokines, such as e.g. TNFα, TGFβ, IL-1 and IL-6, are commercially available.

If it were desired to carry out in vivo studies for testing for IFNα and/or suitable pro-inflammatory cytokines, such as e.g. TNFα and IL-6, their presence in the plasma of treated animals can be used to monitor the systemic activation of the immune response. Measurement of the immune response at an appropriate time point after mRNA administration is critical for a valid assessment. Systemic administration of mRNA formulations to mice leads to detectable elevations of serum cytokines within 1 to 2 hours, depending on the type of delivery vehicle and the cytokine of interest. Typically, the increase of cytokine levels in the serum is transient and may decrease again after 12 to 24 hours of treatment. For example, mice can be injected with complexed mRNA and serum levels of, e.g., IFNα, TNFα and IL-6 may be measured 6 hours post injection by using suitable ELISA assays (Kariko et al., 2012. Mol. Ther. 20(4948-53).

For in vitro studies, a similar panel of cytokines can be used to assess the stimulation of primary immune cell cultures after treatment with mRNA of the invention. The secretion of cytokines is cell type-dependent and therefore several cytokines may be required to be tested. The assessment of cytokine responses from in vitro cell cultures is less time critical compared to in vivo studies because the secreted cytokines tend to accumulate in the cell culture supernatant. Therefore, the measurement of cytokines at a single time point, such as between 8 h-24 h, or between 16-24 h, or between 12 h-48 h, or between 18 h-24 h, or between 24-48 h, preferably 12 hours, preferably 18 h, more preferably 20 h, after mRNA administration, such as e.g. the treatment with the modified mRNA according to the present invention, is often sufficient to detect an immune response. For example, a human in vitro whole blood assay (WBA) or peripheral blood mononuclear cell (PBMC) based assay can be used to assess the cytokine response elicited by treatment with modified mRNA molecules of the invention (Coch et al., 2013. PLoS One 8(8):e71057), as exemplified in the appended examples, in particular Example 2. Alternatively, primary myeloid and plasmacytoid dendritic cells (pDCs) can be isolated from peripheral blood using commercially available cell isolation kits and are treated with mRNA of the invention, such as the modified mRNA according to the invention, in cell culture. After 8 to 20 hours of incubation cytokine levels (e.g. IFNα, TNFα and/or IL-8) in the cell culture medium may be determined with ELISA assays. In addition, the activation status of DCs may be analyzed by measuring cell surface expression of activation markers (e.g. CD80, CD83, CD86 and MHC class II) by flow cytometry (Kariko et al., 2005. Immunity 23(2):165-75).

Alternatively, activation of the cytosolic RNA sensor RIG-I in cells can be assessed by treating cells with modified mRNA of the invention, generating cell lysates, separating proteins by SDS-polyacrylamide gel electrophoresis and probing for phosphorylation of PKR by Western blotting. Phosphorylation of PKR on threonine at position 446 (pT446) is required for PKR activation and thus represents an activation marker. In addition, the phosphorylation of the alpha subunit of eukaryotic protein synthesis initiation factor-2 (EIF2-alpha), which is a physiological substrate for PKR, can be assessed with an antibody directed at phosphorylated serine at position 51 (pS51) (Anderson et al., 2010. Nucleic Acids Res. 38(17):5884-92).

The activation of 2'-5' oligoadenylate synthetase (OAS) by RNA can be tested in an enzyme assay. The assay for OAS can be performed by the measurement of the 2-5(A) products. Using [$^3$H]ATP in the synthetase reaction, the conversion of 2-5(A) is measured by digestion of the reaction products with alkaline phosphatase. This converts [$^3$H] 2-5(A) to core (A2'p)$_n$A, which is negatively charged and binds to DEAE-cellulose paper. Residual [$^3$H]ATP is converted to adenosine which is uncharged and removed by washing. This assay is suitable to measure OAS activity in crude cell extracts as well as that of purified OAS (Sharp et al., 1999. Virology 257(2):303-13; Anderson et al., 2011. Nucleic Acids Res. 39(21):9329-38).

Typically, the inventive modified mRNA obtainable according to one or more embodiments of the inventive method for targeted modulation of the immune response against an mRNA is characterized by lower affinity to one or more of TLR3, TLR7, TLR8, MDA5, RIG-I, LGP2 or 2'-5'-oligoadenylate synthetase compared to the wild type mRNA encoding the same peptide, polypeptide or protein.

The term "affinity" as used herein relates to the ability of an RNA, such as e.g. the modified mRNA of the invention, to bind to and/or to function as a ligand and/or activate signaling events by one or more of TLR3, TLR7, TLR8, MDA5, RIG-I, LGP2 or 2'-5'-oligoadenylate synthetase. Thus, RNA, such as the modified mRNA of the present invention, which is characterized by lower affinity to one or more of TLR3, TLR7, TLR8, MDA5, RIG-I, LGP2 or 2'-5'-oligoadenylate synthetase will result in a reduced production of pro-inflammatory cytokines, such as, e.g. TNFα, TGFβ, IL-1 or IL-6. The affinity may be reduced by at least 50%, preferably by at least 60%, as compared to the affinity of the wild type equivalent.

Thus, the affinity of the modified mRNA of the present invention to one or more of TLR3, TLR7, TLR8, MDA5, RIG-I, LGP2 or 2'-5'-oligoadenylate synthetase is correlated with the amount of pro-inflammatory cytokines produced in any one of the above assays, i.e. a reduced affinity and/or activation of one or more of TLR3, TLR7, TLR8, MDA5, RIG-I, LGP2 or 2'-5'-oligoadenylate synthetase is correlated with a reduced amount of pro-inflammatory cytokines released into the cell supernatant compared to the amount of pro-inflammatory cytokines, such as, e.g. TNFα, TGFβ, IL-1 or IL-6, produced in response to transfection of corresponding wild type mRNA encoding the at least one biologically active polypeptide or protein.

In a preferred embodiment, the inventive method of targeted modulation of the immune response against an mRNA encoding at least one biologically active polypeptide or protein according to the present invention may be executed on a computer with the aid of suitable software by way of executing at least one algorithm thereon.

Computer software for sequence analysis and/or codon optimization is known in prior art and is readily accessible to the skilled person. Computer programs, which may be used to execute the at least one algorithm of the inventive method may include, e.g. CodonW, GCUA, INCA, etc. Also, several software packages that are available online may be used, such as e.g. the "JCat" available on the world wide web at jcat.de/. The at least one algorithm may, e.g. comprise the following steps:

1. Providing the wild type target mRNA sequence, such as e.g. the entire mRNA or a portion thereof. Go to step 2.
2. Generate a novel modified mRNA sequence by modifying the target sequence according to the method as provided in any one of claims 1-11. Go to step 3.
3. Evaluate the modified mRNA sequence and determine if it has a predetermined property, e.g. at least 70% of the codons of the wild type mRNA sequence, which are cytosine content optimizable, have been modified to the maximum C-content possible without altering the amino acid sequence compared to the wild type sequence. If the modified mRNA sequence has the predetermined property, then proceed to step 4, otherwise proceed to step 2.

4. Providing the modified mRNA sequence as an optimized and modified mRNA.

The modified mRNA sequence obtained by the above algorithm may then be used as a template for e.g. chemical RNA synthesis or in vitro transcription.

According to a further embodiment the inventive modified mRNA coding for at least one biologically active peptide, polypeptide or protein may be obtained by synthesis, such as e.g. chemical synthesis.

Defined chemical synthesis of the modified mRNA of the invention in the 3'→5' direction is well established in prior art. The technology utilizes a ribonucleoside with suitable N-protecting group: generally 5'-Protecting group, the most popular being dimethoxytriphenyl, i.e. the DMT group; T-protecting group, out of which most popular is t-Butyldimethylsilyl ether; and, a 3'-phosphoramidite, the most popular of which is cyanoethyl diisopropyl (component 1). This component is then coupled with a nucleoside with a suitable N-protecting group, 2' or 3' succinate of a ribonucleoside attached to a solid support (component 2). The coupling of component 1 and 5'-OH-n-protected-2',3'-protected-nucleoside (component 3) are also achieved in solution phase in presence of an activator leading to dimers and oligoribonucleotides, followed by oxidation (3'→5' direction synthesis), also leads to a protected dinucleotide having a 3'-5'-internucleotide linkage (Ogilvie, K. K., Can. J. Chem., 58, 2686, 1980). Other technologies for chemical RNA synthesis, i.e. for the synthesis of the modified RNA according to the invention are known in prior art, such as, e.g. the method disclosed in US 20110275793 A1.

According to a more preferred embodiment, the modified mRNA according to the inventive method of the present invention may be obtained by in vitro transcription, preferably by bacteriophage-mediated in vitro transcription, preferably by Sp6 polymerase in vitro transcription and/or T3 polymerase-mediated in vitro transcription, more preferably by T7 polymerase-mediated in vitro transcription.

Highly efficient in vitro transcription systems have been developed in prior art, particularly ones using phage polymerases such as T7, SP6, and T3. The DNA-dependent phage T7, T3, and SP6 RNA polymerases are widely used to synthesize a large quantity of RNAs. These enzymes are highly processive and are thus capable of generating long RNA molecules of up to thousands of nucleotides in length with low probability of falling off DNA templates during transcription and may thus be used for in vitro transcription in the present invention. Phage RNA polymerases specifically recognize their 18-bp promoter sequences (T7, 5'-TAATACGACTCACTATAG (SEQ ID NO: 8); T3, 5'-AATTAACCCTCACTAAAG (SEQ ID NO: 9); and SP6, 5'-ATTTAGGTGACACTATAG (SEQ ID NO: 10)) and initiate transcription precisely at the 18th nucleotide guanosine. With a T7, T3, or SP6 promoter fused to the 5' end of a DNA template, the transcription reaction is expected to generate an RNA molecule with the predicted sequence.

In this method, a DNA molecule corresponding to the modified mRNA of the present invention is transcribed in vitro for the production of the mRNA. This DNA matrix has a suitable promoter, for example a T7 and/or SP6 and/or T3 promoter, for the in vitro transcription, followed by the desired nucleotide sequence for the mRNA to be produced and a termination signal for the in vitro transcription. According to the invention the DNA molecule that forms the matrix of the RNA construct to be produced, such as e.g. the modified mRNA according to the present invention is prepared by fermentative replication and subsequent isolation as part of a plasmid replicable in bacteria.

Suitable plasmids for in vitro transcription of the modified mRNA according to the present invention are known in the art and are commercially available. For example the following plasmids may be mentioned as examples pT7 Ts (GeneBank Accession No. U26404), the pGEM® series, for example pGEM®-1 (GeneBank Accession No. X65300) and pSP64 (GeneBank-Accession No. X65327); see also Mezei and Storts, Purification of PCR Products, in: Griffin and Griffin (Eds.), PCR Technology: Current Innovation, CRC Press, Boca Raton, Fla., 2001. The in vitro transcription of the modified mRNA according to the present invention may also include ribonucleoside triphosphates (rNTPs) analogues, such as those, e.g. required for 5' capping of the in vitro transcribed modified mRNA according to the invention. rNTP analogues other than those naturally present in mRNAs, in particular mammalian mRNAs, such as e.g. human mRNAs, should not be used for in vitro transcription, since the mRNA of the inventive mRNA may be disadvantageously affected and, more importantly, if the in vitro transcribed inventive mRNA is to be used in protein replacement therapy, this may not be in accordance with national regulatory affairs.

According to a more preferred embodiment, the modified mRNA that is obtainable by the method according to the present invention may be synthesized by in vitro transcription including naturally occurring rNTP analogues, for example 5-methyl-cytidine triphosphate and/or pseudouridine triphosphate.

According to a further preferred embodiment, the modified mRNA obtainable by the inventive method may be synthesized by in vitro transcription, including other than naturally occurring rNTP analogues.

The term "ribonucleoside triphosphate analogues" as used herein refers to ribonucleoside triphosphate compounds comprising a chemical modification, wherein the chemical modification may comprise a backbone modification, a sugar modification, or a base modification. These ribonucleoside triphosphate analogues are also termed herein as modified nucleoside triphosphates, modified ribonucleosides or modified nucleosides.

In this context, the modified nucleoside triphosphates as defined herein are nucleotide analogs/modifications, e.g. backbone modifications, sugar modifications or base modifications. A backbone modification in the context of the present invention is a modification, in which phosphates of the backbone of the nucleotides are chemically modified. A sugar modification in the context of the present invention is a chemical modification of the sugar of the nucleotides. Furthermore, a base modification in the context of the present invention is a chemical modification of the base moiety of the nucleotides. In this context nucleotide analogs or modifications are preferably selected from nucleotide analogs, which are applicable for transcription and/or translation.

Sugar Modifications

The modified nucleosides and nucleotides, which may be used in the context of the present invention, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH2CH20)nCH2CH2OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration with respect to that of the corresponding carbon in ribose. Thus, a modified nucleotide can include nucleotides containing, for instance, arabinose as the sugar.

Backbone Modifications

The phosphate backbone may further be modified in the modified nucleosides and nucleotides. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications

The modified nucleosides and nucleotides, which may be used in the present invention, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogs/modifications are selected from base modifications, which are preferably selected from 2-amino-6-chloropurineriboside-5'-triphosphate, 2-Aminopurine-riboside-5'-triphosphate; 2-aminoadenosine-N-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-N-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadeno sine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyluridine, 1-carboxymethyl-pseudouridine, 5-propynyluridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguano sine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments the modified nucleotides include nucleoside modifications selected from 6-aza-cytidine, 2-thio-cytidine, □-thio-cytidine, Pseudo-iso-cytidine, 5-aminoallyl-uridine, 5-iodo-uridine, N1-methyl-pseudouridine, 5,6-dihydrouridine, ☐-thio-uridine, 4-thio-uridine, 6-aza-uridine, 5-hydroxy-uridine, deoxy-thymidine, 5-methyl-uridine, Pyrrolo-cytidine, inosine, ☐-thio-guanosine, 6-methyl-guanosine, 5-methyl-cytdine, 8-oxo-guanosine, 7-deaza-guano sine, N1-methyl-adenosine, 2-amino-6-Chloro-purine, N6-methyl-2-amino-purine, Pseudo-iso-cytidine, 6-Chloro-purine, N6-methyl-adenosine, ☐-thio-adenosine, 8-azido-adenosine, 7-deaza-adenosine.

Further modified nucleotides have been described previously (WO2013052523).

In some embodiments of the present invention, the modified mRNA obtainable by the method according to the invention does not comprise any modified nucleosides as described above. In these embodiments, the modified mRNA preferably comprises exclusively nucleosides, which are selected from the group consisting of adenosine, cytosine, guanosine and uridine. Preferably, the modified mRNA is modified only with respect to its G and/or C content as described herein, wherein (non-modified) cytosine or guanosine replaces other nucleosides in order to increase the G and/or C content as described herein.

Preferably, the modified mRNA that is obtainable by the method according to the invention has not been modified with a chemical modification at the 4-, 5- or 6-position of the pyrimidine base of the nucleosides of cytidine and/or uridine; a chemical modification at the 2-, 6-, 7- or 8-position of the purine base of the nucleosides of adenosine, inosine and/or guanosine; and/or a chemical modification at the 2'-position of the sugar of the nucleosides of adenosine, inosine, guanosine, cytidine and/or uridine.

More preferably, the modified mRNA that is obtainable by the method according to the invention has not been modified with a chemical modification at the 2-, 6-, 7- or 8-position of the purine base of the nucleosides of adenosine, inosine and/or guanosine; and a chemical modification at the 2'-position of the sugar of the nucleosides of adenosine, inosine, guanosine, cytidine and/or uridine.

Even more preferably, the modified mRNA that is obtainable by the method according to the invention has not been modified with a chemical modification at the 4-, 5- or 6-position of the pyrimidine base of the nucleosides of cytidine and/or uridine; and a chemical modification at the 2'-position of the sugar of the nucleosides of adenosine, inosine, guanosine, cytidine and/or uridine.

Preferably, the modified mRNA that is obtainable by the method according to the invention has not been modified with a chemical modification at the 5- or 6-position of the pyrimidine base of the nucleosides cytidine and/or uridine, wherein the chemical modification is preferably selected from the group consisting of 4-thio, 5-iodo-/(5-I—), 5-bromo-/(5-Br—), 5-aminoallyl-, 5-fluoro-/(5-F—), 5-hydroxy-, 5-hydro-/(5-H—), 5-nitro-, 5-propynyl-/(5-(C☐C—CH3)-), 5-methyl-, 5-methyl-2-thio-, 5-formyl-, 5-hydroxymethyl-, 5-methoxy-, 5-oxyacetic acid methyl ester-, 5-oxyacetic acid-, 5-carboxyhydroxymethyl-, 5-(carboxyhydroxymethyl)pyrimidine methyl ester-, 5-methoxycarbonyl-methyl-, 5-methoxycarbonylmethyl-2-thio, 5-aminomethyl-, 5-aminomethyl-2-thio-, 5-aminomethyl-2-seleno-, 5-methylaminomethyl-, 5-carbamoylmethyl-, 5-carboxymethylaminomethyl-, 5-carboxymethylaminomethyl-2-thio-, 5-carboxymethyl-, 5-methyldihydro-, 5-taurinomethyl-, 5-taurinomethyl-2-thiouridine, 5-isopentenylaminomethyl-, 5-isopentenylaminomethyl-2-thio-, 5-aminopropyl-/(5-(C3H6NH3)-), 5-methoxy-ethoxy-methyl-/(5-(CH2-O—C2H4-O—CH3)-) and 6-aza-.

Further, the modified mRNA that is obtainable by the method according to the invention has preferably not been modified with a chemical modification at the 2-, 6-, 7- or 8-position of the purine base of the nucleosides adenosine, inosine and/or guanosine, wherein the chemical modification is preferably selected from the group consisting of 2-Amino-, 7-Deaza-, 8-Aza- and 8-Azido-.

In addition or alternatively, the modified mRNA that is obtainable by the method according to the invention has preferably not been modified with a chemical modification at the 2'-position of the sugar of the nucleosides adenosine, inosine, guanosine, cytidine and/or uridine, when incorporated in the RNA sequence, wherein such chemical modifications at the 2'-position of the sugar of the nucleosides adenosine, inosine, guanosine, cytidine and/or uridine may be selected from the group consisting of 2'-deoxy-, 2'-amino-2'-deoxy-/2'-fluoro-2'-deoxy-/2'-fluoro- and 2'-O-methyl-2'-deoxy-/2'-O-methyl-.

Preferably, the modified mRNA that is obtainable by the method according to the invention has not been modified with a chemical modification at the 4-, 5- or 6-position of the base pyrimidine of the nucleosides cytidine and/or uridine and at the 2'-position of the ribose sugar as defined above, wherein the chemical modification is preferably selected from the group consisting of 4-thio-2'-deoxy-, 4-thio-2'-amino-, 4-thio-2'-fluoro-, 4-thio-2'-O-methyl-, 5-iodo-2'-deoxy-, 5-iodo-2'-amino-, 5-iodo-2'-fluoro-, 5-iodo-2'-O-methyl-, 5-bromo-2'-deoxy-, 5-bromo-2'-amino-, 5-bromo-2'-fluoro-, 5-bromo-2'-O-methyl-, 5-aminoallyl-2'-deoxy-, 5-aminoallyl-2'-amino-, 5-aminoallyl-2'-fluoro-, 5-aminoallyl-2'-O-methyl-, 5-fluoro-2'-deoxy-, 5-fluoro-2'-amino-, 5-fluoro-2'-fluoro-, 5-fluoro-2'-O-methyl-, 5-hydroxy-2'-deoxy-, 5-hydroxy-2'-amino-, 5-hydroxy-2'-fluoro-, 5-hydroxy-2'-O-methyl-, 5-hydro-2'-deoxy-, 5-hydro-2'-amino-, 5-hydro-2'-fluoro-, 5-hydro-2'-O-methyl-, 5-nitro-2'-deoxy-, 5-nitro-2'-amino-, 5-nitro-2'-fluoro-, 5-nitro-2'-O-methyl-, 5-propynyl-2'-deoxy-, 5-propynyl-2'-amino-, 5-propynyl-2'-fluoro-, 5-propynyl-2'-O-methyl-, 5-methyl-2'-deoxy-, 5-methyl-2'-amino-, 5-methyl-2'-fluoro-, 5-methyl-2'-O-methyl (5,2'-O-dimethyl)-, 5-methyl-2-thio-2'-deoxy-, 5-methyl-2-thio-2'-amino-, 5-methyl-2-thio-2'-fluoro-, 5-methyl-2-thio-2'-O-methyl-, 5-formyl-2'-deoxy-, 5-formyl-2'-amino-, 5-formyl-2'-fluoro-, 5-formyl-2'-O-methyl-, 5-hydroxymethyl-2'-deoxy-, 5-hydroxymethyl-2'-amino-, 5-hydroxymethyl-2'-fluoro-, 5-hydroxymethyl-2'-O-methyl-, 5-methoxy-2'-deoxy-, 5-methoxy-2'-amino-, 5-methoxy-2'-fluoro-, 5-methoxy-2'-O-methyl-, 5-oxyacetic acid methyl ester-2'-deoxy-, 5-oxyacetic acid methyl ester-2'-amino-, 5-oxyacetic acid methyl ester-2'-fluoro-, 5-oxyacetic acid methyl ester-2'-O-methyl-, 5-oxyacetic acid-2'-deoxy-, 5-oxyacetic acid-2'-amino-, 5-oxyacetic acid-2'-fluoro-, 5-oxyacetic acid-2'-O-methyl-, 5-carboxyhydroxymethyl-2'-deoxy-, 5-carboxyhydroxymethyl-2'-amino-, 5-carboxyhydroxymethyl-2'-fluoro-, 5-carboxyhydroxymethyl-2'-O-methyl-, 5-(carboxyhydroxymethyl)pyrimidine methyl ester-2'-deoxy-, 5-(carboxyhydroxymethyl)pyrimidine methyl ester-2'-amino-, 5-(carboxyhydroxymethyl)pyrimidine methyl ester-2'-fluoro-, 5-(carboxyhydroxymethyl)pyrimidine methyl ester-2'-O-methyl-, 5-methoxycarbonylmethyl-2'-deoxy-, 5-methoxycarbonylmethyl-2'-amino-, 5-methoxycarbonylmethyl-2'-fluoro-, 5-methoxycarbonylmethyl-2'-O-methyl-, 5-methoxycarbonylmethyl-2-thio 2'-deoxy-, 5-methoxycarbonylmethyl-2-thio 2'-amino-, 5-methoxycarbonylmethyl-2-thio 2'-fluoro-, 5-methoxycarbonylmethyl-2-thio 2'-O-methyl-, 5-aminomethyl-2'-deoxy-, 5-aminomethyl-2'-amino-, 5-aminomethyl-2'-fluoro-, 5-aminomethyl-2'-O-methyl-, 5-aminomethyl-2-thio-2'-deoxy-, 5-aminomethyl-2-thio-2'-amino-, 5-aminomethyl-2-thio-2'-fluoro-, 5-aminomethyl-2-thio-2'-O-methyl-, 5-aminomethyl-2-seleno-2'-deoxy-, 5-aminomethyl-2-seleno-2'-amino-, 5-aminomethyl-2-seleno-2'-fluoro-, 5-aminomethyl-2-seleno-2'-O-methyl-, 5-methylaminomethyl-2'-deoxy-, 5-methylaminomethyl-2'-amino-, 5-methylaminomethyl-2'-fluoro-, 5-methylaminomethyl-2'-O-methyl-, 5-carbamoylmethyl-2'-deoxy-, 5-carbamoylmethyl-2'-amino-, 5-carbamoylmethyl-2'-fluoro-, 5-carbamoylmethyl-2'-O-methyl-, 5-carboxymethylaminomethyl-2'-deoxy-, 5-carboxymethylaminomethyl-2'-amino-, 5-carboxymethylaminomethyl-2'-fluoro-, 5-carboxymethylaminomethyl-2'-O-methyl-, 5-carboxymethylaminomethyl-2-thio-2'-deoxy-, 5-carboxymethylaminomethyl-2-thio-2'-amino-, 5-carboxymethylaminomethyl-2-thio-2'-fluoro-, 5-carboxymethylaminomethyl-2-thio-2'-O-methyl-, 5-carboxymethyl-2'-deoxy-, 5-carboxymethyl-2'-amino-, 5-carboxymethyl-2'-fluoro-, 5-carboxymethyl-2'-O-methyl-, 5-methyldihydro-2'-deoxy-, 5-methyldihydro-2'-amino-, 5-methyldihydro-2'-fluoro-, 5-methyldihydro-2'-O-methyl-, 5-taurinomethyl-2'-deoxy-, 5-taurinomethyl-2'-amino-, 5-taurinomethyl-2'-fluoro-, 5-taurinomethyl-2'-O-methyl-, 5-taurinomethyl-2-thiouridine-2'-deoxy-, 5-taurinomethyl-2-thiouridine-2'-amino-, 5-taurinomethyl-2-thiouridine-2'-fluoro-, 5-taurinomethyl-2-thiouridine-2'-O-methyl-, 5-isopentenylaminomethyl-2'-deoxy-, 5-isopentenylaminomethyl-2'-amino-, 5-isopentenylaminomethyl-2'-fluoro-, 5-isopentenylaminomethyl-2'-O-methyl-, 5-isopentenylaminomethyl-2-thio-2'-deoxy-, 5-isopentenylaminomethyl-2-thio-2'-amino-, 5-isopentenylaminomethyl-2-thio-2'-fluoro-, 5-isopentenylaminomethyl-2-thio-2'-O-methyl-, 5-aminopropyl-2'-deoxy-, 5-aminopropyl-2'-amino-, 5-aminopropyl-2'-fluoro-, 5-aminopropyl-2'-O-methyl-, 5-methoxy-ethoxy-methyl-2'-deoxy-, 5-methoxy-ethoxy-methyl-2'-amino-, 5-methoxy-ethoxy-methyl-2'-fluoro-, 5-methoxy-ethoxy-methyl-2'-O-methyl-, 6-aza-2'-deoxy-, 6-aza-2'-amino-, 6-aza-2'-fluoro- and 6-aza-2'-O-methyl-.

More preferably, the modified mRNA that is obtainable by the method according to the invention has not been modified with a chemical modification at the 2-, 6-, 7- or 8-position of the purine base of the nucleosides adenosine, inosine and/or guanosine and at the 2'-position of the ribose sugar as defined above, wherein the chemical modification is selected from the group consisting of 2-Amino-2'-deoxy-, 2-Amino-2'-amino-, 2-Amino-2'-fluoro-, 2-Amino-2'-O-methyl-, 7-Deaza-2'-deoxy-, 7-Deaza-2'-amino-, 7-Deaza-2'-fluoro-, 7-Deaza-2'-O-methyl-, 8-Aza-2'-deoxy-, 8-Aza-2'-amino-, 8-Aza-2'-fluoro-, 8-Aza-2'-O-methyl-, 8-Azido-2'-deoxy-, 8-Azido-2'-amino-, 8-Azido-2'-fluoro- and 8-Azido-2'-O-methyl-.

According to a further embodiment, the modified mRNA, which is obtained according to one or more embodiments of the inventive method of targeted modulation of the immune response against an mRNA, is devoid of destabilizing sequence elements (DSE) in the 3' and/or 5' UTR.

As used herein, the term "destabilizing sequence element" (DSE) refers to a sequence of nucleotides, which reduces the half-life of a transcript, e.g. the half-life of the inventive modified mRNA inside a cell and/or organism, e.g. a human. Accordingly, a DSE comprises a sequence of nucleotides, which reduces the intracellular half-life of an RNA transcript.

DSE sequences are found in short-lived mRNAs such as, for example; c-fos, c-jun, c-myc, GM-CSF, IL-3, TNF-alpha, IL-2, IL-6, IL-8, IL-10, Urokinase, bcl-2, SGLT1 (Na(+)-coupled glucose transporter), Cox-2 (cyclooxygenase 2), IL8, PAI-2 (plasminogen activator inhibitor type 2), beta1-adrenergic receptor, GAP43 (5'UTR and 3'UTR).

AU-rich elements (AREs) and/or U-rich elements (UREs), including but not limited to single, tandem or multiple or overlapping copies of the nonamer UUAUUUA(U/A)(U/A) (where U/A is either an A or a U) and/or the pentamer AUUUA and/or the tetramer AUUU. Accordingly, the DNA template used for in vitro transcription of the modified mRNA according to the present invention are devoid of the corresponding sequences.

Assays for measuring RNA degradation, such as e.g. degradation of the modified mRNA of the invention and thus the stability of the inventive modified mRNA are known in the art. For example, RNA half-life can be measured by the methods described by Duan and Jefcoate (Duan and Jefcoate, 2007. J. Mol. Endocrinol. 38(1-4159-79).

According to this method, cells may e.g. be plated in 12-well plates at 25% density 24 hours prior to transfection. For transfection 1 µg of modified mRNA of the invention may be transfected per well. The following proportion may be used: 1 µg mRNA, 1 µl TransIt-mRNA reagent, 1 µl mRNA boost reagent and 100 µl serum-free media. The modified mRNA of the invention may then first be mixed with serum-free media, then RNA boost reagent may be added and mixed, followed by the addition of transfection reagent. The mixture may then be incubated at room temperature for three minutes and aliquoted directly onto cells in, e.g. complete media. Twelve hours after transfection, when cell mRNA levels have reached a steady state, cells may be washed once and cell culture medium may be exchanged for complete medium devoid of the transfection reagents (mixture) (zero hour time point). The degradation of the modified mRNA of the invention within the cells may then be determined by harvesting cells at appropriate time points, such as e.g. 12 h and/or 16 h and/or 18 h and/or 20 h and/or 24 and/or 48 h post transfection. Total cellular RNA may subsequently be isolated and the amount of modified mRNA of the invention may be determined by reverse transcription and/or quantitative real-time PCR using specific primers that bind to the coding region of the modified mRNA of the invention and/or the 5' and/or 3' UTRs of the modified mRNA. The half-life of the modified mRNA of the invention may then be calculated by linear regression fit of the time points on semi-log plots.

In a preferred embodiment the inventive modified mRNA may further comprise a 5'-CAP structure and/or a polyA-tail of at least 60 nucleotides, more preferably of at least 70 nucleotides and/or a 3' stabilizing sequence.

Within the present invention the term "CAP structure" refers to a structure found on the 5'-end of an mRNA, such as e.g. the modified mRNA according to one or more embodiments of the method of present invention and generally consists of a guanosine nucleotide connected to the mRNA via an unusual 5' to 5' triphosphate linkage. The guanosine nucleotide is methylated on the 7-position directly after capping in vivo by a methyl transferase. It is referred to as a 7-methylguanylate cap, abbreviated m7G. Further modifications include the possible methylation of the 2' hydroxy-groups of the first 2 ribose sugars of the 5' end of the mRNA.

For an efficient translation of a given mRNA, such as e.g. the modified mRNA according to the invention, an effective binding of ribosomes to the ribosome binding site, which is also referred to as "Kozak sequence" (5'-GCCGCCAC-CAUGG (SEQ ID NO: 11), wherein the AUG denotes the start codon) is necessary. In this regard it has been established that an increased A/U content around this site permits a more efficient ribosome binding to the mRNA (Kozak, Mol Cell Biol. 1989 November; 9(11):5073-80). Accordingly, the inventive modified mRNA may comprise a Kozak sequence for more efficient ribosome binding to the mRNA. The inventive modified mRNA may further comprise a poly-A tail, which is a sequence of up to 200 adenosine nucleotides located at the 3' end of the mRNA.

According to a further embodiment of the present invention, the inventive modified mRNA may comprise in the 3' non-translated region one or more stabilisation sequences that are capable of increasing the half-life of the mRNA in the cytosol. These stabilisation sequences may exhibit a 100% sequence homology with naturally occurring sequences that are present in viruses, bacteria and eukaryotic cells, but may however also be partly or completely synthetic. As an example of stabilising sequences that may be used in the present invention, the non-translated sequences (UTR) of the β-globin gene, for example of *Homo sapiens* or *Xenopus laevis*, may be mentioned. Another example of a stabilisation sequence has the general formula (C/U)CCANxCCC(U/A)PyxUC(C/U)CCU (SEQ ID NO: 12), which is contained in the 3'UTR of the very stable mRNA that codes for α-globin, α-(I)-collagen, 15-lipoxygenase or for tyrosine hydroxylase (c.f. Holcik et al., Proc. Natl. Acad. Sci. USA 1997, 94: 2410 to 2414). Such stabilisation sequences may be used individually or in combination with one another for stabilizing the inventive modified mRNA as well as in combination with other stabilisation sequences known to the person skilled in the art.

According to a preferred embodiment, the present invention provides for a pharmaceutical composition comprising a modified mRNA according to one or more of the above embodiments of the present invention, or the inventive modified mRNA according to one or more of the above embodiments. The pharmaceutical composition optionally comprises one or more pharmaceutically acceptable excipients, carriers, diluents and/or vehicles.

The term "pharmaceutically acceptable" as used in connection with the pharmaceutical compositions of the invention, refers to molecular entities and compositions that are physiologically tolerable and do not typically produce untoward reactions when administered to an individual, such as e.g. a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" as used in connection with the pharmaceutical compositions of the invention refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The term "pharmaceutically acceptable" refers to the non-toxicity of a material which does not interact with the action of the active component, i.e. with the action of the inventive modified mRNA of the pharmaceutical composition.

Suitable excipients and/or vehicles for use with the pharmaceutical composition of the present invention are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art, such as those, e.g. which are disclosed in e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. A non-limiting list of commonly used and accepted excipients is also provided in "VOLUME 3B Guidelines Medicinal products for human use Safety, environment and information Excipients in the label and package leaflet of medicinal products for human use, July 2003" issued by the European Commission, which is hereby incorporated in its entirety into the disclosure of this invention. The composition or formulation to be administered will, in any event, contain a quantity of the agent adequate to achieve the desired state in the subject being treated.

Possible carrier substances for use with the pharmaceutical composition of the present invention for parenteral administration are e.g. sterile water, sterile sodium chloride solution, polyalkylene glycols, hydrogenated naphthalenes and, in particular, biocompatible lactide polymers, lactide/glycolide copolymers or polyoxyethylene/polyoxypropylene copolymers. The pharmaceutical composition according to may further comprise filler substances or substances such as lactose or mannitol. Preferred carriers for use in the inventive pharmaceutical composition are typically aqueous carrier materials, water for injection (WFI) or water buffered with phosphate, citrate, HEPES or acetate etc. being used, and the pH is typically adjusted to 5.0 to 8.0, preferably 6.5 to 7.5. The carrier or the vehicle will additionally preferably comprise salt constituents, e.g. sodium chloride, potassium chloride or other components which render the solution e.g. isotonic. Furthermore, the carrier or the vehicle can contain, in addition to the abovementioned constituents, additional components, such as human serum albumin (HSA), polysorbate 80, sugars or amino acids.

In a more preferred embodiment the present invention provides for a pharmaceutical composition comprising the modified mRNA according to one or more embodiments of the inventive method for use in the treatment of diseases amenable to protein replacement therapy, e.g. for the treatment of hereditary or endocrinological diseases, preferably for use in the treatment of diseases caused by amino acid disorders, carbohydrate metabolism disorders, cholesterol biosynthesis disorders, fatty acid oxidation defects and fat metabolism disorders, lactic acidosis, glycogen storage diseases, mitochondrial disorders, organic acid disorders, urea cycle disorders, lysosomal storage disease disorders.

The term "protein replacement therapy" as used herein refers to the introduction of an mRNA, such as e.g. the modified of the invention into an individual having a deficiency in a protein encoded by the modified mRNA according to the invention, i.e. an mRNA modified by the inventive method of targeted modulation of the immune response against said mRNA coding for at least one biologically active polypeptide or protein.

Accordingly, the pharmaceutical composition of the invention, which comprises the modified mRNA according to one or more embodiments of the inventive method may be used in the treatment of diseases or in aiding in the treatment of the diseases which are characterized by a protein deficiency.

The term "diseases which are characterized by a protein deficiency" as used in the context of the present invention, such as e.g. in the context of the pharmaceutical composition comprising the modified mRNA of the invention refers to any disorder that presents with a pathology caused by absent or insufficient amounts of a protein. This term encompasses protein folding disorders, i.e., conformational disorders, that result in a biologically inactive protein product. Protein insufficiency can be involved in infectious diseases, immunosuppression, organ failure, glandular problems, radiation illness, nutritional deficiency, poisoning, or other environmental or external insults.

There are currently about 1100 known inherited disorders characterized by protein deficiency or loss-of-function in specific tissue. These disorders may be treatable by protein replacement therapy in theory, e.g. the method of the present invention contemplates therapy for proteins currently suited for use in protein replacement therapy that is available now or will be in the future. In such disorders, certain cells or all of the cells of an individual lack a sufficient functional protein, contain an inactive form of the protein or contain insufficient levels for biological function.

Further, the list of diseases identified as being conformational disorders, caused by mutations that alter protein folding and retardation of the mutant protein in the ER, resulting in protein deficiency, is increasing. These include cystic fibrosis, a1-antitrypsin deficiency, familial hypercholesterolemia, Fabry disease, Alzheimer's disease (Selkoe, Annu. Rev. Neurosci. 1994; 17:489-517), osteogenesis imperfecta (Chessler et al., J. Biol. Chem. 1993; 268:18226-18233), carbohydrate-deficient glycoprotein syndrome (Marquardt et al., Eur. J. Cell. Biol. 1995; 66: 268-273), Maroteaux-Lamy syndrome (Bradford et al., Biochem. J. 1999; 341:193-201), hereditary blindness (Kaushal et al., Biochemistry 1994; 33:6121-8), Glanzmann thrombasthenia (Kato et al., Blood 1992; 79:3212-8), hereditary factor VII deficiency (Arbini et al., Blood 1996; 87:5085-94), oculocutaneous albinism (Halaban et al., Proc. Natl. Acad. Sci. USA. 2000; 97:5889-94) and protein C deficiency (Katsumi, et al., Blood 1996; 87:4164-75). Recently, one mutation in the X-linked disease adrenoleukodystrophy (ALD), resulted in misfolding of the defective peroxisome transporter which could be rescued by low-temperature cultivation of affected cells (Walter et al., Am J Hum Genet 2001; 69:35-48). It is generally accepted that mutations take place evenly over the entire sequence of a gene. Therefore, it is predictable that the phenotype resulting from misfolding of the deficient protein exists in many other genetic disorders.

Many of the inherited protein deficient disorders are enzyme deficiencies. As indicated above, a large class of inherited-enzyme disorders involves mutations in lysosomal enzymes and are referred to as lysosomal storage disorders (LSDs). Lysosomal storage disorders are a group of diseases caused by the accumulation of glycosphingolipids, glycogen, mucopolysaccharides Examples of lysosomal disorders include but are not limited to Gaucher disease (Beutler et al., The Metabolic and Molecular Bases of Inherited Disease, 8th ed. 2001 Scriver et al., ed. pp. 3635-3668, McGraw-Hill, New York), GM1-gangliosidosis (id. at pp 3775-3810), fucosidosis (The Metabolic and Molecular Bases of Inherited Disease 1995. Scriver, C. R., Beaudet, A. L., Sly, W. S. and Valle, D., ed pp. 2529-2561, McGraw-Hill, New York), mucopolysaccharidoses (id. at pp 3421-3452), Pompe disease (id. at pp. 3389-3420), Hurler-Scheie disease (Weismann et al., Science 1970; 169, 72-74), Niemann-Pick A and B diseases, (The Metabolic and Molecular Bases of Inherited Disease 8th ed. 2001. Scriver et al. ed., pp 3589-3610, McGraw-Hill, Now York), and Fabry disease (id. at pp. 3733-3774).

Fabry disease is an X-linked inborn error of glycosphingolipid metabolism caused by deficient lysosomal α-galactosidase A (α-Gal A) activity (Desnick et al., The Metabolic and Molecular Bases of Inherited Disease, 8th Edition Scriver et al. ed., pp. 3733-3774, McGraw-Hill, New York 2001; Brady et al., N. Engl. J. Med. 1967; 276, 1163-1167). This enzymatic defect leads to the progressive deposition of neutral glycosphingolipids with α-galactosyl residues, predominantly globotriaosylceramide (GL-3), in body fluids and tissue lysosomes. The frequency of the disease is estimated to be about 1:40,000 in males, and is reported throughout the world within different ethnic groups. In classically affected males, the clinical manifestations include angiokeratoma, acroparesthesias, hypohidrosis, and characteristic corneal and lenticular opacities (The Metabolic and Molecular Bases of Inherited Disease, 8th Edition 2001, Scriver et al., ed., pp. 3733-3774, McGraw-Hill, New York). The affected male's life expectancy is reduced, and death usually occurs in the fourth or fifth decade as a result of vascular disease of the heart, brain, and/or kidneys. In contrast, patients with the milder "cardiac variant" normally have 5-15% of normal α-Gal A activity, and present with left ventricular hypertrophy or a cardiomyopathy. These cardiac variant patients remain essentially asymptomatic when their classically affected counterparts are severely compromised. Recently, cardiac variants were found in 11% of adult male patients with unexplained left ventricular hypertrophic cardiomyopathy, suggesting that Fabry disease may be more frequent than previously estimated (Nakao et al., N. Engl. J. Med. 1995; 333: 288-293). The α-Gal A gene has been mapped to Xq22, (Bishop et al., Am. J. Hum. Genet. 1985; 37: A144), and the full-length cDNA and entire 12-kb genomic sequences encoding α-Gal A have been reported (Calhoun et al., Proc. Natl. Acad Sci. USA 1985; 82: 7364-7368; Bishop et al., Proc. Natl. Acad. Sci. USA 1986; 83: 4859-4863; Tsuji et al., Bur. J. Biochem. 1987; 165: 275-280; and Kornreich et al., Nucleic Acids Res. 1989; 17: 3301-3302). There is a marked genetic heterogeneity of mutations that cause Fabry disease (The Metabolic and Molecular Bases of Inherited Disease, 8th Edition 2001, Scriver et al., ed, pp. 3733-3774, McGraw-Hill, New York; Eng et al., Am. J. Hum. Genet. 1993; 53: 1186-1197; Eng et al., Mol. Med. 1997; 3:174-182; and Davies et al., Bur. J. Hum. Genet. 1996; 4: 219-224). To date, a variety of missense, nonsense, and splicing mutations, in addition to small deletions and insertions, and larger gene rearrangements have been reported.

Gaucher disease is a deficiency of the lysosomal enzyme β-glucocerebrosidase that breaks down fatty glucocerebrosides. The fat then accumulates, mostly in the liver, spleen and bone marrow. Gaucher disease can result in pain, fatigue, jaundice, bone damage, anemia and even death. There are three clinical phenotypes of Gaucher disease. Patients with, Type 1 manifest either early in life or in young adulthood, bruise easily and experience fatigue due to anemia, low blood platelets, enlargement of the liver and spleen, weakening of the skeleton, and in some instances have lung and kidney impairment. There are no signs of brain involvement. In Type II, early-onset, liver and spleen enlargement occurs by 3 months of age and there is extensive brain involvement. There is a high mortality rate by age 2. Type III is characterized by liver and spleen enlargement and brain seizures. The β-glucocerebrosidase gene is located on the human 1q21 chromosome. Its protein precursor contains 536 amino acids and its mature protein is 497 amino acids long.

Gaucher disease is considerably more common in the descendants of Jewish people from Eastern Europe (Ashkenazi), although individuals from any ethnic group may be affected. Among the Ashkenazi Jewish population, Gaucher disease is the most common genetic disorder, with an incidence of approximately 1 in 450 persons. In the general public, Gaucher disease affects approximately 1 in 100,000 persons. According to the National Gaucher Foundation, 2,500 Americans suffer from Gaucher disease.

Glucose-6-phosphate dehydrogenase (G6PD) deficiency is the most common X-linked human enzyme deficiency. The G6PD enzyme catalyzes an oxidation/reduction reaction that is essential for the production of ribose, which is an essential component of both DNA and RNA. G6PD also involved in maintaining adequate levels of NADPH inside the cell. NADPH is a required cofactor in many biosynthetic reactions. Individuals with this deficiency have clinical symptoms including neonatal jaundice, abdominal and/or back pain, dizziness, headache, dyspnea (irregular breathing), and palpitations.

Additional examples of diseases amenable to protein replacement therapy, which may be treated with the pharmaceutical composition of the present invention, e.g. a pharmaceutical composition comprising a modified mRNA according to one or more of the embodiments of the present invention, include lysosomal storage disease disorders, such as, e.g. activator deficiency/GM2, gangliosidosis, alpha-mannosidosis, aspartylglucosaminuria, cholesteryl ester storage disease, chronic Hexosaminidase A deficiency, cystinosis, Danon disease, Farber disease, fucosidosis, galactosialidosis, Gaucher DiseaseType I, II, III; GM1 gangliosidosis, Infantile/late infantile/juvenile/adult/chronic I-Cell disease/Mucolipidosis II, infantile Free Sialic Acid Storage Disease/ISSD, juvenile hexosaminidase A deficiency, Krabbe disease, infantile onset/late onset lysosomal acid lipase deficiency, early onset/late onset metachromatic Leukodystrophy, mucopolysaccharidoses disorders, pseudo-Hurler polydystrophy/Mucolipidosis MA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV, Multiple sulfatase deficiency, Niemann-Pick Disease, Type A/Type B/Type C neuronal ceroid lipofuscinoses, CLN6 disease, atypical late infantile/late onset variant/early juvenile Batten-Spielmeyer-Vogt/Juvenile NCL/CLN3 disease, Finnish Variant Late Infantile CLN5, Jansky-Bielschowsky disease/ Late infantile CLN2/TPP1 Disease, Kufs/Adult-onset NCL/ CLN4 disease, Northern Epilepsy/variant late infantile CLN8, Santavuori-Haltia/Infantile CLN1/PPT disease, beta-mannosidosis, Pompe disease/Glycogen storage disease type II, pycnodysostosis, Sandhoff disease/Adult Onset/ GM2 gangliosidosis, Sandhoff disease/GM2 gangliosidosis—Infantile, Sandhoff disease/GM2 gangliosidosis—Juvenile, Schindler disease, Salla disease/Sialic Acid Storage Disease, Tay-Sachs/GM2 gangliosidosis, Wolman disease, and/or amino acid metabolism disorders, such as, e.g. alkaptonuria, aspartylglucosaminuria, methylmalonic acidemia, maple syrup urine disease, homocystinuria, tyrosinemia, trimethylaminuria, Hartnup disease, biotinidase deficiency, ornithine carbamoyltransferase deficiency, carbamoyl-phosphate synthase I deficiency disease, citrullinemia, hyperargininemia, hyperhomocysteinemia, hypermethioninemia, hyperlysinemias, nonketotic hyperglycinemia, propionic acidemia, hyperprolinemia, and/or carbohydrate metabolism disorders, such as e.g. lactose intolerance, other disorders of carbohydrate metabolism, glycogen storage disease, glycogen storage disease type I (von Gierke's disease), glycogen storage disease type II (Pompe's disease), glycogen storage disease type III, glycogen storage disease type IV, glycogen storage disease type V (McArdle's disease), disorders of fructose metabolism, essential fructosuria, fructose-1,6-diphosphatase deficiency, hereditary fructose intolerance, disorders of galactose metabolism, galactosaemia, galactokinase deficiency, disorders of intestinal carbohydrate absorption, e.g. glucose-galactose malabsorption, sucrase deficiency, disorders of pyruvate metabolism and gluconeogenesis, e.g. deficiency of phosphoenolpyruvate carboxykinase, deficiency of pyruvate carboxylase, deficiency of pyruvate dehydrogenase, other disorders of carbohydrate metabolism, such as, e.g. essential pentosuria, oxalosis, oxaluria, renal glycosuria, and/or lipid and cholesterol biosynthesis disorders, such as, e.g. pure hypercholesterolaemia, familial hypercholesterolaemia, Fredrickson's hyperlipoproteinaemia, type IIa, hyperbetalipoproteinaemia, hyperlipidaemia, group A, low-density-lipoprotein-type (LDL) hyperlipoproteinaemia, hyperglyceridaemia, endogenous hyperglyceridaemia, Fredrickson's hyperlipoproteinaemia, type IV, hyperlipidaemia, group B, hyperprebetalipoproteinaemia very-low-density-lipoprotein-type (VLDL) hyperlipoproteinaemia, and/or lactic acidosis caused by e.g. glucose-6-phosphatase deficiency, fructose 1,6-diphosphatase deficiency, pyruvate dehydrogenase deficiency, pyruvate carboxylase deficiency, and/or glycogen storage diseases (GSDs), e.g. GSD type I, GSD type II, GSD type III, GSD type IV, GSD type V, GSD type VI, GSD type VII, GSD type VIII, GSD type IX, GSD type X, GSD type XI, and/or mitochondrial disorders, such as, e.g. Kearns-Sayre syndrome, mitochondrial encephalopathy, lactic acidosis and stroke-like episodes (MELAS syndrome), mitochondrial neurogastrointestinal encephalopathy syndrome (MNGIE), myoclonus with epilepsy and with ragged red fibers (MERRF syndrome), neuropathy, ataxia, and retinitis pigmentosa (NARP syndrome), and/or organic acid disorders, such as, e.g. glutaric acidemia type 1, type 2, hyperlysinemia, pipecolic acidemia, saccharopinuria, and/or urea cycle disorders, such as, e.g. citrullinemia, hyperammonemia.

In addition to inherited disorders, the pharmaceutical composition according to the invention may be used in and/or used in aiding in the treatment of other enzyme deficiencies, which arise from damage to a tissue or organ resulting from primary or secondary disorders. For example, damaged pancreatic tissue, or pancreatitis, is caused by alcoholism results in a deficiency in pancreatic enzymes necessary for digestion. Pancreatitis is currently being treated using enzyme replacement therapy.

In addition to disorders characterized by protein deficiencies, some disorders may be treated by the pharmaceutical composition of the present invention to replace proteins in order to enhance or stimulate biological processes. For example, currently individuals with anemia are administered recombinant erythropoietin (EPOGEN®, PROCRIT®, EPOIETIN®) to stimulate red blood cell production and increase oxygen transportation to tissues. In addition, recombinant interferons such as interferon alpha 2b (INTRON A®, PEG-INTRON®, or REBETOL®), and interferon beta 1a (AVONEX®, BETASERON®) are administered to treat hepatitis B and multiple sclerosis, respectively. Still other proteins administered are recombinant human deoxyribonuclease I (rhDNase-PULMOZYME®), an enzyme which selectively cleaves DNA used to improve pulmonary function in patients with cystic fibrosis; recombinant thyroid stimulating hormone (THYROGEN®) developed for use in thyroid cancer patients who have had near-total or total thyroidectomy, and who must therefore take thyroid hormones; recombinant G-CSF (NEUPOGEN®) for treating neutropenia from chemotherapy, and digestive enzymes in individuals with pancreatitis. Thus, the pharmaceutical composition of the present invention may be used in the treatment of the above mentioned conditions.

Additionally, the pharmaceutical composition according to the invention may be used in the treatment of and/or used in aiding in the treatment of growth hormone deficiency, such as e.g. pituitary-related growth hormone deficiency, growth hormone releasing hormone (GHRH) deficiency. Accordingly, the pharmaceutical composition according to the present invention may be used in treating or aiding in the treatment of the above diseases.

The pharmaceutical composition of the invention comprising the modified mRNA according to one or more embodiments of the inventive method may also be used in another area of protein replacement therapy, such as, e.g. in the treatment of infectious diseases and cancer with antibodies, which have a highly specific, well-defined active site. Accordingly, the pharmaceutical composition of the invention may comprise a modified mRNA of the invention, which codes for an antibody for use in the treatment of cancer or infectious diseases. The antibodies encoded by the modified mRNA of the invention comprised in the pharmaceutical composition may be e.g. any type of antibody, however, in a preferred embodiment the encoded antibody is a single chain Fv fragments (scFv), preferably an intrabody.

The term "intrabody" or "intrabodies" as used herein refers to intracellularly expressed antibodies. For example, whole antibodies, heavy chains, Fab' fragments, single chain antibodies and diabodies can be used as intrabodies, preferably the intrabody is a single chain antibody.

The pharmaceutical composition comprising a modified mRNA of the invention, which codes for an antibody, such as, e.g. a single-chain Fv fragments (scFv) may be administered to a patient in need thereof, preferably a therapeutically effective amount of the pharmaceutical composition is administered. The cancer can include, e.g. breast, colon, ovarian, endometrial, gastric, pancreatic, prostate and salivary gland cancer. The administration of the pharmaceutical composition of the invention can be by any of a variety of convenient methods including, e.g. systemic injectable administration, injection into a tumor or cancerous tissue, oral administration.

According to another embodiment the present invention provides a method of treating a subject in need of protein replacement therapy comprising administering to a subject in need thereof a pharmaceutically effective amount of the pharmaceutical composition according to one or more embodiments of the present invention or an effective amount of the modified mRNA, which has been modified in accordance to one or more of the embodiments of the inventive method.

The mode and method of administration and the dosage of the pharmaceutical composition according to the invention depends on several factors, such as e.g. on the nature of the disease to be cured, also the body weight, the age and the sex of the patient and the route of administration of the inventive pharmaceutical composition.

The pharmaceutical composition according to the present invention composition may be administered to an individual in need thereof, for example, a patient, by any suitable administration route, such as by oral, topical, rectal, vaginal, dermal, intra-tumoural, nasal, lingual, parenteral administration or administration by inhalation, insufflation, injection, infusion or by enema. Thus, the modified mRNA obtainable by one or more embodiments of the inventive method for targeted modulation of the immunogenicity and/or immunostimulatory capacity of said mRNA, the pharmaceutical composition according to the present invention may be adapted, for example, for oral, topical, rectal, vaginal, dermal, intra-tumoural, nasal, lingual, parenteral administration or administration by inhalation, insufflation, injection, infusion or by enema.

Furthermore, the method of treatment according to the present invention may comprise oral, topical, rectal, vaginal, dermal, intra-tumoural, nasal, lingual, parenteral administration or administration by inhalation, insufflation, injection, infusion or by enema. Preferred administration routes are oral and parenteral administration, such as intravenous, intramuscular, subcutaneous, intranodal, intralymphatic, intra-tumoural or intraperitoneal injection or transdermal delivery.

More preferably, the present invention provides a method for expressing a biologically active peptide, polypeptide or protein in a tissue in vivo, the method comprising contacting the patient with a pharmaceutical composition according to one or more of the above embodiments of the invention, or contacting the patient with the inventive modified mRNA according to any one of the above embodiments of the invention, wherein administering the pharmaceutical composition or the modified mRNA results in a reduced innate immune response by the patient relative to a patient contacted with the wild type mRNA molecule encoding the same polypeptide or protein. Typically, the level of mRNA expression in vivo is increased by the modified target mRNA of the invention as compared to the wild type mRNA.

Further embodiments of the present invention are provided by the items as specified below:

item 22. Modified mRNA that codes for at least one biologically active peptide polypeptide or protein, wherein
    the cytosine-content of the coding region of the modified mRNA is larger than the cytosine-content of the coding region of the wild type mRNA coding for the polypeptide or protein whereby the encoded amino acid sequence is unchanged compared to the wild type sequence and optionally
    if no cytosine is present in any of the at least one codon coding for the amino acid, the at least one codon of the wild type sequence that codes for a relatively rare tRNA in the cell is exchanged for a codon that codes for a relatively frequent tRNA in the cell that carries the same amino acid as the relatively rare tRNA.

item 23. Modified mRNA according to item 22, wherein all codons of the wild type sequence, which code for a relatively rare codon in the cell, have been replaced by codons which code a relatively frequent tRNA in the cell, which carries the same amino acid as the relatively rare tRNA.

item 24. Modified mRNA according to item 22 or item 23, wherein the cytosine-content of the polypeptide- or protein-coding region of the modified mRNA is at least 10%, preferably at least 12.5%, more preferred at least 15% greater than the cytosine content compared to the polypeptide or protein coding region of the wild type mRNA.

item 25. Modified mRNA according to any one of items 22-24, wherein the coding region of the modified mRNA is modified such that a maximal cytosine-content is achieved by means of codons which encode relatively frequent tRNAs.

item 26. Modified mRNA according to any one of items 22-25, wherein the codon adaptation index (CAI) of the region coding for the polypeptide or protein is greater by at least 0.05, preferably greater by at least 0.1, preferably greater by at least 0.125, more preferred greater by at least 0.15 than the CAI of the wild type region of the mRNA coding for the polypeptide or protein.

item 27. Modified mRNA according to any one of items 22-26, wherein the coding region of the modified mRNA and/or the 5' and/or 3' untranslated region of the modified mRNA is changed in comparison to the polypeptide- or protein-encoding wildtype region such that no destabilizing elements are present.

item 28. Modified mRNA according to any one of items 22-27, wherein the modified mRNA is characterized by having a 5' CAP structure and/or a polyA-tail of at least 70 nucleotides and/or a 3' stabilizing sequence.

item 29. Modified mRNA according to any one of items 22-28, wherein the modified mRNA coding for the polypeptide or protein is characterized by a lower binding affinity to mammalian cellular RNA sensors than the wild type sequence coding for the polypeptide or protein, wherein the mammalian cellular RNA sensors comprise one or more of TLR3, TLR7, TLR8, PKR, MDA5, RIG-I, LGP2, 2'-5'-oligoadenylate synthetase item 30—Modified mRNA according to any one of items 22-29, wherein the modified mRNA encodes a polypeptide or protein for use in protein replacement therapy.

item 31. Modified mRNA according to any one of items 22-30, wherein the modified mRNA encodes for a polypeptide or protein selected from the group of α-glucosidase, acid β-glucosidase, α-galactosidase A, galactocerebrosidase Acid α-Mannosidase, Acid β-Mannosidase, Acid α-L-fucosidase, α-N-Acetylgalactosaminidase, β-Hexosaminidase A, β-Hexosaminidase B, α-L-Iduronidase, β-Glucuronidase, Sialidase, Iduronate sulfatase, Acid sphingomyelinase, pituitary-related growth hormone, growth hormone releasing hormone (GHRH), erythropoetin, or thyroid stimulating hormone.

item 32. Modified mRNA according to any one of items 22-31, for use in protein replacement therapy.

item 33. Kit of parts for use in aiding in protein replacement therapy, wherein the kit comprises
 (i) the isolated and purified mRNA according to any one of items 22-31,
 (ii) means for applying the mRNA to an individual, e.g. a human.

SEQUENCE LISTING

SEQ ID NO:1 R873, *Photinus pyralis* luciferase wild type mRNA
SEQ ID NO:2 R875, G/C-enriched mRNA sequence
SEQ ID NO:3 R2103, C-enriched mRNA sequence
SEQ ID NO:4 R2349, G/C-enriched mRNA sequence
SEQ ID NO:5 R2350, C-optimized mRNA sequence
SEQ ID NO:6 R2791, G/C-enriched mRNA sequence
SEQ ID NO:7 R2793, C-optimized mRNA sequence

EXAMPLES

Example 1: Preparation of mRNA

Preparation of DNA and mRNA Constructs

For the present examples DNA sequences encoding the *Photinus pyralis* luciferase were prepared and used for subsequent in vitro transcription reactions.

According to a first preparation, the DNA sequences coding for the mRNAs shown in Table 1 were prepared.

The G/C-enriched sequences of the examples provided were obtained according to the method as disclosed in WO2002098443 A2. The C-enriched modified mRNA coding region was obtained by the method of the present invention. However, alternatively, the C-enriched mRNA of the examples included may also be obtained according to the alternative embodiment as disclosed above, i.e. in a first step, the G/C content may be increased, e.g. by substituting wild type codons exhibiting a lower content of G and C nucleotides as disclosed in WO2002098443 A2. As a second step the G/C-enrichment or maximization is followed by a step of further C-optimization.

A vector for in vitro transcription was constructed containing a T7 promoter followed by a sequence coding for *Photinus pyralis* luciferase (PpLuc(wt), obtained from Promega) and a poly(A) sequence of 70 adenosine nucleotides (A70 poly(A) sequence). mRNA obtained from this vector by in vitro transcription is designated as "PpLuc(wt)-A70" (R873). In FIG. 1 (SEQ ID NO: 1) the sequence of the corresponding wild type luciferase mRNA is shown.

The vector was modified by replacing the wild type coding sequence of the mRNA by a GC-enriched (R875, FIG. 2, SEQ ID NO:2) or C-enriched (R2103, FIG. 3, SEQ ID NO:3) coding sequence, respectively, for stabilization. mRNA was obtained from these vectors by in vitro transcription.

A further vector for in vitro transcription was constructed containing a T7 promoter followed by a GC-enriched sequence coding for *Photinus pyralis* luciferase (PpLuc(GC) III) and an A64 poly(A) sequence. The vector was modified by replacing the GC-optimized coding sequence by a C-enriched sequence.

mRNA obtained from these vectors by in vitro transcription is designated as "PpLuc(GC)III-A64" (R2349) or PpLuc(GC)V-A64 (R2350), respectively.

In SEQ ID NO: 4 (FIG. 4) and SEQ ID NO: 5 (FIG. 5) the sequences of the corresponding mRNAs are shown.

Two further vectors were prepared by introducing a 5'-TOP-UTR derived from the ribosomal protein 32L, modifying the wild type coding sequence by introducing a GC-optimized or C-optimized sequence for stabilization, followed by a stabilizing sequence derived from the albumin-3'-UTR, a stretch of 64 adenosines (poly(A)-sequence), a stretch of 30 cytosines (poly(C)-sequence), and a histone stem loop. mRNA obtained from these vectors by in vitro transcription is designated as R2791 or R2793, respectively.

In SEQ ID NO: 6 (FIG. 6) and SEQ ID NO: 7 (FIG. 7) the sequences of the corresponding mRNAs are shown.

TABLE 1

Luciferase mRNA constructs

| R number | SEQ ID NO. | Construct | Base | Composition of complete RNA Number | % |
|---|---|---|---|---|---|
| R873 | SEQ ID NO. 1 | ppLuc(wt) ... A70 | A | 534 | 30.4 |
| | | | C | 371 | 21.1 |
| | | | G | 418 | 23.8 |
| | | | T | 435 | 24.7 |
| R875 | SEQ ID NO. 2 | ppLuc(GC)II ... A70 | A | 405 | 23.0 |
| | | | C | 579 | 32.9 |
| | | | G | 517 | 29.4 |
| | | | T | 257 | 14.6 |

TABLE 1-continued

Luciferase mRNA constructs

| R number | SEQ ID NO. | Construct | Composition of complete RNA | | |
|---|---|---|---|---|---|
| | | | Base | Number | % |
| R2103 | SEQ ID NO. 3 | ppLuc(GC)V . . . A70 | A | 390 | 22.2 |
| | | | C | 710 | 40.4 |
| | | | G | 386 | 22.0 |
| | | | T | 272 | 15.5 |
| R2349 | SEQ ID NO. 4 | PpLuc(GC)III . . . A64 | A | 397 | 22.7 |
| | | | C | 600 | 34.4 |
| | | | G | 492 | 28.2 |
| | | | T | 257 | 14.7 |
| R2350 | SEQ ID NO. 5 | PpLuc(GC)V . . . A64 | A | 382 | 21.9 |
| | | | C | 709 | 40.6 |
| | | | G | 385 | 22.1 |
| | | | T | 270 | 15.5 |
| R2791 | SEQ ID NO. 6 | 32L4 . . . PpLuc(GC)II . . . albumin7 . . . A64 . . . C30-histoneSL-N5 | A | 476 | 23.4 |
| | | | C | 668 | 32.8 |
| | | | G | 556 | 27.3 |
| | | | T | 335 | 16.5 |
| R2793 | SEQ ID NO. 7 | 32L4 . . . PpLuc(GC)V . . . albumin7 . . . A64 . . . C30-histoneSL-N5 | A | 461 | 22.7 |
| | | | C | 799 | 39.3 |
| | | | G | 425 | 20.9 |
| | | | T | 350 | 17.2 |

2. In Vitro Transcription

The respective DNA plasmids prepared according to paragraph 1 were transcribed in vitro using T7 polymerase in the presence of a CAP analog (m$^7$GpppG). Subsequently the mRNA was purified using PureMessenger® (CureVac, Tubingen, Germany; WO2008/077592A1).

3. Reagents

Complexation Reagent: Protamine

4. Formulation of mRNA

The mRNA was complexed with protamine by addition of protamine to the mRNA in the ratio RNA/protamine of 2:1 (w/w).

Example 2: Immunostimulation of Peripheral Blood Mononuclear Cells (PBMCs) Treated with Modified mRNAs Preparation of Human PBMCs 25 ml of a buffy coat were layered over 20 ml of Ficoll in a 50 ml Falcon tube. After centrifugation at 805 relative centrifugal force (rcf) for 20 minutes, cells at the interphase were collected. Cells were washed two times by resuspending in PBS and centrifuging. After counting, cells were resuspended at 50 million cells per ml in fetal calf serum, 10% DMSO, and frozen.

PBMC Stimulation

Human PBMCs were seeded at a density of 10$^6$ cells/ml into each well of a 96-well plate (2×10$^5$ cells/well) in X-Vivo 15 medium (Lonza) and treated with 10 µg/ml of GC- or C-enriched mRNA for 20 hours and the TNFα concentration was determined in the supernatant by ELISA.

Cytokine ELISA (TNFα)

96 well ELISA plates were coated with capture antibody (BD Pharmingen) in coating buffer (15 mM Na$_2$CO$_3$, 15 mM NaHCO$_3$, 0.02% NaN$_3$, pH 9.6) over night at room temperature. Plates were blocked with blocking buffer (PBS, 0.05% Tween-20, 1% BSA, pH7.4) for 1 hour at room temperature. Plates were washed three times (PBS, 0.05% Tween-20, pH7.4). 50 µl of supernatants of stimulated PBMC, diluted with 50 µl of blocking buffer, were added to the plates and incubated for 2 hours at room temperature. Plates were washed three times. Biotinylated detection antibody diluted in blocking buffer was added to the plates and incubated for 1 hour at room temperature. Plates were washed three times. HRP-Streptavidin diluted in blocking buffer without NaN$_3$ was added to the plates and incubated for 30 minutes at room temperature. Plates were washed three times. 100 µl/well of TMB substrate (Perbioscience) was added to the plates. To stop color development, 100 µl of 20% H$_2$SO$_4$ was added to the plates. Absorbance at 450 nm was measured.

Transfection of HeLa Cells and Determination of Luciferase Activity

HeLa cells were trypsinized and washed in opti-MEM medium (Life Technologies). Cells were electroporated with PpLuc-encoding mRNA in 200 µl volume. Electroporated cells were seeded in 24-well plates in 1 ml of RPMI 1640 medium (between 0.3 to 0.5 µg of PpLuc mRNA and 100000 cells per well). 6, 24, or 48 hours after transfection, medium was aspirated and cells were lysed. Lysates were stored at −80° C. Luciferase activity was measured as relative light units (RLU) in a BioTek SynergyHT plate reader. PpLuc activity was measured at 5 seconds measuring time using 50 µl of lysate and 200 µl of luciferin buffer (75 µM luciferin, 25 mM Glycylglycin, pH 7.8 (NaOH), 15 mM MgSO$_4$, 2 mM ATP).

Results

Figure 8:
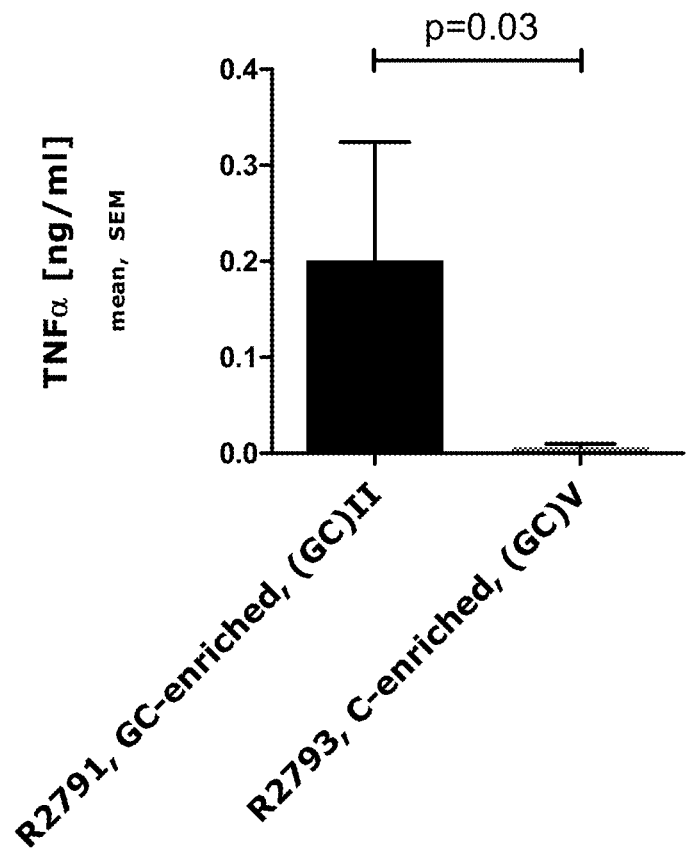
FIG. 8: TNFα secretion of PBMCs treated with R2793 and R2791 mRNAs.

FIG. 8 shows that the treatment of human PBMCs with C-enriched mRNA (R2793) results in significantly less TNFα secretion compared to treatment with GC-enriched mRNA (R2791).

FIG. 9A shows that the activity of luciferase encoded by GC-enriched mRNA (R875) and C-enriched mRNA (R2103) was comparable both in terms of peak level and kinetics.

FIG. 9B shows that the activity of luciferase encoded by GC-enriched mRNA (R875) was much higher than that of the wildtype construct (R873).

Example 3: Dose-Response Relationship for Immunostimulation of PBMCs Treated with Modified mRNAs PBMC Stimulation Human PBMCs were prepared as described in Example 2. PBMCs were seeded at a density of 10$^6$ cells/ml into each well of a 96-well plate (2×10$^5$ cells/well) in X-Vivo 15 medium (Lonza) and treated with 40 or 20 µg/ml of GC- or C-enriched mRNAs as indicated for 20 hours. The TNFα and IFNα concentrations were determined in the supernatant by ELISA.

Cytokine ELISA

The TNFα ELISA was performed as described in Example 2. The IFNα ELISA was performed analogously, replacing the capture and detection antibodies appropriately (Mabtech).

Results

FIG. 10 shows the dose-response relationship for TNFα secretion of human PBMCs treated with various modified mRNAs. As can be seen the treatment with C-enriched mRNA results in less TNFα secretion than with GC-enriched mRNA.

FIG. 11 shows the dose-response relationship for IFN☐ secretion of human PBMCs treated with various modified mRNAs. As can be seen the treatment with C-enriched mRNA results in less TNF☐ secretion than with GC-enriched mRNA.

TABLE 2

Summary of the nucleotide composition and codon usage of the constructs used in the present Examples

| AA | human Codon-usage | | | | GC-reicher Code | | ppLuc(GC) G: 542 A: 333 T: 240 C: 538 Seltene Codons: 41 CAI: 0.185 | | | ppLuc (wt) G: 410 A: 454 T: 426 C: 363 Seltene Codons: 45 CAI: 0.222 | | | ppLuc(GC)II G: 507 A: 324 T: 249 C: 573 Seltene Codons: 24 CAI: 0.193 | | | ppLuc(GC)III G: 483 A: 324 T: 251 C: 595 Seltene Codons: 0 CAI: 0.190 | | | ppLuc(GC)V G: 376 A: 309 T: 264 C: 704 Seltene Codons: 0 CAI: 0.385 | | |
|---|---|---|---|---|---|---|---|---|---|---|---|---|---|---|---|---|---|---|---|---|---|
| | cod | frac | /1000 | AA | cod | frac | cod | number | frac | cod | number | frac | cod | number | frac | cod | number | frac | cod | num | frac |
| Ala | GCG | 0.10 | 7.4 | Ala | GCG | 0.20 | GCG | 7.00 | 0.16 | GCG | 11 | 2.0 | GCG | 9.00 | 0.21 | GCG | 0.00 | 0.00 | GCG | 0 | 0.00 |
| Ala | GCA | 0.22 | 15.8 | Ala | GCA | 0.00 | GCA | 0.00 | 0.00 | GCA | 7 | 1.3 | GCA | 0.00 | 0.00 | GCA | 0.00 | 0.00 | GCA | 0 | 0.00 |
| Ala | GCT | 0.28 | 18.5 | Ala | GCT | 0.00 | GCT | 0.00 | 0.00 | GCT | 12 | 2.2 | GCT | 0.00 | 0.00 | GCT | 0.00 | 0.00 | GCT | 0 | 0.00 |
| Ala | GCC | 0.40 | 27.7 | Ala | GCC | 0.80 | GCC | 36.00 | 0.84 | GCC | 13 | 2.4 | GCC | 34.00 | 0.79 | GCC | 43.00 | 1.00 | GCC | 43 | 1.00 |
| Cys | TGT | 0.42 | 10.6 | Cys | TGT | 0.00 | TGT | 0.00 | 0.00 | TGT | 2 | 0.4 | TGT | 0.00 | 0.00 | TGT | 0.00 | 0.00 | TGT | 0 | 0.00 |
| Cys | TGC | 0.58 | 12.6 | Cys | TGC | 1.00 | TGC | 4.00 | 1.00 | TGC | 2 | 0.4 | TGC | 4.00 | 1.00 | TGC | 4.00 | 1.00 | TGC | 4 | 1.00 |
| Asp | GAT | 0.44 | 21.8 | Asp | GAT | 0.00 | GAT | 0.00 | 0.00 | GAT | 17 | 3.1 | GAT | 0.00 | 0.00 | GAT | 0.00 | 0.00 | GAT | 0 | 0.00 |
| Asp | GAC | 0.56 | 25.1 | Asp | GAC | 1.00 | GAC | 32.00 | 1.00 | GAC | 15 | 2.7 | GAC | 32.00 | 1.00 | GAC | 32.00 | 1.00 | GAC | 32 | 1.00 |
| Glu | GAG | 0.59 | 39.6 | Glu | GAG | 1.00 | GAG | 33.00 | 1.00 | GAG | 10 | 1.8 | GAG | 33.00 | 1.00 | GAG | 33.00 | 1.00 | GAG | 33 | 1.00 |
| Glu | GAA | 0.41 | 29.0 | Glu | GAA | 0.00 | GAA | 0.00 | 0.00 | GAA | 23 | 4.2 | GAA | 0.00 | 0.00 | GAA | 0.00 | 0.00 | GAA | 0 | 0.00 |
| Phe | TTT | 0.43 | 17.6 | Phe | TTT | 0.00 | TTT | 0.00 | 0.00 | TTT | 15 | 2.7 | TTT | 0.00 | 0.00 | TTT | 0.00 | 0.00 | TTT | 0 | 0.00 |
| Phe | TTC | 0.57 | 20.3 | Phe | TTC | 1.00 | TTC | 30.00 | 1.00 | TTC | 15 | 2.7 | TTC | 30.00 | 1.00 | TTC | 30.00 | 1.00 | TTC | 30 | 1.00 |
| Gly | GGG | 0.23 | 16.5 | Gly | GGG | 0.41 | GGG | 8.00 | 0.17 | GGG | 6 | 1.1 | GGG | 19.00 | 0.41 | GGG | 19.00 | 0.41 | GGG | 0 | 0.00 |
| Gly | GGA | 0.26 | 16.5 | Gly | GGA | 0.00 | GGA | 0.00 | 0.00 | GGA | 17 | 3.1 | GGA | 0.00 | 0.00 | GGA | 0.00 | 0.00 | GGA | 0 | 0.00 |
| Gly | GGT | 0.18 | 10.8 | Gly | GGT | 0.00 | GGT | 0.00 | 0.00 | GGT | 13 | 2.4 | GGT | 0.00 | 0.00 | GGT | 0.00 | 0.00 | GGT | 0 | 0.00 |
| Gly | GGC | 0.33 | 22.2 | Gly | GGC | 0.59 | GGC | 38.00 | 0.83 | GGC | 10 | 1.8 | GGC | 27.00 | 0.59 | GGC | 27.00 | 0.59 | GGC | 46 | 1.00 |
| His | CAT | 0.41 | 10.9 | His | CAT | 0.00 | CAT | 0.00 | 0.00 | CAT | 8 | 1.5 | CAT | 0.00 | 0.00 | CAT | 0.00 | 0.00 | CAT | 0 | 0.00 |
| His | CAC | 0.59 | 15.1 | His | CAC | 1.00 | CAC | 14.00 | 1.00 | CAC | 6 | 1.1 | CAC | 14.00 | 1.00 | CAC | 14.00 | 1.00 | CAC | 14 | 1.00 |
| Ile | ATA | 0.14 | 7.5 | Ile | ATA | 0.00 | ATA | 0.00 | 0.00 | ATA | 4 | 0.7 | ATA | 0.00 | 0.00 | ATA | 0.00 | 0.00 | ATA | 0 | 0.00 |
| Ile | ATT | 0.35 | 16.0 | Ile | ATT | 0.00 | ATT | 0.00 | 0.00 | ATT | 18 | 3.3 | ATT | 0.00 | 0.00 | ATT | 0.00 | 0.00 | ATT | 0 | 0.00 |
| Ile | ATC | 0.52 | 20.8 | Ile | ATC | 1.00 | ATC | 39.00 | 1.00 | ATC | 17 | 3.1 | ATC | 39.00 | 1.00 | ATC | 39.00 | 1.00 | ATC | 39 | 1.00 |
| Lys | AAG | 0.60 | 31.9 | Lys | AAG | 1.00 | AAG | 39.00 | 1.00 | AAG | 19 | 3.5 | AAG | 39.00 | 1.00 | AAG | 39.00 | 1.00 | AAG | 39 | 1.00 |
| Lys | AAA | 0.40 | 24.4 | Lys | AAA | 0.00 | AAA | 0.00 | 0.00 | AAA | 20 | 3.6 | AAA | 0.00 | 0.00 | AAA | 0.00 | 0.00 | AAA | 0 | 0.00 |
| Leu | TTG | 0.12 | 12.9 | Leu | TTG | 0.00 | TTG | 0.00 | 0.00 | TTG | 11 | 2.0 | TTG | 0.00 | 0.00 | TTG | 0.00 | 0.00 | TTG | 0 | 0.00 |
| Leu | TTA | 0.06 | 7.7 | Leu | TTA | 0.00 | TTA | 0.00 | 0.00 | TTA | 5 | 0.9 | TTA | 0.00 | 0.00 | TTA | 0.00 | 0.00 | TTA | 0 | 0.00 |
| Leu | CTG | 0.43 | 39.6 | Leu | CTG | 0.68 | CTG | 42.00 | 0.82 | CTG | 19 | 3.5 | CTG | 34.00 | 0.67 | CTG | 34.00 | 0.67 | CTG | 51 | 1.00 |
| Leu | CTA | 0.07 | 7.2 | Leu | CTA | 0.00 | CTA | 0.00 | 0.00 | CTA | 3 | 0.5 | CTA | 0.00 | 0.00 | CTA | 0.00 | 0.00 | CTA | 0 | 0.00 |
| Leu | CTT | 0.12 | 13.2 | Leu | CTT | 0.00 | CTT | 0.00 | 0.00 | CTT | 5 | 0.9 | CTT | 0.00 | 0.00 | CTT | 0.00 | 0.00 | CTT | 0 | 0.00 |
| Leu | CTC | 0.20 | 19.6 | Leu | CTC | 0.32 | CTC | 9.00 | 0.18 | CTC | 8 | 1.5 | CTC | 17.00 | 0.33 | CTC | 17.00 | 0.33 | CTC | 0 | 0.00 |
| Met | ATG | 1.00 | 22.0 | Met | ATG | 1.00 | ATG | 14.00 | 1.00 | ATG | 14 | 2.5 | ATG | 14.00 | 1.00 | ATG | 14.00 | 1.00 | ATG | 14 | 1.00 |
| Asn | AAT | 0.44 | 17.0 | Asn | AAT | 0.00 | AAT | 0.00 | 0.00 | AAT | 8 | 1.5 | AAT | 0.00 | 0.00 | AAT | 0.00 | 0.00 | AAT | 0 | 0.00 |
| Asn | AAC | 0.56 | 19.1 | Asn | AAC | 1.00 | AAC | 17.00 | 1.00 | AAC | 9 | 1.6 | AAC | 17.00 | 1.00 | AAC | 17.00 | 1.00 | AAC | 17 | 1.00 |
| Pro | CCG | 0.11 | 6.9 | Pro | CCG | 0.25 | CCG | 24.00 | 0.83 | CCG | 7 | 1.3 | CCG | 8.00 | 0.28 | CCG | 0.00 | 0.00 | CCG | 0 | 0.00 |
| Pro | CCA | 0.27 | 16.9 | Pro | CCA | 0.00 | CCA | 0.00 | 0.00 | CCA | 7 | 1.3 | CCA | 0.00 | 0.00 | CCA | 0.00 | 0.00 | CCA | 0 | 0.00 |
| Pro | CCT | 0.29 | 17.5 | Pro | CCT | 0.00 | CCT | 0.00 | 0.00 | CCT | 7 | 1.3 | CCT | 0.00 | 0.00 | *CCT* | *2.00* | *0.07* | CCT | 0 | 0.00 |
| Pro | CCC | 0.33 | 19.8 | Pro | CCC | 0.75 | CCC | 5.00 | 0.17 | CCC | 8 | 1.5 | CCC | 21.00 | 0.72 | CCC | 27.00 | 0.93 | CCC | 29 | 1.00 |
| Gln | CAG | 0.73 | 34.2 | Gln | CAG | 1.00 | CAG | 16.00 | 1.00 | CAG | 5 | 0.9 | CAG | 16.00 | 1.00 | CAG | 16.00 | 1.00 | CAG | 16 | 1.00 |
| Gln | CAA | 0.27 | 12.3 | Gln | CAA | 0.00 | CAA | 0.00 | 0.00 | CAA | 11 | 2.0 | CAA | 0.00 | 0.00 | CAA | 0.00 | 0.00 | CAA | 0 | 0.00 |

TABLE 2-continued

Summary of the nucleotide composition and codon usage of the constructs used in the present Examples

| AA | human Codon-usage | | | GC-reicher Code | | PpLuc(GC) G: 542 A: 333 T: 240 C: 538 Seltene Codons: 41 CAI: 0.185 | | | PpLuc (wt) G: 410 A: 454 T: 426 C: 363 Seltene Codons: 45 CAI: 0.222 | | | ppLuc(GC)II G: 507 A: 324 T: 249 C: 573 Seltene Codons: 24 CAI: 0.193 | | | ppLuc(GC)III G: 483 A: 324 T: 251 C: 595 Seltene Codons: 0 CAI: 0.190 | | | ppLuc(GC)V G: 376 A: 309 T: 264 C: 704 Seltene Codons: 0 CAI: 0.385 | | |
|---|---|---|---|---|---|---|---|---|---|---|---|---|---|---|---|---|---|---|---|---|
| | cod | frac | /1000 | AA | cod | frac | cod | number | frac | cod | number | frac | cod | number | frac | cod | number | frac | cod | num | frac |
| Arg | AGG | 0.22 | 12.0 | Arg | AGG | 0.00 | AGG | 0.00 | 0.00 | AGG | 4 | 0.7 | AGG | 0.00 | 0.00 | AGG | 0.00 | 0.00 | AGG | 0 | 0.00 |
| Arg | AGA | 0.21 | 12.1 | Arg | AGA | 0.00 | AGA | 0.00 | 0.00 | AGA | 10 | 1.8 | AGA | 0.00 | 0.00 | AGA | 0.00 | 0.00 | AGA | 0 | 0.00 |
| Arg | CGG | 0.19 | 11.4 | Arg | CGG | 0.50 | CGG | 16.00 | 0.80 | CGG | 1 | 0.2 | CGG | 10.00 | 0.50 | CGG | 10.00 | 0.50 | CGG | 0 | 0.00 |
| Arg | CGA | 0.10 | 6.2 | Arg | CGA | 0.00 | CGA | 0.00 | 0.00 | CGA | 2 | 0.4 | CGA | 0.00 | 0.00 | CGA | 0.00 | 0.00 | CGA | 0 | 0.00 |
| Arg | CGT | 0.09 | 4.5 | Arg | CGT | 0.00 | CGT | 0.00 | 0.00 | CGT | 1 | 0.2 | CGT | 0.00 | 0.00 | CGT | 0.00 | 0.00 | CGT | 0 | 0.00 |
| Arg | CGC | 0.19 | 10.4 | Arg | CGC | 0.50 | CGC | 4.00 | 0.20 | CGC | 2 | 0.4 | CGC | 10.00 | 0.50 | CGC | 10.00 | 0.50 | CGC | 20 | 1.00 |
| Ser | AGT | 0.14 | 12.1 | Ser | AGT | 0.00 | AGT | 0.00 | 0.00 | AGT | 5 | 0.9 | AGT | 0.00 | 0.00 | AGT | 0.00 | 0.00 | AGT | 0 | 0.00 |
| Ser | AGC | 0.25 | 19.5 | Ser | AGC | 0.52 | AGC | 23.00 | 0.82 | AGC | 2 | 0.4 | AGC | 15.00 | 0.54 | AGC | 15.00 | 0.54 | AGC | 0 | 0.00 |
| Ser | TCG | 0.06 | 4.4 | Ser | TCG | 0.00 | TCG | 5.00 | 0.18 | TCG | 3 | 0.5 | TCG | 0.00 | 0.00 | TCG | 0.00 | 0.00 | TCG | 0 | 0.00 |
| Ser | TCA | 0.15 | 12.2 | Ser | TCA | 0.00 | TCA | 0.00 | 0.00 | TCA | 1 | 0.2 | TCA | 0.00 | 0.00 | TCA | 0.00 | 0.00 | TCA | 0 | 0.00 |
| Ser | TCT | 0.18 | 15.2 | Ser | TCT | 0.00 | TCT | 0.00 | 0.00 | TCT | 10 | 1.8 | TCT | 0.00 | 0.00 | TCT | 0.00 | 0.00 | TCT | 0 | 0.00 |
| Ser | TCC | 0.23 | 17.7 | Ser | TCC | 0.48 | TCC | 0.00 | 0.00 | TCC | 7 | 1.3 | TCC | 13.00 | 0.46 | TCC | 13.00 | 0.46 | TCC | 28 | 1.00 |
| Thr | ACG | 0.12 | 6.1 | Thr | ACG | 0.24 | ACG | 5.00 | 0.17 | ACG | 5 | 0.9 | ACG | 7.00 | 0.24 | ACG | 0.00 | 0.00 | ACG | 0 | 0.00 |
| Thr | ACA | 0.27 | 15.1 | Thr | ACA | 0.00 | ACA | 0.00 | 0.00 | ACA | 9 | 1.6 | ACA | 0.00 | 0.00 | ACA | 0.00 | 0.00 | ACA | 0 | 0.00 |
| Thr | ACT | 0.23 | 13.1 | Thr | ACT | 0.00 | ACT | 0.00 | 0.00 | ACT | 8 | 1.5 | ACT | 0.00 | 0.00 | ACT | 0.00 | 0.00 | ACT | 0 | 0.00 |
| Thr | ACC | 0.38 | 18.9 | Thr | ACC | 0.76 | ACC | 24.00 | 0.83 | ACC | 7 | 1.3 | ACC | 22.00 | 0.76 | ACC | 29.00 | 1.00 | ACC | 29 | 1.00 |
| Val | GTG | 0.48 | 28.1 | Val | GTG | 0.66 | GTG | 37.00 | 0.82 | GTG | 15 | 2.7 | GTG | 29.00 | 0.64 | GTG | 29.00 | 0.64 | GTG | 0 | 0.00 |
| Val | GTA | 0.11 | 7.1 | Val | GTA | 0.00 | GTA | 0.00 | 0.00 | GTA | 4 | 0.7 | GTA | 0.00 | 0.00 | GTA | 0.00 | 0.00 | GTA | 0 | 0.00 |
| Val | GTT | 0.17 | 11.0 | Val | GTT | 0.00 | GTT | 0.00 | 0.00 | GTT | 17 | 3.1 | GTT | 0.00 | 0.00 | GTT | 0.00 | 0.00 | GTT | 0 | 0.00 |
| Val | GTC | 0.25 | 14.5 | Val | GTC | 0.34 | GTC | 8.00 | 0.18 | GTC | 9 | 1.6 | GTC | 16.00 | 0.36 | GTC | 16.00 | 0.36 | GTC | 45 | 1.00 |
| Trp | TGG | 1.00 | 13.2 | Trp | TGG | 1.00 | TGG | 2.00 | 1.00 | TGG | 2 | 0.4 | TGG | 2.00 | 1.00 | TGG | 2.00 | 1.00 | TGG | 2 | 1.00 |
| Tyr | TAT | 0.42 | 12.2 | Tyr | TAT | 0.00 | TAT | 0.00 | 0.00 | TAT | 11 | 2.0 | *TAT* | *1.00* | *0.05* | *TAT* | *1.00* | *0.05* | *TAT* | *1* | *0.05* |
| Tyr | TAC | 0.58 | 15.3 | Tyr | TAC | 1.00 | TAC | 19.00 | 1.00 | TAC | 8 | 1.5 | TAC | 18.00 | 0.95 | TAC | 18.00 | 0.95 | TAC | 18 | 0.95 |
| Stop | TGA | 0.61 | 1.6 | End | TGA | 0.78 | TGA | 0.00 | 0.00 | TAA | 1 | | TGA | 1.00 | 1.00 | TGA | 1.00 | 1.00 | TGA | 1 | 1.00 |
| Stop | TAG | 0.17 | 0.8 | End | TAG | 0.22 | TAG | 0.00 | 0.00 | | | | TAG | 0.00 | 0.00 | TAG | 0.00 | 0.00 | TAG | 0 | 0.00 |
| Stop | TAA | 0.22 | 1.0 | End | TAA | 0.00 | TAA | 1.00 | 1.00 | | | | TAA | 0.00 | 0.00 | TAA | 0.00 | 0.00 | TAA | 0 | 0.00 |

The invention claimed is:

1. A method for synthesis of a modified mRNA that provides decreased immunogenicity or immune stimulating activity comprising the steps of:
   (a) identifying a target mRNA wild type sequence coding for a biologically active polypeptide or protein;
   (b) modifying at least 70% of the codons of the wild type sequence which are cytosine-content optimizable by replacing at least 70% of said cytosine-content optimizable codons of the wild type sequence with a codon coding for the same amino add but having a higher cytosine-content than the cytosine-content optimizable codon being replaced, thereby increasing the cytosine-content of the mRNA such that the cytosine-content of the coding region of the modified mRNA is greater than the cytosine-content of the coding region of the wild type sequence, whereby the amino add sequence encoded by the modified mRNA is unchanged compared to the wild type sequence, and wherein the codons replacing the cytosine-content optimizable codons do not have a higher G-content than the wild type sequence; and
   (c) synthesizing the modified mRNA.

2. The method according to claim 1, wherein the cytosine-content of the coding region of the modified mRNA is at least 10% greater than the cytosine-content of the coding region of the wild type sequence.

3. The method according to claim 2, wherein the cytosine-content of the coding region of the modified mRNA is at least 12.5% greater than the cytosine-content of the coding region of the wild type mRNA.

4. The method according to claim 3, wherein the cytosine-content of the coding region of the modified mRNA is at least 15% greater than the cytosine-content of the coding region of the wild type mRNA.

5. The method according to claim 1, wherein all codons of the wild type sequence that are not cytosine-content optimizable and that code for a rare tRNA codons in the cell are replaced by codons that code for a more frequent tRNA in the cell, which carries the same amino acid as the rare tRNA.

6. The method according to claim 1, wherein the codon adaptation index (CAI) of the coding region of the modified mRNA is at least 0.05 greater than the CAI of the coding region of the wild type mRNA coding for the polypeptide or protein.

7. The method according to claim 6, wherein the codon adaptation index (CAI) of the coding region of the modified mRNA is at least 0.1 greater than the CAI of the coding region of the wild type mRNA coding for the polypeptide or protein.

8. The method according to claim 7, wherein the codon adaptation index (CAI) of the coding region of the modified mRNA is at least 0.15 greater than the CAI of the coding region of the wild type mRNA coding for the polypeptide or protein.

9. The method according to claim 1, wherein the method further comprises the step of determining the immunogenicity and/or immunostimulatory capacity of the modified mRNA.

10. The method according to claim 9, wherein determining the immunogenicity and/or immunostimulatory capacity of the modified mRNA comprises the sub-steps of:
    (i) transfecting peripheral blood mononuclear cells (PBMCs) with the modified mRNA,
    (ii) cultivating the cells for at least 8 hours,
    (iii) measuring the amount of pro-inflammatory cytokines in a cell supernatant from step (ii).

11. The method according to claim 10, wherein the modified mRNA coding for the polypeptide or protein that has lower immunogenicity and/or immunostimulatory capacity than the wild type mRNA is selected and steps (a), (b) and (c) are repeated to further decrease the immunogenicity and/or immunostimulatory capacity of the modified mRNA.

12. The method according to claim 10, wherein the cultivating of step (ii) lasts for at least 12 hours.

13. The method according to claim 12, wherein the cultivating of step (ii) lasts for at least 20 hours.

14. The method according to claim 1, wherein the method is carried out by executing at least one algorithm on a computer with the aid of software.

15. The method according to claim 1, wherein the modified mRNA is obtained by in vitro transcription.

16. The method according to claim 15, wherein the in vitro transcription is bacteriophage polymerase-mediated in vitro transcription, Sp6 polymerase in vitro transcription, T3 polymerase-mediated in vitro transcription, or T7 polymerase-mediated in vitro transcription.

17. The method according to claim 1, wherein step (b) further comprises modifying at least 70% of codons for amino acids not eligible for cytosine-content optimization, but eligible for guanosine-content optimization, thereby increasing the guanosine-content of the modified mRNA.

* * * * *

UNITED STATES PATENT AND TRADEMARK OFFICE
CERTIFICATE OF CORRECTION

PATENT NO. : 10,898,584 B2
APPLICATION NO. : 15/142082
DATED : January 26, 2021
INVENTOR(S) : Thomas Schlake et al.

Page 1 of 1

It is certified that error appears in the above-identified patent and that said Letters Patent is hereby corrected as shown below:

In the Claims

In Claim 1, Column 59, Line 34, delete "add" and insert --acid-- therefor.

In Claim 1, Column 59, Line 40, delete "add" and insert --acid-- therefor.

Signed and Sealed this
Eleventh Day of May, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 12

<210> SEQ ID NO 1
<211> LENGTH: 1758
<212> TYPE: RNA
<213> ORGANISM: Artificial Sequence
<220> FEATURE:
<223> OTHER INFORMATION: Photinus pyralis luciferase

<400> SEQUENCE: 1

| | | | | | |
|---|---|---|---|---|---|
| gggagaugua | caaagcuuac | cauggaagac | gccaaaaaca | uaagaaagg | cccggcgcca | 60 |
| uucuauccgc | uggaagaugg | aaccgcugga | gagcaacugc | auaaggcuau | gaagagauac | 120 |
| gcccugguuc | cuggaacaau | ugcuuuuaca | gaugcacaua | ucgagugga | caucacuuac | 180 |
| gcugaguacu | ucgaaauguc | cguucgguug | gcagaagcua | ugaaacgaua | ugggcugaau | 240 |
| acaaaucaca | gaaucgucgu | augcagugaa | aacucucuuc | aauucuuuau | gccggguguug | 300 |
| ggcgcguuau | uuaucggagu | ugcaguugcg | cccgcgaacg | acauuauaa | ugaacgugaa | 360 |
| uugcucaaca | guaugggcau | ucgcagccu | accguggugu | ucguuuccaa | aaggggguug | 420 |
| caaaaauuu | ugaacgugca | aaaaaagcuc | ccaaucaucc | aaaaaauuau | uaucauggau | 480 |
| ucuaaaacgg | auuaccaggg | auuucagucg | auguacacgu | ucgucacauc | ucaucuaccu | 540 |
| cccguuuua | augaauacga | uuuugugcca | gaguccuucg | auaggacaa | gacaauugca | 600 |
| cugaucauga | acuccucugg | aucuacuggu | cugccuaaag | gugucgcucu | gccucauaga | 660 |
| acugccugcg | ugagauucu | gcaugccaga | gauccuauu | uuggcaauca | aaucauuccg | 720 |
| gauacugcga | uuuuaagugu | uguuccauuc | caucacgguu | uggaauguu | uacuacacuc | 780 |
| ggauauuga | uauguggauu | ucgagucguc | uuaauguaua | gauuugaaga | gagcuguuu | 840 |
| cugaggagcc | uucaggauua | caagauucaa | agugcgcugc | uggugccaac | ccuauucucc | 900 |
| uucuucgcca | aaagcacucu | gauugacaaa | uacgauuuau | cuaauuuaca | cgaaauugcu | 960 |
| ucuggguggcg | cuccccucuc | uaaggaaguc | ggggaagcgg | uugccaagag | guuccaucug | 1020 |
| ccagguauca | ggcaaggaua | ugggcucacu | gagacuacau | cagcuauucu | gauuacaccc | 1080 |
| gaggggaug | auaaaccggg | cgcggucggu | aaaguuguuc | cauuuuuga | agcgaagguu | 1140 |
| guggaucugg | auaccgggaa | aacgcugggc | guuaaucaaa | gaggcgaacu | guguguugaga | 1200 |
| gguccuauga | uuauguccgg | uuauguaaac | aauccggaag | cgaccaacgc | cuugauugac | 1260 |
| aaggauggau | ggcuacauuc | uggagacaua | gcuuacuggg | acgaagacga | acacuucuuc | 1320 |
| aucguugacc | gccugaaguc | ucugauuaag | uacaaaggcu | aucagguggc | ucccgcugaa | 1380 |
| uuggaaucca | ucuugcucca | acaccccaac | aucuucgacg | cagguguccgc | aggucucccc | 1440 |
| gacgaugacg | ccggugaacu | ucccgccgcc | guugguguu | uggagcacgg | aaagacgaug | 1500 |
| acggaaaaag | agaucgugga | uuacgucgcc | agucaaguaa | caaccgcgaa | aaaguugcgc | 1560 |
| ggaggaguug | uguuugugga | cgaaguaccg | aaaggucuua | ccgaaaaacu | cgacgcaaga | 1620 |
| aaaaucagag | agauccucau | aaaggccaag | aagggcggaa | agaucgccgu | guaaccucua | 1680 |
| guagaucuaa | aaaaaaaaaa | aaaaaaaaaa | aaaaaaaaaa | aaaaaaaaaa | aaaaaaaaaa | 1740 |
| aaaaaaaaaa | aaaaaaaa | | | | | 1758 |

<210> SEQ ID NO 2
<211> LENGTH: 1758
<212> TYPE: RNA
<213> ORGANISM: Artificial Sequence
<220> FEATURE:
<223> OTHER INFORMATION: Photinus pyralis luciferase mRNA G/C-enriched

<400> SEQUENCE: 2

```
gggagaugua caaagcuuac cauggaggac gccaagaaca ucaagaaggg ccccgccccg      60
uucuaccccc uggaggacgg gaccgcgggc gagcagcucc acaaggccau gaagcgguac     120
gcccuggugc ccgggaccau cgccuucacg gacgcccaca ucgaggucga caucaccuac     180
gcggaguacu ucgagaugag cgugcgccug gccgaggcca ugaagcggua cggccucaac     240
accaaccacc gcaucguggu cugcuccgag aacagccugc aguucuucau gcccgugcug     300
ggggcccucu caucggcgu ggcggucgcc ccggccaacg acaucuacaa cgagcgggag      360
cugcugaacu ccaugggcau cagccagccc accgugugu cgucuccaa gaaggggcuc       420
cagaagaucc ugaacgugca gaagaagcug ccgaucaucc agaagaucau caucauggac     480
agcaagacgg acuaccaggg cuuccagucc auguauaccu ucgugaccag ccaccucccc     540
ccggggguuca cgaguacga cuucgucccc gaguccuucg accgcgacaa gaccaucgcc    600
cugaucauga acagcccgg cagcacgggg cugcccaagg gcguggcccu cccccaccgg      660
accgcgugcg ugcgcuucuc ccacgcccgg gacccgaucu cggcaaccac gaucauccc     720
gacaccgcca uccugagcgu cgugcccuuc caccacgggu ucggcauguu caccacgcug    780
ggguaccuca ucugcggcuu ccgcgugguc cugauguacc gguucgagga ggagcuguuc    840
cuccgcuccc ugcaggacua caagauccag agcgcccugc ucgugcccac ccuguucucc    900
uucuucgcca agagcacccu gaucgacaag uacgaccucu ccaaccugca cgagaucgcg    960
agcggcgggg ccccgcugag caaggaggug ggcgaggccg ucgccaagcg guuccaccuc   1020
cccgggaucc gccagggcua cgggcugacc gagacgaccu ccgccauccu gaucaccccc   1080
gagggcgacg acaagcccgg cgcggugggg aagguggucc cguucuucga ggccaaggug   1140
gucgaccucg acaccggcaa gacgcugggg gugaaccagc ggggcgagcu gugcgugcgc   1200
gggcccauga ucaugagcgg cuacgucaac aaccccgagg ccaccaacgc ccucaucgac   1260
aaggacggcu ggcugcacuc cgggacauc gccuacuggg acgaggacga gcacuucuuc    1320
aucguggacc ggcugaagag ccucaucaag uacaagggcu accagguggc gcccgccgag   1380
cuggagucca uccugcucca gcacccgaac aucuucgacg ccgggucgc cggccugccc    1440
gacgacgacg cggggggagcu gcccgccgcc guggugguccc ucgagcacgg caagaccaug   1500
accgagaagg agaucgugga cuacguggcc agccaggucc gaccgccaa gaagcugcgc     1560
ggcggggugg uguucgucga cgaggugccc aagggcccuga ccgggaagcu ggacgcgcgg   1620
aagauccgcg agauccucau caaggccaag aagggcggga agaucgccgu cgaggacua    1680
guagaucuaa aaaaaaaaa aaaaaaaaaa aaaaaaaaaa aaaaaaaaaa aaaaaaaaaa     1740
aaaaaaaaaa aaaaaaaa                                                  1758
```

<210> SEQ ID NO 3
<211> LENGTH: 1758
<212> TYPE: RNA
<213> ORGANISM: Artificial Sequence
<220> FEATURE:
<223> OTHER INFORMATION: Photinus pyralis luciferase mRNA C-enriched

<400> SEQUENCE: 3

```
gggagaugua caaagcuuac cauggaggac gccaagaaca ucaagaaggg ccccgccccc      60
uucuaccccc ucgaggacgg caccgccggc gagcagcucc acaaggccau gaagcgcuac     120
gcccucgucc ccggcaccau cgccuucacc gacgcccaca ucgaggucga caucaccuac     180
```

-continued

| | |
|---|---|
| gccgaguacu ucgagaugus cguccgccuc gccgaggcca ugaagcgcua cggccucaac | 240 |
| accaaccacc gcaucgucgu cugcuccgag aacuccuccc aguucuucau gcccguccuc | 300 |
| ggcgcccucu ucaucggcgu cgccgucgcc cccgccaacg acaucuacaa cgagcgcgag | 360 |
| cuccucaacu ccaugggcau ucccagccc accgucgucu cgucuccaa gaagggccuc | 420 |
| cagaagaucc ucaacgucca gaagaagcuc cccaucaucc agaagaucau caucauggac | 480 |
| uccaagaccg acuaccaggg cuuccagucc auguauaccu ugucaccucc caccuccc | 540 |
| cccggcuuca acgaguacga cuucgucccc gaguccuucg accgcgacaa gaccaucgcc | 600 |
| cucaucauga acuccuccgg cuccaccggc cuccccaagg gcgucgcccu cccccaccgc | 660 |
| accgccugcg uccgcuucuc ccacgcccgc gaccccaucu ucggcaacca gaucauccc | 720 |
| gacaccgcca uccucuccgu cgucccuuuc caccacggcu ucggcauguu caccaccccu | 780 |
| ggcuaccuca ucugcggcuu ccgcgucguc ucaguaucc gcuucgagga ggagcucuuc | 840 |
| cuccgcuccc uccaggacua caagauccag uccgcccucc ucguccccac ccucuucucc | 900 |
| uucuucgcca aguccacccu caucgacaag uacgaccucu ccaaccucca cgagaucgcc | 960 |
| uccggcggcg cccccccucuc caaggaggucu ggcgaggccg ucgccaagcg cuuccaccuc | 1020 |
| cccggcaucc gccagggcua cggcucacc gagaccaccu ccgccauccu caucaccccc | 1080 |
| gagggcgacg acaagcccgg cgccgucggc aaggucgucc cuucuucga ggccaagguc | 1140 |
| gucgaccucg acaccggcaa gacccucggc gucaaccagc gcggcgagcu cugcgucgc | 1200 |
| ggccccauga ucaugccggg cuacgucaac aaccccgagg ccaccaacgc ccucaucgac | 1260 |
| aaggacggcu ggcuccacuc cggcgacauc gccuacuggg acgaggacga gcacuucuuc | 1320 |
| aucgucgacc gccucaaguc ccucaucaag uacaagggcu accaggucgc ccccgccgag | 1380 |
| cucgagucca uccuccucca gcaccccaac aucuucgacg ccggcgucgc cggccucccc | 1440 |
| gacgacgacg ccggcgagcu ccccgccgcc gucgucgucc ucgagcacgg caagaccaug | 1500 |
| accgagaagg agaucgucga cuacgucgcc ucccagguca ccaccgccaa gaagcuccgc | 1560 |
| ggcggcgucg ucuucgucga cgagguccc aagggccuca ccggcaagcu cgacgcccgc | 1620 |
| aagauccgcg agauccucau caaggccaag aagggcggca agaucgccgu cugaggacua | 1680 |
| guagaucuaa aaaaaaaaaa aaaaaaaaaa aaaaaaaaaa aaaaaaaaaa aaaaaaaaaa | 1740 |
| aaaaaaaaaa aaaaaaaa | 1758 |

<210> SEQ ID NO 4
<211> LENGTH: 1746
<212> TYPE: RNA
<213> ORGANISM: Artificial Sequence
<220> FEATURE:
<223> OTHER INFORMATION: Photinus pyralis luciferase G/C-enriched

<400> SEQUENCE: 4

| | |
|---|---|
| gggagaaagc uuaccaugga ggacgccaag aacaucaaga agggcccgc ccccuucuac | 60 |
| cccccuggag acgggaccgc cggcgagcag cuccacaagg ccaugaagcg guacgcccug | 120 |
| gugcccggga ccaucgcccuu caccgacgcc cacaucgagg ucgacaucac cuacgccgag | 180 |
| uacuucgaga ugagcgugcg ccuggccgag gccaugaagc gguacggccu caacaccaac | 240 |
| caccgcaucg ugguucugcuc cgagaacagc cugcaguucu ucaugcccgu gcuggggcc | 300 |
| cucuucaucg gcguggccgu cgccccgccc aacgacaucu acaacgagcg ggagcugcug | 360 |
| aacuccaugg gcaucagcca gcccaccgug guguucgucu ccaagaaggg gccccagaag | 420 |
| auccugaacg ugcagaagaa gcugcccauc auccagaaga ucaucaucau ggacagcaag | 480 |

```
accgacuacc agggcuucca guccauguau accuucguga ccagccaccu cccucccggg    540
uucaacgagu acgacuucgu ccccgagucc uucgaccgcg acaagaccau cgcccugauc    600
augaacagcu ccggcagcac cgggcugccc aagggcgugg ccucccccca ccggaccgcc    660
ugcgugcgcu ucuccacgcc cgggaccccc aucuucggca accagaucau ccccgacacc    720
gccauccuga gcgucgugcc cuuccaccac ggguucggca guucaccacc cuggggguac    780
cucaucugcg gcuuccgcgu gguccugaug uaccgguucg aggaggagcu guuccuccgc    840
ucccugcagg acuacaagau ccagagcgcc cugcucgugc ccacccuguu uccuucuuc    900
gccaagagca cccugaucga caaguacgac cucuccaacc ugcacgagau cgccagcggc    960
ggggcccuc ugagcaagga ggugggcgag gccgucgcca agcgguucca ccuccccggg   1020
auccgccagg gcuacgggcu gaccgagacc accuccgcca uccugaucac ccccgagggc   1080
gacgacaagc ccggcgccgu ggggaaggug uccccuucu ucgaggccaa ggggucgac    1140
cucgacaccg gcaagacccu gggggugaac cagcggggcg agcugugcgu gcgcgggccc   1200
augaucauga gcggcuacgu caacaaccc gaggccacca acgcccucau cgacaaggac   1260
ggcuggcugc acuccgggga caucgccuac ugggacgagg acgagcacuu cuucaucgug   1320
gaccggcuga agagccucau caaguacaag ggcuaccagg uggcccccgc cgagcuggag   1380
uccauccugc ccagcacccc caacaucuuc gacgccgggg ucgccggccu gcccgacgac   1440
gacgccgggg agcugcccgc cgccguggug uccucgagc acggcaagac caugaccgag   1500
aaggagaucg uggacuacgu ggccagccag gucaccaccg ccaagaagcu gcgcggcggg   1560
guguguucg ucgacgaggu gcccaagggc cugaccggga gcuggacgc ccggaagauc   1620
cgcgagaucc ucaucaaggc caagaagggc ggcaagaucg ccgucugagg acuaguagau   1680
cuaaaaaaaa aaaaaaaaaa aaaaaaaaaa aaaaaaaaaa aaaaaaaaaa aaaaaaaaaa   1740
aaaaaa                                                              1746
```

<210> SEQ ID NO 5
<211> LENGTH: 1745
<212> TYPE: RNA
<213> ORGANISM: Artificial Sequence
<220> FEATURE:
<223> OTHER INFORMATION: Photinus pyralis luciferase C-enriched

<400> SEQUENCE: 5

```
ggagaaagcu uaccauggag gacgccaaga acaucaagaa gggccccgcc cccuucuacc     60
cccucgagga cggcaccgcc ggcgagcagc uccacaaggc caugaagcgc uacgcccucg    120
uccccggcac caucgccuuc accgacgccc acaucgaggu cgacaucacc uacgccgagu    180
acuucgagau guccgucgc cucgccgagg ccaugaagcg cuacgccuc aacaccaacc    240
accgcaucgu cgucugcucc gagaacuccc uccaguucuu caugcccguc cucggcgccc    300
ucuuaucgg cgucgccguc gccccgcca acgacaucua caacgagcgc gagcccucaa    360
cuccaguggg caucucccag cccaccgucg ucuucgucuc caagaagggc cuccagaaga    420
uccucaacgu ccagaagaag cuccccauca uccagaagau caucaucaug gacuccaaga    480
ccgacuacca gggcuuccag uccauguaua ccuucgucac cucccaccuc cccccggcu    540
ucaacgagua cgacuucguc ccgagaaccu ugaccgcga caagaccauc gcccucauca    600
ugaacuccuc cggcuccacc ggccuccca aggacgucgc ccucccccac cgcaccgccu    660
gcgucgccuu cucccacgcc cgcgacccca ucuucggcaa ccagaucauc cccgacaccg    720
```

| | |
|---|---|
| ccauccucuc cgucguccec uuccaccacg gcuucggcau guucaccacc cucggcuacc | 780 |
| ucaucugcgg cuuccgcguc guccucaugu accgcuucga ggaggagcuc uuccuccgcu | 840 |
| cccuccagga cuacaagauc cagucegecc uccucgucec cacccucuuc uccuucuucg | 900 |
| ccaaguccac ccucaucgac aaguacgacc ucuccaaccu ccacgagauc gccuccggcg | 960 |
| gcgcccccu cuccaaggag gucggcgagg ccgucgccaa gcgcuuccac cuccccggca | 1020 |
| uccgccaggg cuacgccuc accgagacca ccuccgccau ccucaucacc cccgagggcg | 1080 |
| acgacaagcc cggcgccguc ggcaaggucg uccccuucuu cgaggccaag gucgucgacc | 1140 |
| ucgacaccgg caagacccuc ggcgucaacc agcgcggcga gcucugcguc cgcggccca | 1200 |
| ugaucauguc cggcuacguc aacaaccccg aggccaccaa cgcccucauc gacaaggacg | 1260 |
| gcuggcucca cuccggcgac aucgccuacu gggacgagga cgagcacuuc uucaucgucg | 1320 |
| accgccucaa gucccucauc aaguacaagg gcuaccaggu cgcccccgcc gagcucgagu | 1380 |
| ccauccuccu ccagcacccc aacaucuucg acgccggcgu cgccggccuc cccgacgacg | 1440 |
| acgccggcga gcuccccgcc gccgucgucg uccucgagca cggcaagacc augaccgaga | 1500 |
| aggagaucgu cgacuacguc gccucccagg ucaccaccgc caagaagcuc cgcggcggcg | 1560 |
| ucgucuucgu cgacgaggue cccaagggec ucaccggcaa gcucgacgec cgcaagaucc | 1620 |
| gcgagauccu caucaaggcc aagaagggcg gcaagaucgc cgucgagga cuaguagauc | 1680 |
| uaaaaaaaa aaaaaaaaaa aaaaaaaaaa aaaaaaaaaa aaaaaaaaaa aaaaaaaaaa | 1740 |
| aaaaa | 1745 |

<210> SEQ ID NO 6
<211> LENGTH: 2035
<212> TYPE: RNA
<213> ORGANISM: Artificial Sequence
<220> FEATURE:
<223> OTHER INFORMATION: Photinus pyralis luciferase G/C-enriched

<400> SEQUENCE: 6

| | |
|---|---|
| ggggcgcugc cuacggaggu ggcagccauc uccuucucgg caucaagcuu accauggagg | 60 |
| acgccaagaa caucaagaag ggccccgccc cguucuaccc ccuggaggac gggaccgcgg | 120 |
| gcgagcagcu ccacaaggcc augaagcggu acgcccuggu gcccgggacc aucgccuuca | 180 |
| cggacgccca caucgagguc gacaucaccu acgcggagua cuucgagaug agcgugcgcc | 240 |
| uggccgaggc caugaagcgg uacggccuca acaccaacca ccgcaucgug gucugcuccg | 300 |
| agaacagccu gcaguucuuc augcccgugc uggggcccu cuucaucggc guggcggucg | 360 |
| ccccggccaa cgacaucuac aacgagcggg agcugcugaa cuccaugggc aucagccagc | 420 |
| ccaccguggu guucgucucc aagaagggc uccagaagau ccugaacgug cagaagaagc | 480 |
| ugccgaucau ccagaagauc aucaucaugg acagcaagac ggacuaccag ggcuuccagu | 540 |
| ccauguauac cuucgugacc agccaccucc ccccggggu caacgaguac gacuucgucc | 600 |
| ccgaguccuu cgaccgcgac aagaccaucg cccugaucau gaacagcucc ggcagcacgg | 660 |
| ggcugcccaa gggcguggcc cucccccacc ggaccgcgug cgucgcuuc ucccacgccc | 720 |
| gggacccgau cuucggcaac cagaucaucc ccgacaccgc cauccugagc gucgugcccu | 780 |
| uccaccacgg guucggcaug uucaccacgc ugggguaccu caucugcggc uuccgcgugg | 840 |
| uccugaugua ccgguucgag gaggagcugu uccuccgcuc ccugcaggac uacaagaucc | 900 |
| agagcgcccu gcucgugccc acccuguucu ccuucuucgc caagagcacc cugaucgaca | 960 |
| aguacgaccu cuccaaccug cacgagaucg cgagcggcgg ggccccgcug agcaaggagg | 1020 |

-continued

```
ugggcgaggc cgucgccaag cgguuccacc uccccgggau ccgccagggc uacgggcuga    1080
ccgagacgac cuccgccauc cugaucaccc ccgagggcga cgacaagccc ggcgcggugg    1140
ggaaggnggu cccguucuuc gaggccaagg uggucgaccu cgacaccggc aagacgcugg    1200 ggugaacca gcggggcgag cugugcgugc gcgggcccau gaucaugagc ggcuacguca    1260
acaaccccga ggccaccaac gcccucaucg acaaggacgg cuggcugcac uccggggaca    1320
ucgccuacug ggacgaggac gagcacuucu ucaucgugga ccggcugaag agccucauca    1380
aguacaaggg cuaccaggug gcgcccgccg agcuggaguc cauccugcuc cagcacccga    1440
acaucuucga cgccggguc gccggccugc ccgacgacga cgcgggggag cugccccgccg    1500 ccguggnggu ccucgagcac ggcaagacca ugaccgagaa ggagaucgug gacuacgugg    1560
ccagccaggu cacgaccgcc aagaagcugc gcggcggggu ggnguucguc gacgaggugc    1620
ccaagggccu gaccgggaag cuggacgcgc ggaagauccg cgagauccuc aucaaggcca    1680
agaagggcgg caagaucgcc gucugaggac uagugcauca cauuuaaaag caucucagcc    1740
uaccaugaga auaagagaaa gaaaaugaag aucaauagcu auucaucuc uuuuucuuuu    1800 ucguuggugu aaagccaaca cccugucuaa aaaacauaaa uuucuuuaau cauuuugccu    1860
cuuuucucug ugcuucaauu aauaaaaaau ggaaagaacc uagaucuaaa aaaaaaaaaa    1920
aaaaaaaaaa aaaaaaaaaa aaaaaaaaaa aaaaaaaaaa aaaaaaaaaa augcaucccc    1980
cccccccccc cccccccccc ccccccccaaa ggcucuuuuc agagccacca gaauu        2035
```

<210> SEQ ID NO 7
<211> LENGTH: 2035
<212> TYPE: RNA
<213> ORGANISM: Artificial Sequence
<220> FEATURE:
<223> OTHER INFORMATION: Photinus pyralis luciferase C-enriched

<400> SEQUENCE: 7

```
ggggcgcugc cuacggaggu ggcagccauc uccuucucgg caucaagcuu accauggagg    60
acgccaagaa caucaagaag ggccccgccc ccuucuaccc ccucgaggac ggcaccgccg    120
gcgagcagcu ccacaaggcc augaagcgcu acgcccucgu ccccggcacc aucgccuuca    180
ccgacgccca caucgagguc gacaucaccu acgccgagua cuucgagaug uccgucgcc    240 ucgccgaggc cauggagcgc uacggccuca acaccaacca ccgcaucguc gucugcuccg    300 agaaccccu ccaguucuuc augccccguc ucggcgcccu cuucaucggc gucgccgucg    360
cccccgccaa cgacaucuac aacgagcgcg agccccucaa cuccaugggc aucucccagc    420
ccaccgucgu cuucgucucc aagaagggcc uccagaagau ccucaacguc cagaagaagc    480
uccccaucau ccagaagauc aucaucaugg acuccaagac cgacuaccag ggcuuccagu    540
ccauguauac cuucgucacc ucccaccucc ccccggcuu caacgaguac gacuucgucc    600
ccgaguccuu cgaccgcgac aagaccaucg cccucaucau gaacuccucc ggcuccaccg    660
gccuccccaa gggcgucgcc cuccccccacc gcaccgccug cgucgcuuc ucccacgccc    720 gcgaccccau cuucggcaac cagaucaucc ccgacaccgc caucucuccc gucguccccu    780
uccaccacgg cuucggcaug uucaccaccc ucggcuaccu caucgcggc uuccgcgucg    840 uccucaugua ccgcuucgag gaggagcucu uccuccgcuc ccuccaggac uacaagaucc    900
aguccgcccu ccucgucccc acccucuucu ccuucuucgc caaguccacc cucaucgaca    960
aguacgaccu cucccaaccuc cacgagaucg ccucccggcgg cgcccccccuc uccaaggagg    1020
```

```
ucggcgaggc cgucgccaag cgcuuccacc uccccggcau ccgccagggc uacgccuca     1080 ccgagaccac cuccgccauc cucaucaccc ccgagggcga cgacaagccc ggcgccgucg   1140
gcaaggucgu ccccuucuuc gaggccaagg ucgucgaccu cgacaccggc aagacccucg   1200
gcgucaacca gcgcggcgag cucugcgucc gcggcgcccau gaucaugucc ggcuacguca  1260
acaaccccga ggccaccaac gcccucaucg acaaggacgg cuggcuccac uccggcgaca   1320
ucgccuacug ggacgaggac gagcacuucu caucgucga ccgccucaag ucccucauca    1380
aguacaaggg cuaccagguc gccccgccg agcucgaguc cauccuccuc cagcacccca    1440
acaucuucga cgccgcguc gccggccucc ccgacgacga cgccggcgag cuccccgccg    1500
ccgucgucgu ccucgagcac ggcaagacca ugaccgagaa ggagaucguc gacuacgucg   1560
ccucccaggu caccaccgcc aagaagcucc gcggcggcgu cgucuucguc gacgaggucc   1620
ccaagggccu caccggcaag cucgacgccc gcaagauccg cgagauccuc aucaaggcca   1680
agaagggcgg caagauccgc gucugaggac uagugcauca cauuuaaaag caucucagcc   1740
uaccaugaga auaagagaaa gaaaaugaag aucaauagcu auucaucuc uuuuucuuuu    1800 ucguuggugu aaagccaaca cccugucuaa aaaacauaaa uuucuuuaau cauuuugccu   1860
cuuuucucug ugcuucaauu aauaaaaaau ggaaagaacc uagaucuaaa aaaaaaaaaa   1920
aaaaaaaaaa aaaaaaaaaa aaaaaaaaaa aaaaaaaaaa aaaaaaaaaa augcaucccc   1980
cccccccccc cccccccccc cccccccaaa ggcucuuuuc agagccacca gaauu        2035

<210> SEQ ID NO 8
<211> LENGTH: 18
<212> TYPE: DNA
<213> ORGANISM: Artificial Sequence
<220> FEATURE:
<223> OTHER INFORMATION: T7 RNA polymerase promoter sequence

<400> SEQUENCE: 8
taatacgact cactatag                                                 18

<210> SEQ ID NO 9
<211> LENGTH: 18
<212> TYPE: DNA
<213> ORGANISM: Artificial Sequence
<220> FEATURE:
<223> OTHER INFORMATION: T3 RNA polymerase promoter sequence

<400> SEQUENCE: 9
aattaaccct cactaaag                                                 18

<210> SEQ ID NO 10
<211> LENGTH: 18
<212> TYPE: DNA
<213> ORGANISM: Artificial Sequence
<220> FEATURE:
<223> OTHER INFORMATION: SP6 RNA polymerase promoter sequence

<400> SEQUENCE: 10
atttaggtga cactatag                                                 18

<210> SEQ ID NO 11
<211> LENGTH: 13
<212> TYPE: RNA
<213> ORGANISM: Artificial Sequence
<220> FEATURE:
<223> OTHER INFORMATION: Kozak sequence

<400> SEQUENCE: 11
```

```
gccgccacca ugg                                                    13

<210> SEQ ID NO 12
<211> LENGTH: 14
<212> TYPE: RNA
<213> ORGANISM: Artificial Sequence
<220> FEATURE:
<223> OTHER INFORMATION: stabilization sequence consensus
<220> FEATURE:
<221> NAME/KEY: misc_feature
<222> LOCATION: (5)..(5)
<223> OTHER INFORMATION: n can be 0 - 5 nucleotides, n is a, g , c or t
<220> FEATURE:
<221> NAME/KEY: misc_feature
<222> LOCATION: (10)..(10)
<223> OTHER INFORMATION: y can be 0 - 4 pyrimidines, y is t/u or c

<400> SEQUENCE: 12
yccancccwy cycc                                                   14
```